United States Patent
Boismier et al.

(10) Patent No.: US 8,057,534 B2
(45) Date of Patent: Nov. 15, 2011

(54) BIOERODIBLE ENDOPROSTHESES AND METHODS OF MAKING THE SAME

(75) Inventors: Dennis A. Boismier, Shorewood, MN (US); Timothy S. Girton, Edina, MN (US); Steven R. Larsen, Lino Lakes, MN (US); Matt Shedlov, Rockford, MN (US); Ken Merdan, Greenfield, MN (US); Barry O'Brien, Galway (IE)

(73) Assignee: Boston Scientific SciMed, Inc., Maple Grove, MN (US)

( * ) Notice: Subject to any disclaimer, the term of this patent is extended or adjusted under 35 U.S.C. 154(b) by 456 days.

(21) Appl. No.: 11/855,516

(22) Filed: Sep. 14, 2007

(65) Prior Publication Data
US 2008/0082162 A1    Apr. 3, 2008

Related U.S. Application Data

(60) Provisional application No. 60/844,966, filed on Sep. 15, 2006.

(51) Int. Cl.
*A61F 2/06*    (2006.01)
(52) U.S. Cl. ............... 623/1.38; 623/1.44; 623/1.46; 623/1.15
(58) Field of Classification Search .......... 623/1.38
See application file for complete search history.

(56) References Cited

U.S. PATENT DOCUMENTS

| | | |
|---|---|---|
| 2,950,187 A | 8/1960 | Ototani |
| 3,560,362 A | 2/1971 | Kasamatsu et al. |
| 3,569,660 A | 3/1971 | Houldcroft |
| 3,687,135 A | 8/1972 | Stroganov et al. |
| 3,758,396 A | 9/1973 | Vieth et al. |
| 3,868,578 A | 2/1975 | Oldham |
| 3,910,819 A | 10/1975 | Rembaum et al. |
| 3,948,254 A | 4/1976 | Zaffaroni |
| 3,952,334 A | 4/1976 | Bokros et al. |
| 3,993,072 A | 11/1976 | Zaffaroni |
| 4,002,877 A | 1/1977 | Banas |
| 4,101,984 A | 7/1978 | MacGregor |
| 4,143,661 A | 3/1979 | LaForge et al. |
| 4,202,055 A | 5/1980 | Reiner et al. |
| 4,237,559 A | 12/1980 | Borom |
| 4,308,868 A | 1/1982 | Jhabvala |
| 4,334,327 A | 6/1982 | Lyman et al. |
| 4,401,546 A | 8/1983 | Nakamura et al. |
| 4,532,929 A | 8/1985 | Mattei et al. |
| 4,539,061 A | 9/1985 | Sagiv |
| 4,542,539 A | 9/1985 | Rowe et al. |
| 4,585,652 A | 4/1986 | Miller et al. |

(Continued)

FOREIGN PATENT DOCUMENTS

AU    739 507    11/1998

(Continued)

OTHER PUBLICATIONS

International Preliminary Report on Patentability received in Application No. PCT/US2007/078505, mailed Mar. 26, 2009, 7 pages.

(Continued)

*Primary Examiner* — David Isabella
*Assistant Examiner* — Jacqueline Woznicki
(74) *Attorney, Agent, or Firm* — Fish & Richardson P.C.

(57) ABSTRACT

A bioerodible endoprosthesis erodes to a desirable geometry that can provide, e.g., improved mechanical properties or degradation characteristics.

23 Claims, 12 Drawing Sheets

U.S. PATENT DOCUMENTS

| | | |
|---|---|---|
| 4,634,502 A | 1/1987 | Callahan et al. |
| 4,655,771 A | 4/1987 | Wallsten |
| 4,657,544 A | 4/1987 | Pinchuk |
| 4,665,896 A | 5/1987 | LaForge et al. |
| 4,705,502 A | 11/1987 | Patel |
| 4,713,070 A | 12/1987 | Mano |
| 4,725,273 A | 2/1988 | Kira |
| 4,733,665 A | 3/1988 | Palmaz |
| 4,767,418 A | 8/1988 | Deininger et al. |
| 4,784,659 A | 11/1988 | Fleckenstein et al. |
| 4,800,882 A | 1/1989 | Gianturco |
| 4,804,382 A | 2/1989 | Turina et al. |
| 4,886,062 A | 12/1989 | Wiktor |
| 4,954,126 A | 9/1990 | Wallsten |
| 4,976,692 A | 12/1990 | Atad |
| 4,994,071 A | 2/1991 | MacGregor |
| 5,024,671 A | 6/1991 | Tu et al. |
| 5,059,211 A | 10/1991 | Stack et al. |
| 5,061,275 A | 10/1991 | Wallsten et al. |
| 5,061,914 A | 10/1991 | Busch et al. |
| 5,073,365 A | 12/1991 | Katz et al. |
| 5,079,203 A | 1/1992 | Pinnavaia |
| 5,091,024 A | 2/1992 | DeBold et al. |
| 5,091,205 A | 2/1992 | Fan |
| 5,102,403 A | 4/1992 | Alt |
| 5,120,322 A | 6/1992 | Davis et al. |
| 5,125,971 A | 6/1992 | Nonami et al. |
| 5,147,370 A | 9/1992 | McNamara et al. |
| 5,163,958 A | 11/1992 | Pinchuk |
| 5,195,969 A | 3/1993 | Wang et al. |
| 5,205,921 A | 4/1993 | Shirkanzadeh |
| 5,234,457 A | 8/1993 | Andersen |
| 5,236,413 A | 8/1993 | Feiring |
| 5,236,447 A | 8/1993 | Kubo et al. |
| 5,270,086 A | 12/1993 | Hamlin |
| 5,279,292 A | 1/1994 | Baumann et al. |
| 5,290,585 A | 3/1994 | Elton |
| 5,292,558 A | 3/1994 | Heller et al. |
| 5,302,414 A | 4/1994 | Alkhimov et al. |
| 5,304,121 A | 4/1994 | Sahatjian |
| 5,304,195 A | 4/1994 | Twyford, Jr. et al. |
| 5,306,286 A | 4/1994 | Stack et al. |
| 5,314,453 A | 5/1994 | Jeutter |
| 5,322,520 A | 6/1994 | Milder |
| 5,342,348 A | 8/1994 | Kaplan |
| 5,348,553 A | 9/1994 | Whitney |
| 5,356,433 A | 10/1994 | Rowland et al. |
| 5,360,440 A | 11/1994 | Andersen |
| 5,366,504 A | 11/1994 | Andersen et al. |
| 5,380,298 A | 1/1995 | Zabetakis et al. |
| 5,383,935 A | 1/1995 | Shirkhanzadeh |
| 5,385,776 A | 1/1995 | Maxfield et al. |
| 5,397,307 A | 3/1995 | Goodin |
| 5,405,367 A | 4/1995 | Schulman et al. |
| 5,421,955 A | 6/1995 | Lau et al. |
| 5,439,446 A | 8/1995 | Barry |
| 5,443,458 A | 8/1995 | Eury |
| 5,443,496 A | 8/1995 | Schwartz et al. |
| 5,443,500 A | 8/1995 | Sigwart |
| 5,449,373 A | 9/1995 | Pinchasik et al. |
| 5,449,382 A | 9/1995 | Dayton |
| 5,458,627 A | 10/1995 | Baranowski, Jr. et al. |
| 5,462,575 A | 10/1995 | Del Corso |
| 5,464,450 A | 11/1995 | Buscemi et al. |
| 5,464,650 A | 11/1995 | Berg et al. |
| 5,468,574 A | 11/1995 | Ehrenberg et al. |
| 5,474,797 A | 12/1995 | Sioshansi et al. |
| 5,500,013 A | 3/1996 | Buscemi et al. |
| 5,514,154 A | 5/1996 | Lau et al. |
| 5,527,337 A | 6/1996 | Stack et al. |
| 5,536,573 A | 7/1996 | Rubner et al. |
| 5,545,208 A | 8/1996 | Wolff et al. |
| 5,549,664 A | 8/1996 | Hirata et al. |
| 5,551,954 A | 9/1996 | Buscemi et al. |
| 5,578,075 A | 11/1996 | Dayton |
| 5,587,200 A | 12/1996 | Lorenz et al. |
| 5,587,507 A | 12/1996 | Kohn et al. |
| 5,591,222 A | 1/1997 | Susawa et al. |
| 5,591,224 A | 1/1997 | Schwartz et al. |
| 5,599,352 A | 2/1997 | Dinh et al. |
| 5,603,556 A | 2/1997 | Klink |
| 5,605,696 A | 2/1997 | Eury et al. |
| 5,607,463 A | 3/1997 | Schwartz et al. |
| 5,609,629 A | 3/1997 | Fearnot et al. |
| 5,614,549 A | 3/1997 | Greenwald et al. |
| 5,624,411 A | 4/1997 | Tuch |
| 5,628,787 A | 5/1997 | Mayer |
| 5,629,077 A | 5/1997 | Turnlund et al. |
| 5,632,771 A | 5/1997 | Boatman et al. |
| 5,632,840 A | 5/1997 | Campbell |
| 5,649,951 A | 7/1997 | Davidson |
| 5,658,327 A | 8/1997 | Altman et al. |
| 5,674,192 A | 10/1997 | Sahatjian et al. |
| 5,674,242 A | 10/1997 | Phan |
| 5,676,685 A | 10/1997 | Razavi |
| 5,679,440 A | 10/1997 | Kubota |
| 5,690,670 A | 11/1997 | Davidson |
| 5,693,085 A | 12/1997 | Buirge et al. |
| 5,693,928 A | 12/1997 | Egitto et al. |
| 5,697,967 A | 12/1997 | Dinh et al. |
| 5,700,286 A | 12/1997 | Tartaglia et al. |
| 5,716,981 A | 2/1998 | Hunter et al. |
| 5,721,049 A | 2/1998 | Marcolongo et al. |
| 5,725,570 A | 3/1998 | Heath |
| 5,733,925 A | 3/1998 | Kunz et al. |
| 5,741,331 A | 4/1998 | Pinchuk |
| 5,744,515 A | 4/1998 | Clapper |
| 5,749,809 A | 5/1998 | Lin |
| 5,749,880 A | 5/1998 | Banas et al. |
| 5,758,562 A | 6/1998 | Thompson |
| 5,759,192 A | 6/1998 | Saunders |
| 5,761,775 A | 6/1998 | Legome et al. |
| 5,769,883 A | 6/1998 | Buscemi et al. |
| 5,769,884 A | 6/1998 | Solovay |
| 5,773,925 A | 6/1998 | Kimura et al. |
| 5,776,184 A | 7/1998 | Tuch |
| 5,779,904 A | 7/1998 | Ruderman et al. |
| 5,780,807 A | 7/1998 | Saunders |
| 5,788,626 A | 8/1998 | Thompson |
| 5,788,687 A | 8/1998 | Batich et al. |
| 5,788,979 A | 8/1998 | Alt et al. |
| 5,797,898 A | 8/1998 | Santini, Jr. et al. |
| 5,800,511 A | 9/1998 | Mayer |
| 5,815,904 A | 10/1998 | Clubb et al. |
| 5,817,046 A | 10/1998 | Glickman |
| 5,824,045 A | 10/1998 | Alt |
| 5,824,048 A | 10/1998 | Tuch |
| 5,824,077 A | 10/1998 | Mayer |
| 5,830,217 A | 11/1998 | Ryan |
| 5,833,715 A | 11/1998 | Vachon et al. |
| 5,837,007 A | 11/1998 | Altman et al. |
| 5,837,275 A | 11/1998 | Burrell et al. |
| 5,840,387 A | 11/1998 | Berlowitz-Tarrant et al. |
| 5,843,089 A | 12/1998 | Sahatjian et al. |
| 5,843,172 A | 12/1998 | Yan |
| 5,854,382 A | 12/1998 | Loomis |
| 5,858,556 A | 1/1999 | Eckert et al. |
| 5,869,140 A | 2/1999 | Blohowiak et al. |
| 5,873,904 A | 2/1999 | Ragheb et al. |
| 5,876,756 A | 3/1999 | Takada et al. |
| 5,879,697 A | 3/1999 | Ding et al. |
| 5,880,661 A | 3/1999 | Davidson et al. |
| 5,882,335 A | 3/1999 | Leone et al. |
| 5,891,108 A | 4/1999 | Leone et al. |
| 5,891,191 A | 4/1999 | Stinson |
| 5,899,935 A | 5/1999 | Ding |
| 5,902,266 A | 5/1999 | Leone et al. |
| 5,906,759 A | 5/1999 | Richter |
| 5,907,893 A | 6/1999 | Zadno-Azizi et al. |
| 5,922,005 A | 7/1999 | Richter et al. |
| 5,922,021 A | 7/1999 | Jang |
| 5,928,247 A | 7/1999 | Barry et al. |
| 5,935,506 A | 8/1999 | Schmitz et al. |
| 5,938,903 A | 8/1999 | Broderick |
| 5,941,843 A | 8/1999 | Atanasoska et al. |
| 5,951,458 A | 9/1999 | Hastings et al. |
| 5,951,881 A | 9/1999 | Rogers et al. |

| | | | | | | |
|---|---|---|---|---|---|---|
| 5,954,706 A | 9/1999 | Sahatjian | | 6,258,117 B1 | 7/2001 | Camrud et al. |
| 5,957,975 A | 9/1999 | Lafont et al. | | 6,264,687 B1 | 7/2001 | Tomonto |
| 5,958,440 A | 9/1999 | Burrell et al. | | 6,270,831 B2 | 8/2001 | Kumar et al. |
| 5,961,547 A | 10/1999 | Razavi | | 6,273,908 B1 | 8/2001 | Ndondo-Lay |
| 5,968,091 A | 10/1999 | Pinchuk et al. | | 6,273,913 B1 | 8/2001 | Wright et al. |
| 5,968,092 A | 10/1999 | Buscemi et al. | | 6,277,078 B1 | 8/2001 | Porat et al. |
| 5,972,027 A | 10/1999 | Johnson | | 6,280,385 B1 | 8/2001 | Melzer et al. |
| 5,972,192 A | 10/1999 | Dubin et al. | | 6,280,411 B1 | 8/2001 | Lennox |
| 5,976,169 A | 11/1999 | Imran | | 6,283,386 B1 | 9/2001 | Van Steenkiste et al. |
| 5,976,454 A | 11/1999 | Sterzel et al. | | 6,287,331 B1 | 9/2001 | Heath |
| 5,977,204 A | 11/1999 | Boyan et al. | | 6,287,332 B1 | 9/2001 | Bolz et al. |
| 5,980,554 A | 11/1999 | Lenker et al. | | 6,287,335 B1 | 9/2001 | Drasler et al. |
| 5,980,564 A | 11/1999 | Stinson | | 6,287,628 B1 | 9/2001 | Hossainy et al. |
| 5,980,566 A | 11/1999 | Alt et al. | | 6,290,721 B1 | 9/2001 | Heath |
| 6,001,125 A | 12/1999 | Golds et al. | | 6,290,722 B1 | 9/2001 | Wang |
| 6,013,591 A | 1/2000 | Ying et al. | | 6,291,076 B1 | 9/2001 | Nakatsugawa |
| 6,017,553 A | 1/2000 | Burrell et al. | | 6,299,604 B1 | 10/2001 | Ragheb et al. |
| 6,017,577 A | 1/2000 | Hostettler et al. | | 6,299,755 B1 | 10/2001 | Richter |
| 6,021,347 A | 2/2000 | Herbst et al. | | 6,306,144 B1 | 10/2001 | Sydney et al. |
| 6,025,036 A | 2/2000 | McGill et al. | | 6,309,414 B1 | 10/2001 | Rolando et al. |
| 6,027,742 A | 2/2000 | Lee et al. | | 6,312,463 B1 | 11/2001 | Rourke et al. |
| 6,034,295 A | 3/2000 | Rehberg et al. | | 6,315,708 B1 | 11/2001 | Salmon et al. |
| 6,056,776 A | 5/2000 | Lau et al. | | 6,323,146 B1 | 11/2001 | Pugh et al. |
| 6,063,101 A | 5/2000 | Jacobsen et al. | | 6,325,825 B1 | 12/2001 | Kula et al. |
| 6,071,305 A | 6/2000 | Brown et al. | | 6,327,504 B1 | 12/2001 | Dolgin et al. |
| 6,080,190 A | 6/2000 | Schwartz | | 6,331,312 B1 | 12/2001 | Lee et al. |
| 6,086,773 A | 7/2000 | Dufresne et al. | | 6,335,029 B1 | 1/2002 | Kamath et al. |
| 6,096,070 A | 8/2000 | Ragheb et al. | | 6,337,076 B1 | 1/2002 | Studin |
| 6,096,175 A | 8/2000 | Roth | | 6,338,739 B1 | 1/2002 | Datta et al. |
| 6,099,561 A | 8/2000 | Alt | | 6,342,507 B1 | 1/2002 | Naicker et al. |
| 6,099,562 A * | 8/2000 | Ding et al. ............ 623/1.46 | | 6,344,055 B1 | 2/2002 | Shukov |
| 6,106,473 A | 8/2000 | Violante et al. | | 6,348,960 B1 | 2/2002 | Etori et al. |
| 6,107,004 A | 8/2000 | Donadio, III | | 6,358,276 B1 | 3/2002 | Edwin |
| 6,117,592 A | 9/2000 | Hoshino et al. | | 6,364,823 B1 | 4/2002 | Garibaldi et al. |
| 6,120,260 A | 9/2000 | Jirele | | 6,364,856 B1 | 4/2002 | Ding et al. |
| 6,120,535 A | 9/2000 | McDonald et al. | | 6,364,903 B2 | 4/2002 | Tseng et al. |
| 6,120,660 A | 9/2000 | Chu et al. | | 6,366,808 B1 | 4/2002 | Schroeppel et al. |
| 6,123,861 A | 9/2000 | Santini, Jr. et al. | | 6,368,658 B1 | 4/2002 | Schwarz et al. |
| 6,132,463 A | 10/2000 | Lee et al. | | 6,369,355 B1 | 4/2002 | Saunders |
| 6,139,573 A | 10/2000 | Sogard et al. | | 6,375,826 B1 | 4/2002 | Wang et al. |
| 6,139,574 A | 10/2000 | Vacanti et al. | | 6,379,379 B1 | 4/2002 | Wang |
| 6,139,913 A | 10/2000 | Van Steenkiste et al. | | 6,379,382 B1 | 4/2002 | Yang et al. |
| 6,140,740 A | 10/2000 | Porat et al. | | 6,379,383 B1 | 4/2002 | Palmaz et al. |
| 6,143,370 A | 11/2000 | Panagiotou et al. | | 6,379,392 B1 | 4/2002 | Walak |
| 6,153,252 A | 11/2000 | Hossainy et al. | | 6,383,214 B1 | 5/2002 | Banas et al. |
| 6,159,142 A | 12/2000 | Alt | | 6,387,121 B1 | 5/2002 | Alt |
| 6,162,238 A | 12/2000 | Kaplan et al. | | 6,387,124 B1 | 5/2002 | Buscemi et al. |
| 6,164,284 A | 12/2000 | Schulman et al. | | 6,390,967 B1 | 5/2002 | Forman et al. |
| 6,165,211 A | 12/2000 | Thompson | | 6,391,033 B2 | 5/2002 | Ryan |
| 6,167,307 A | 12/2000 | Hess | | 6,391,052 B2 | 5/2002 | Buirge et al. |
| 6,168,602 B1 | 1/2001 | Ryan | | 6,395,326 B1 | 5/2002 | Castro et al. |
| 6,170,488 B1 | 1/2001 | Spillman, Jr. et al. | | 6,398,806 B1 | 6/2002 | You |
| 6,174,329 B1 | 1/2001 | Callol et al. | | 6,409,754 B1 | 6/2002 | Smith et al. |
| 6,174,330 B1 | 1/2001 | Stinson | | 6,419,692 B1 | 7/2002 | Yang et al. |
| 6,180,222 B1 | 1/2001 | Schulz et al. | | 6,423,092 B2 | 7/2002 | Datta et al. |
| 6,185,455 B1 | 2/2001 | Loeb et al. | | 6,425,855 B2 | 7/2002 | Tomonto |
| 6,185,457 B1 | 2/2001 | Kroll et al. | | 6,436,133 B1 | 8/2002 | Furst et al. |
| 6,190,404 B1 | 2/2001 | Palmaz et al. | | 6,440,166 B1 | 8/2002 | Kolluri |
| 6,192,271 B1 | 2/2001 | Hayman | | 6,440,487 B1 | 8/2002 | Delfino et al. |
| 6,201,991 B1 | 3/2001 | Chekanov | | 6,440,503 B1 | 8/2002 | Merdan et al. |
| 6,203,536 B1 | 3/2001 | Berg et al. | | 6,447,540 B1 | 9/2002 | Fontaine et al. |
| 6,206,914 B1 | 3/2001 | Soykan et al. | | 6,458,153 B1 | 10/2002 | Bailey et al. |
| 6,206,915 B1 | 3/2001 | Fagan et al. | | 6,468,304 B1 | 10/2002 | Dubois-Rande et al. |
| 6,206,916 B1 | 3/2001 | Furst | | 6,471,721 B1 | 10/2002 | Dang |
| 6,212,434 B1 | 4/2001 | Scheiner | | 6,471,980 B2 | 10/2002 | Sirhan et al. |
| 6,214,037 B1 | 4/2001 | Mitchell et al. | | 6,475,477 B1 | 11/2002 | Kohn et al. |
| 6,214,042 B1 | 4/2001 | Jacobsen et al. | | 6,478,815 B1 | 11/2002 | Alt |
| 6,217,607 B1 | 4/2001 | Alt | | 6,479,146 B1 | 11/2002 | Caruso et al. |
| 6,231,597 B1 | 5/2001 | Deem et al. | | 6,486,588 B2 | 11/2002 | Doron |
| 6,240,616 B1 | 6/2001 | Yan | | 6,488,702 B1 | 12/2002 | Besselink |
| 6,241,762 B1 | 6/2001 | Shanley | | 6,491,666 B1 | 12/2002 | Santini, Jr. et al. |
| 6,245,103 B1 | 6/2001 | Stinson | | 6,491,720 B1 | 12/2002 | Vallana et al. |
| 6,245,104 B1 | 6/2001 | Alt | | 6,492,096 B1 | 12/2002 | Liu et al. |
| 6,249,952 B1 | 6/2001 | Ding | | 6,503,556 B2 | 1/2003 | Harish et al. |
| 6,251,136 B1 | 6/2001 | Guruwaiya et al. | | 6,503,921 B2 | 1/2003 | Naicker et al. |
| 6,251,980 B1 | 6/2001 | Lan et al. | | 6,506,437 B1 | 1/2003 | Harish et al. |
| 6,253,252 B1 | 6/2001 | Schofield | | 6,506,972 B1 | 1/2003 | Wang |
| 6,253,443 B1 | 7/2001 | Johnson | | 6,514,283 B2 | 2/2003 | DiMatteo et al. |
| 6,254,632 B1 | 7/2001 | Wu et al. | | 6,517,571 B1 | 2/2003 | Brauker et al. |

| | | |
|---|---|---|
| 6,517,888 B1 | 2/2003 | Weber |
| 6,524,274 B1 | 2/2003 | Rosenthal et al. |
| 6,524,334 B1 | 2/2003 | Thompson |
| 6,527,801 B1 | 3/2003 | Dutta |
| 6,527,938 B2 | 3/2003 | Bales et al. |
| 6,530,949 B2 | 3/2003 | Konya et al. |
| 6,530,951 B1 | 3/2003 | Bates et al. |
| 6,537,310 B1 | 3/2003 | Palmaz et al. |
| 6,537,312 B2 | 3/2003 | Datta et al. |
| 6,544,582 B1 | 4/2003 | Yoe |
| 6,545,097 B2 | 4/2003 | Pinchuk et al. |
| 6,549,811 B2 | 4/2003 | Stewart et al. |
| 6,554,854 B1 | 4/2003 | Flanagan |
| 6,558,422 B1 | 5/2003 | Baker et al. |
| 6,558,733 B1 | 5/2003 | Hossainy et al. |
| 6,565,602 B2 | 5/2003 | Rolando et al. |
| 6,569,489 B1 | 5/2003 | Li |
| 6,584,349 B1 | 6/2003 | Sage et al. |
| 6,585,764 B2 | 7/2003 | Wright et al. |
| 6,585,765 B1 | 7/2003 | Hossainy et al. |
| 6,586,705 B1 | 7/2003 | Schell |
| 6,589,286 B1 | 7/2003 | Litner |
| 6,599,558 B1 | 7/2003 | Al-Lamee et al. |
| 6,602,287 B1 | 8/2003 | Millare et al. |
| 6,607,598 B2 | 8/2003 | Schwarz et al. |
| 6,613,077 B2 | 9/2003 | Gilligan et al. |
| 6,613,083 B2 | 9/2003 | Alt |
| 6,613,432 B2 | 9/2003 | Zamora et al. |
| 6,616,765 B1 | 9/2003 | Castro et al. |
| 6,626,933 B1 | 9/2003 | Lau et al. |
| 6,626,936 B2 | 9/2003 | Stinson |
| 6,626,939 B1 | 9/2003 | Burnside et al. |
| 6,627,321 B1 | 9/2003 | Ellingsen et al. |
| 6,628,989 B1 | 9/2003 | Penner |
| 6,629,992 B2 | 10/2003 | Bigus et al. |
| 6,635,082 B1 | 10/2003 | Hossainy et al. |
| 6,638,302 B1 | 10/2003 | Curcio et al. |
| 6,641,607 B1 | 11/2003 | Hossainy et al. |
| 6,652,575 B2 | 11/2003 | Wang |
| 6,652,578 B2 | 11/2003 | Bailey et al. |
| 6,652,581 B1 | 11/2003 | Ding |
| 6,652,582 B1 | 11/2003 | Stinson |
| 6,660,034 B1 | 12/2003 | Mandrusov et al. |
| 6,663,662 B2 | 12/2003 | Pacetti et al. |
| 6,663,664 B1 | 12/2003 | Pacetti |
| 6,669,980 B2 | 12/2003 | Hansen |
| 6,673,105 B1 | 1/2004 | Chen |
| 6,673,385 B1 | 1/2004 | Ding et al. |
| 6,673,999 B1 | 1/2004 | Wang et al. |
| 6,676,987 B2 | 1/2004 | Zhong |
| 6,676,989 B2 | 1/2004 | Kirkpatrick et al. |
| 6,689,160 B1 | 2/2004 | Okuda et al. |
| 6,689,803 B2 | 2/2004 | Hunter |
| 6,695,865 B2 | 2/2004 | Boyle et al. |
| 6,696,666 B2 | 2/2004 | Weber et al. |
| 6,696,667 B1 | 2/2004 | Flanagan |
| 6,699,281 B2 | 3/2004 | Vallana et al. |
| 6,699,282 B1 | 3/2004 | Sceusa |
| 6,709,379 B1 | 3/2004 | Brandau et al. |
| 6,709,397 B2 | 3/2004 | Taylor |
| 6,709,451 B1 | 3/2004 | Noble et al. |
| 6,710,053 B2 | 3/2004 | Naicker et al. |
| 6,712,844 B2 | 3/2004 | Pacetti |
| 6,712,845 B2 | 3/2004 | Hossainy |
| 6,713,671 B1 | 3/2004 | Wang et al. |
| 6,716,444 B1 | 4/2004 | Castro et al. |
| 6,719,987 B2 | 4/2004 | Langford et al. |
| 6,720,402 B2 | 4/2004 | Langer et al. |
| 6,723,120 B2 | 4/2004 | Yan |
| 6,723,350 B2 | 4/2004 | Burrell et al. |
| 6,725,901 B1 | 4/2004 | Kramer et al. |
| 6,726,712 B2 | 4/2004 | Raeder-Devens et al. |
| 6,730,117 B1 | 5/2004 | Tseng et al. |
| 6,730,120 B2 | 5/2004 | Berg et al. |
| 6,730,699 B2 | 5/2004 | Li et al. |
| 6,733,513 B2 | 5/2004 | Boyle et al. |
| 6,740,077 B1 | 5/2004 | Brandau et al. |
| 6,743,388 B2 | 6/2004 | Sridharan et al. |
| 6,752,826 B2 | 6/2004 | Holloway et al. |
| 6,752,829 B2 | 6/2004 | Kocur et al. |
| 6,753,071 B1 | 6/2004 | Pacetti |
| 6,758,859 B1 | 7/2004 | Dang et al. |
| 6,764,505 B1 | 7/2004 | Hossainy et al. |
| 6,764,579 B2 | 7/2004 | Veerasamy et al. |
| 6,764,709 B2 | 7/2004 | Flanagan |
| 6,765,144 B1 | 7/2004 | Wang et al. |
| 6,767,360 B1 | 7/2004 | Alt et al. |
| 6,770,086 B1 | 8/2004 | Girton |
| 6,770,729 B2 | 8/2004 | Van Antwerp |
| 6,774,278 B1 | 8/2004 | Ragheb et al. |
| 6,776,022 B2 | 8/2004 | Kula et al. |
| 6,776,094 B1 | 8/2004 | Whitesides et al. |
| 6,776,793 B2 | 8/2004 | Brown et al. |
| 6,780,424 B2 | 8/2004 | Claude |
| 6,783,543 B2 | 8/2004 | Jang |
| 6,790,228 B2 | 9/2004 | Hossainy et al. |
| 6,793,877 B1 | 9/2004 | Pettersen et al. |
| 6,796,435 B2 | 9/2004 | Izumi |
| 6,803,070 B2 | 10/2004 | Weber |
| 6,805,709 B1 | 10/2004 | Schaldach et al. |
| 6,805,898 B1 | 10/2004 | Wu et al. |
| 6,807,440 B2 | 10/2004 | Weber |
| RE38,653 E | 11/2004 | Igaki et al. |
| 6,815,609 B1 | 11/2004 | Wang et al. |
| 6,820,676 B2 | 11/2004 | Palmaz et al. |
| 6,827,737 B2 | 12/2004 | Hill et al. |
| 6,827,966 B2 | 12/2004 | Qiu et al. |
| 6,833,004 B2 | 12/2004 | Ishii et al. |
| 6,846,323 B2 | 1/2005 | Yip et al. |
| 6,846,841 B2 | 1/2005 | Hunter et al. |
| 6,847,837 B1 | 1/2005 | Melzer et al. |
| 6,849,085 B2 | 2/2005 | Marton |
| 6,849,089 B2 | 2/2005 | Stoll |
| 6,852,122 B2 | 2/2005 | Rush |
| 6,854,172 B2 | 2/2005 | Kaese et al. |
| 6,861,088 B2 | 3/2005 | Weber et al. |
| 6,865,810 B2 | 3/2005 | Stinson |
| 6,866,805 B2 | 3/2005 | Hong et al. |
| 6,869,443 B2 | 3/2005 | Buscemi et al. |
| 6,869,701 B1 | 3/2005 | Aita et al. |
| 6,875,227 B2 | 4/2005 | Yoon |
| 6,878,249 B2 | 4/2005 | Kouyama et al. |
| 6,884,429 B2 | 4/2005 | Koziak et al. |
| 6,887,270 B2 | 5/2005 | Miller et al. |
| 6,887,857 B2 | 5/2005 | Naimark et al. |
| 6,896,697 B1 | 5/2005 | Yip et al. |
| 6,899,731 B2 | 5/2005 | Li et al. |
| 6,899,914 B2 | 5/2005 | Schaldach et al. |
| 6,904,658 B2 | 6/2005 | Hines |
| 6,908,506 B2 | 6/2005 | Zimmermann |
| 6,908,622 B2 | 6/2005 | Barry et al. |
| 6,908,624 B2 | 6/2005 | Hossainy et al. |
| 6,913,617 B1 | 7/2005 | Reiss |
| 6,913,765 B2 | 7/2005 | Li et al. |
| 6,918,869 B2 | 7/2005 | Shaw et al. |
| 6,918,927 B2 | 7/2005 | Bates et al. |
| 6,921,390 B2 | 7/2005 | Bucay-Couto et al. |
| 6,923,996 B2 | 8/2005 | Epstein et al. |
| 6,926,735 B2 | 8/2005 | Henderson |
| 6,932,930 B2 | 8/2005 | DeSimone et al. |
| 6,936,066 B2 | 8/2005 | Palmaz et al. |
| 6,939,320 B2 | 9/2005 | Lennox |
| 6,945,993 B2 | 9/2005 | Kveen et al. |
| 6,951,053 B2 | 10/2005 | Padilla et al. |
| 6,953,560 B1 | 10/2005 | Castro et al. |
| 6,953,594 B2 | 10/2005 | Lee et al. |
| 6,954,977 B2 | 10/2005 | Maguire et al. |
| 6,955,661 B1 | 10/2005 | Herweck et al. |
| 6,955,685 B2 | 10/2005 | Escamilla et al. |
| 6,962,822 B2 | 11/2005 | Hart et al. |
| 6,964,817 B2 | 11/2005 | Date et al. |
| 6,971,813 B2 | 12/2005 | Shekalim et al. |
| 6,972,130 B1 | 12/2005 | Lee et al. |
| 6,973,718 B2 | 12/2005 | Sheppard, Jr. et al. |
| 6,979,346 B1 | 12/2005 | Hossainy et al. |
| 6,979,347 B1 | 12/2005 | Wu et al. |
| 6,979,348 B2 | 12/2005 | Sundar |
| 6,981,986 B1 | 1/2006 | Brown et al. |

| | | | | | |
|---|---|---|---|---|---|
| 6,984,404 B1 | 1/2006 | Talton et al. | 2001/0002000 A1 | 5/2001 | Kumar et al. |
| 6,986,899 B2 | 1/2006 | Hossainy et al. | 2001/0002435 A1 | 5/2001 | Berg et al. |
| 6,989,156 B2 | 1/2006 | Gillis | 2001/0013166 A1 | 8/2001 | Yan |
| 6,991,709 B2 | 1/2006 | Gopalraja et al. | 2001/0021871 A1 | 9/2001 | Stinson |
| 7,001,421 B2 | 2/2006 | Cheng et al. | 2001/0021873 A1 | 9/2001 | Stinson |
| 7,004,968 B2 | 2/2006 | Lootz et al. | 2001/0027299 A1 | 10/2001 | Yang et al. |
| 7,011,670 B2 | 3/2006 | Radisch, Jr. | 2001/0029398 A1 | 10/2001 | Jadhav |
| 7,011,678 B2 | 3/2006 | Tenerz et al. | 2001/0029660 A1 | 10/2001 | Johnson |
| 7,011,680 B2 | 3/2006 | Alt | 2001/0032011 A1 | 10/2001 | Stanford |
| 7,018,408 B2 | 3/2006 | Bailey et al. | 2001/0032013 A1 | 10/2001 | Marton |
| 7,022,334 B1 | 4/2006 | Ding et al. | 2001/0032014 A1 | 10/2001 | Yang et al. |
| 7,041,130 B2 | 5/2006 | Santini, Jr. | 2001/0044650 A1 | 11/2001 | Simso et al. |
| 7,048,767 B2 | 5/2006 | Namavar | 2002/0000175 A1 | 1/2002 | Hintermaier et al. |
| 7,048,939 B2 | 5/2006 | Elkins et al. | 2002/0000406 A1 | 1/2002 | Izumi |
| 7,052,488 B2 | 5/2006 | Uhland | 2002/0004060 A1 | 1/2002 | Heublein et al. |
| 7,056,338 B2 | 6/2006 | Shanley et al. | 2002/0007102 A1 | 1/2002 | Salmon et al. |
| 7,056,339 B2 | 6/2006 | Elkins et al. | 2002/0007209 A1 | 1/2002 | Schearder et al. |
| 7,060,051 B2 | 6/2006 | Palasis | 2002/0010505 A1 | 1/2002 | Richter |
| 7,060,240 B2 | 6/2006 | Costa et al. | 2002/0016623 A1 | 2/2002 | Kula et al. |
| 7,063,748 B2 | 6/2006 | Talton | 2002/0016624 A1 | 2/2002 | Patterson et al. |
| 7,067,606 B2 | 6/2006 | Mather et al. | 2002/0028827 A1 | 3/2002 | Naicker et al. |
| 7,070,576 B2 | 7/2006 | O'Brien et al. | 2002/0032477 A1 | 3/2002 | Helmus et al. |
| 7,078,108 B2 | 7/2006 | Zhang et al. | 2002/0035394 A1 | 3/2002 | Fierens et al. |
| 7,099,091 B2 | 8/2006 | Taniguchi et al. | 2002/0038146 A1 | 3/2002 | Harry |
| 7,101,391 B2 | 9/2006 | Scheuermann et al. | 2002/0042039 A1 | 4/2002 | Kim et al. |
| 7,101,394 B2 | 9/2006 | Hamm et al. | 2002/0049495 A1 | 4/2002 | Kutryk et al. |
| 7,105,018 B1 | 9/2006 | Yip et al. | 2002/0051730 A1 | 5/2002 | Bodnar et al. |
| 7,105,199 B2 | 9/2006 | Blinn et al. | 2002/0051846 A1 | 5/2002 | Kirkpatrick et al. |
| 7,108,716 B2 | 9/2006 | Burnside et al. | 2002/0065553 A1 | 5/2002 | Weber |
| 7,157,096 B2 | 1/2007 | Zhang et al. | 2002/0082679 A1 * | 6/2002 | Sirhan et al. ................. 623/1.15 |
| 7,160,592 B2 | 1/2007 | Rypacek et al. | 2002/0087123 A1 | 7/2002 | Hossainy et al. |
| 7,163,715 B1 | 1/2007 | Kramer | 2002/0090313 A1 | 7/2002 | Wang et al. |
| 7,169,173 B2 | 1/2007 | Hossainy et al. | 2002/0091375 A1 | 7/2002 | Sahatjian et al. |
| 7,169,178 B1 * | 1/2007 | Santos et al. ................. 623/1.42 | 2002/0098278 A1 | 7/2002 | Bates et al. |
| 7,195,640 B2 | 3/2007 | Falotico et al. | 2002/0099434 A1 | 7/2002 | Buscemi et al. |
| 7,195,641 B2 | 3/2007 | Palmaz et al. | 2002/0099438 A1 | 7/2002 | Furst |
| 7,198,675 B2 | 4/2007 | Fox et al. | 2002/0103527 A1 | 8/2002 | Kocur et al. |
| 7,208,011 B2 | 4/2007 | Shanley et al. | 2002/0103528 A1 | 8/2002 | Schaldach et al. |
| 7,208,172 B2 | 4/2007 | Birdsall et al. | 2002/0111694 A1 | 8/2002 | Ellingsent et al. |
| 7,220,816 B2 | 5/2007 | Pacetti | 2002/0121497 A1 | 9/2002 | Tomonto |
| 7,226,475 B2 | 6/2007 | Lenz et al. | 2002/0123801 A1 | 9/2002 | Pacetti et al. |
| 7,229,471 B2 | 6/2007 | Gale et al. | 2002/0133222 A1 | 9/2002 | Das |
| 7,235,096 B1 | 6/2007 | Van Tassel et al. | 2002/0133224 A1 | 9/2002 | Bajgar et al. |
| 7,235,098 B2 | 6/2007 | Palmaz | 2002/0138100 A1 | 9/2002 | Stoll et al. |
| 7,238,199 B2 | 7/2007 | Feldman et al. | 2002/0138131 A1 | 9/2002 | Solovay et al. |
| 7,241,295 B2 | 7/2007 | Maguire | 2002/0138136 A1 | 9/2002 | Chandresekaran et al. |
| 7,244,272 B2 | 7/2007 | Dubson et al. | 2002/0138154 A1 | 9/2002 | Li et al. |
| 7,261,732 B2 | 8/2007 | Justino | 2002/0144757 A1 | 10/2002 | Craig et al. |
| 7,261,735 B2 | 8/2007 | Llanos et al. | 2002/0155212 A1 | 10/2002 | Hossainy |
| 7,267,960 B2 | 9/2007 | Galibert et al. | 2002/0165265 A1 | 11/2002 | Hunter et al. |
| 7,279,174 B2 | 10/2007 | Pacetti | 2002/0165578 A1 | 11/2002 | Sawitowski et al. |
| 7,279,175 B2 | 10/2007 | Chen | 2002/0165600 A1 | 11/2002 | Banas et al. |
| 7,294,409 B2 | 11/2007 | Lye et al. | 2002/0165607 A1 | 11/2002 | Alt |
| 7,311,727 B2 | 12/2007 | Mazumder et al. | 2002/0169493 A1 | 11/2002 | Widenhouse et al. |
| 7,323,189 B2 | 1/2008 | Pathak | 2002/0178570 A1 | 12/2002 | Sogard et al. |
| RE40,122 E | 2/2008 | Thompson | 2002/0182241 A1 | 12/2002 | Borenstein et al. |
| 7,331,993 B2 | 2/2008 | White | 2002/0183581 A1 | 12/2002 | Yoe et al. |
| 7,335,375 B2 | 2/2008 | Li et al. | 2002/0187260 A1 | 12/2002 | Sheppard, Jr. et al. |
| 7,344,560 B2 | 3/2008 | Gregorich et al. | 2002/0193336 A1 | 12/2002 | Elkins et al. |
| 7,344,563 B2 | 3/2008 | Vallana et al. | 2002/0193682 A1 | 12/2002 | Torchia et al. |
| 7,393,589 B2 | 7/2008 | Aharonov et al. | 2002/0193869 A1 | 12/2002 | Dang |
| 7,402,173 B2 | 7/2008 | Scheuermann et al. | 2002/0197178 A1 | 12/2002 | Yan |
| 7,416,558 B2 | 8/2008 | Yip et al. | 2002/0198601 A1 | 12/2002 | Bales et al. |
| 7,432,327 B2 | 10/2008 | Glasgow et al. | 2003/0003127 A1 | 1/2003 | Brown et al. |
| 7,462,366 B2 | 12/2008 | Lanphere | 2003/0003220 A1 | 1/2003 | Zhong et al. |
| 7,498,385 B2 | 3/2009 | Swetlin et al. | 2003/0004563 A1 | 1/2003 | Jackson et al. |
| 7,507,433 B2 | 3/2009 | Weber | 2003/0004564 A1 | 1/2003 | Elkins et al. |
| 7,537,610 B2 | 5/2009 | Reiss | 2003/0009214 A1 | 1/2003 | Shanley |
| 7,547,445 B2 | 6/2009 | Chudzik et al. | 2003/0018380 A1 | 1/2003 | Craig et al. |
| 7,563,277 B2 | 7/2009 | Case et al. | 2003/0018381 A1 | 1/2003 | Whitcher et al. |
| 7,637,941 B1 | 12/2009 | Manicka et al. | 2003/0023300 A1 | 1/2003 | Bailey et al. |
| 7,651,527 B2 | 1/2010 | Krivoruchko et al. | 2003/0028242 A1 | 2/2003 | Vallana et al. |
| 7,691,401 B2 | 4/2010 | Castro et al. | 2003/0028243 A1 | 2/2003 | Bates et al. |
| 7,713,297 B2 | 5/2010 | Alt | 2003/0032892 A1 | 2/2003 | Erlach et al. |
| 7,749,264 B2 | 7/2010 | Gregorich et al. | 2003/0033007 A1 | 2/2003 | Sirhan et al. |
| 7,758,635 B2 | 7/2010 | Parsonage | 2003/0044446 A1 | 3/2003 | Moro et al. |
| 7,771,773 B2 | 8/2010 | Namavar | 2003/0050687 A1 | 3/2003 | Schwade et al. |
| 7,776,926 B1 | 8/2010 | Claude et al. | 2003/0059640 A1 | 3/2003 | Marton et al. |
| 2001/0001834 A1 | 5/2001 | Palmaz et al. | 2003/0060871 A1 | 3/2003 | Hill et al. |

| | | | | | | |
|---|---|---|---|---|---|---|
| 2003/0060873 A1 | 3/2003 | Gertner et al. | | 2004/0106975 A1 | 6/2004 | Solovay et al. |
| 2003/0064095 A1 | 4/2003 | Martin et al. | | 2004/0106984 A1 | 6/2004 | Stinson |
| 2003/0068355 A1 | 4/2003 | Shanley et al. | | 2004/0106985 A1 | 6/2004 | Jang |
| 2003/0069631 A1 | 4/2003 | Stoll | | 2004/0111150 A1 | 6/2004 | Berg et al. |
| 2003/0074053 A1 | 4/2003 | Palmaz et al. | | 2004/0116999 A1 | 6/2004 | Ledergerber |
| 2003/0077200 A1 | 4/2003 | Craig et al. | | 2004/0117005 A1 | 6/2004 | Gadde et al. |
| 2003/0077310 A1 | 4/2003 | Pathak et al. | | 2004/0117008 A1 | 6/2004 | Wnendt et al. |
| 2003/0083614 A1 | 5/2003 | Eisert | | 2004/0122504 A1 | 6/2004 | Hogendijk |
| 2003/0083646 A1 | 5/2003 | Sirhan et al. | | 2004/0126566 A1 | 7/2004 | Axen et al. |
| 2003/0083731 A1 | 5/2003 | Kramer et al. | | 2004/0133270 A1 | 7/2004 | Grandt |
| 2003/0087024 A1 | 5/2003 | Flanagan | | 2004/0134886 A1 | 7/2004 | Wagner et al. |
| 2003/0088307 A1 | 5/2003 | Shulze et al. | | 2004/0137039 A1 | 7/2004 | Sukhishvili et al. |
| 2003/0088312 A1 | 5/2003 | Kopia et al. | | 2004/0138738 A1 | 7/2004 | Stinson |
| 2003/0099684 A1 | 5/2003 | Domb | | 2004/0142014 A1 | 7/2004 | Litvack et al. |
| 2003/0100815 A1 | 5/2003 | Da Silva et al. | | 2004/0143317 A1 | 7/2004 | Stinson et al. |
| 2003/0100830 A1 | 5/2003 | Zhong et al. | | 2004/0143321 A1 | 7/2004 | Litvack et al. |
| 2003/0104030 A1 | 6/2003 | Igaki et al. | | 2004/0148010 A1 | 7/2004 | Rush |
| 2003/0105511 A1 | 6/2003 | Welsh et al. | | 2004/0148015 A1 | 7/2004 | Lye et al. |
| 2003/0108659 A1 | 6/2003 | Bales et al. | | 2004/0153138 A1 | 8/2004 | Murphy |
| 2003/0114917 A1 | 6/2003 | Holloway et al. | | 2004/0157073 A1 | 8/2004 | Burrell et al. |
| 2003/0114921 A1 | 6/2003 | Yoon | | 2004/0158308 A1 | 8/2004 | Hogendijk et al. |
| 2003/0118692 A1 | 6/2003 | Wang et al. | | 2004/0158310 A1 | 8/2004 | Weber et al. |
| 2003/0120339 A1 | 6/2003 | Banik et al. | | 2004/0167572 A1 | 8/2004 | Roth et al. |
| 2003/0124055 A1 | 7/2003 | Li et al. | | 2004/0167612 A1 | 8/2004 | Grignani et al. |
| 2003/0125803 A1 | 7/2003 | Vallana | | 2004/0172124 A1 | 9/2004 | Vallana et al. |
| 2003/0130718 A1 | 7/2003 | Palmas et al. | | 2004/0181252 A1 | 9/2004 | Boyle et al. |
| 2003/0139799 A1 | 7/2003 | Ley et al. | | 2004/0181275 A1 | 9/2004 | Noble et al. |
| 2003/0143330 A1 | 7/2003 | Loomis et al. | | 2004/0181276 A1 | 9/2004 | Brown et al. |
| 2003/0144728 A1 | 7/2003 | Scheuermann et al. | | 2004/0181278 A1 | 9/2004 | Tseng et al. |
| 2003/0150380 A1 | 8/2003 | Yoe | | 2004/0182511 A1 | 9/2004 | Rakos et al. |
| 2003/0153901 A1 | 8/2003 | Herweck et al. | | 2004/0186553 A1 | 9/2004 | Yan |
| 2003/0158598 A1 | 8/2003 | Ashton et al. | | 2004/0191293 A1 | 9/2004 | Claude |
| 2003/0170605 A1 | 9/2003 | Long et al. | | 2004/0191404 A1 | 9/2004 | Hossainy et al. |
| 2003/0181975 A1 | 9/2003 | Ishii et al. | | 2004/0202692 A1 | 10/2004 | Shanley et al. |
| 2003/0185895 A1 | 10/2003 | Lanphere | | 2004/0204750 A1 | 10/2004 | Dinh |
| 2003/0190406 A1 | 10/2003 | Hossainy et al. | | 2004/0211362 A1 | 10/2004 | Castro et al. |
| 2003/0195613 A1 | 10/2003 | Curcio et al. | | 2004/0219214 A1 | 11/2004 | Gravett et al. |
| 2003/0204239 A1 | 10/2003 | Carlyle et al. | | 2004/0220510 A1 | 11/2004 | Koullick et al. |
| 2003/0211135 A1 | 11/2003 | Greenhalgh et al. | | 2004/0220659 A1 | 11/2004 | Girton |
| 2003/0216803 A1 | 11/2003 | Ledergerber | | 2004/0220660 A1 | 11/2004 | Shanley et al. |
| 2003/0219562 A1 | 11/2003 | Rypacek et al. | | 2004/0220662 A1 | 11/2004 | Dang et al. |
| 2003/0221307 A1 | 12/2003 | Kaese et al. | | 2004/0224001 A1 | 11/2004 | Pacetti et al. |
| 2003/0228523 A1 | 12/2003 | DeLongchamp et al. | | 2004/0225346 A1 | 11/2004 | Mazumder et al. |
| 2003/0236513 A1 | 12/2003 | Schwarz et al. | | 2004/0228905 A1 | 11/2004 | Greenspan et al. |
| 2004/0000046 A1 | 1/2004 | Stinson | | 2004/0230176 A1 | 11/2004 | Shanahan et al. |
| 2004/0000540 A1 | 1/2004 | Soboyejo et al. | | 2004/0230225 A1 | 11/2004 | Penner et al. |
| 2004/0004063 A1 | 1/2004 | Merdan | | 2004/0230290 A1 | 11/2004 | Weber et al. |
| 2004/0006382 A1 | 1/2004 | Sohier | | 2004/0230293 A1 | 11/2004 | Yip et al. |
| 2004/0018296 A1 | 1/2004 | Castro et al. | | 2004/0234737 A1 | 11/2004 | Pacetti |
| 2004/0019376 A1 | 1/2004 | Alt | | 2004/0236415 A1 | 11/2004 | Thomas |
| 2004/0022939 A1 | 2/2004 | Kim et al. | | 2004/0236416 A1 | 11/2004 | Falotico |
| 2004/0024448 A1* | 2/2004 | Chang et al. ............... 623/1.42 | | 2004/0237282 A1 | 12/2004 | Hines |
| 2004/0029303 A1 | 2/2004 | Hart et al. | | 2004/0242106 A1 | 12/2004 | Rabasco et al. |
| 2004/0030218 A1 | 2/2004 | Kocur et al. | | 2004/0243217 A1 | 12/2004 | Andersen |
| 2004/0030377 A1 | 2/2004 | Dubson et al. | | 2004/0243237 A1 | 12/2004 | Unwin et al. |
| 2004/0034409 A1 | 2/2004 | Heublein et al. | | 2004/0243241 A1 | 12/2004 | Istephanous et al. |
| 2004/0039438 A1 | 2/2004 | Alt | | 2004/0247671 A1 | 12/2004 | Prescott et al. |
| 2004/0039441 A1 | 2/2004 | Rowland et al. | | 2004/0249440 A1 | 12/2004 | Bucker et al. |
| 2004/0044397 A1 | 3/2004 | Stinson | | 2004/0249443 A1 | 12/2004 | Shanley et al. |
| 2004/0047980 A1 | 3/2004 | Pacetti et al. | | 2004/0249444 A1 | 12/2004 | Reiss |
| 2004/0059407 A1 | 3/2004 | Escamilla et al. | | 2004/0249445 A1 | 12/2004 | Rosenthal et al. |
| 2004/0059409 A1 | 3/2004 | Stenzel | | 2004/0249449 A1 | 12/2004 | Shanley et al. |
| 2004/0067301 A1 | 4/2004 | Ding | | 2004/0254419 A1 | 12/2004 | Wang et al. |
| 2004/0071861 A1 | 4/2004 | Mandrusov et al. | | 2004/0254635 A1 | 12/2004 | Shanley et al. |
| 2004/0073155 A1 | 4/2004 | Laufer et al. | | 2005/0004661 A1 | 1/2005 | Lewis et al. |
| 2004/0073284 A1 | 4/2004 | Bates et al. | | 2005/0010275 A1 | 1/2005 | Sahatjian |
| 2004/0073293 A1 | 4/2004 | Thompson | | 2005/0010279 A1 | 1/2005 | Tenerz et al. |
| 2004/0073297 A1 | 4/2004 | Rohde et al. | | 2005/0015142 A1 | 1/2005 | Austin et al. |
| 2004/0073298 A1 | 4/2004 | Hossainy | | 2005/0019265 A1 | 1/2005 | Hammer et al. |
| 2004/0078071 A1 | 4/2004 | Escamilla et al. | | 2005/0019371 A1 | 1/2005 | Anderson et al. |
| 2004/0082682 A1 | 4/2004 | Loomis et al. | | 2005/0021127 A1 | 1/2005 | Kawula |
| 2004/0088038 A1* | 5/2004 | Dehnad et al. ............... 623/1.15 | | 2005/0021128 A1 | 1/2005 | Nakahama et al. |
| 2004/0088041 A1 | 5/2004 | Stanford | | 2005/0022627 A1 | 2/2005 | Chen |
| 2004/0093071 A1 | 5/2004 | Jang | | 2005/0027350 A1 | 2/2005 | Momma et al. |
| 2004/0093075 A1 | 5/2004 | Kuehne | | 2005/0033407 A1 | 2/2005 | Weber et al. |
| 2004/0093076 A1 | 5/2004 | White et al. | | 2005/0033411 A1 | 2/2005 | Wu et al. |
| 2004/0098089 A1 | 5/2004 | Weber | | 2005/0033412 A1 | 2/2005 | Wu et al. |
| 2004/0098108 A1 | 5/2004 | Harder et al. | | 2005/0033417 A1 | 2/2005 | Borges et al. |
| 2004/0098119 A1 | 5/2004 | Wang | | 2005/0037047 A1 | 2/2005 | Song |

| | | | | | | |
|---|---|---|---|---|---|---|
| 2005/0037050 A1 | 2/2005 | Weber | | 2005/0220853 A1 | 10/2005 | Dao et al. |
| 2005/0038134 A1 | 2/2005 | Loomis et al. | | 2005/0221072 A1 | 10/2005 | Dubrow et al. |
| 2005/0038501 A1 | 2/2005 | Moore, Jr. et al. | | 2005/0222671 A1 | 10/2005 | Schaeffer et al. |
| 2005/0042288 A1 | 2/2005 | Koblish et al. | | 2005/0228477 A1 | 10/2005 | Grainger et al. |
| 2005/0042440 A1 | 2/2005 | Bach et al. | | 2005/0228483 A1 | 10/2005 | Kaplan et al. |
| 2005/0055044 A1 | 3/2005 | Kangas | | 2005/0228491 A1 | 10/2005 | Snyder et al. |
| 2005/0055080 A1 | 3/2005 | Istephanous et al. | | 2005/0232968 A1 | 10/2005 | Palmaz et al. |
| 2005/0055085 A1 | 3/2005 | Rivron et al. | | 2005/0233965 A1 | 10/2005 | Schwartz et al. |
| 2005/0060020 A1 | 3/2005 | Jenson | | 2005/0234538 A1 | 10/2005 | Litvack et al. |
| 2005/0060021 A1 | 3/2005 | O'Brien et al. | | 2005/0244459 A1 | 11/2005 | DeWitt et al. |
| 2005/0064088 A1 | 3/2005 | Fredrickson | | 2005/0251245 A1 | 11/2005 | Sieradzki et al. |
| 2005/0069630 A1 | 3/2005 | Fox et al. | | 2005/0251249 A1 | 11/2005 | Sahatjian |
| 2005/0070989 A1 | 3/2005 | Lye et al. | | 2005/0252893 A1 | 11/2005 | Shapovalov et al. |
| 2005/0070990 A1 | 3/2005 | Stinson | | 2005/0255707 A1 | 11/2005 | Hart et al. |
| 2005/0070996 A1 | 3/2005 | Dinh et al. | | 2005/0261760 A1 | 11/2005 | Weber |
| 2005/0071016 A1 | 3/2005 | Hausdorf et al. | | 2005/0266039 A1 | 12/2005 | Weber |
| 2005/0072544 A1 | 4/2005 | Palmaz et al. | | 2005/0266040 A1 | 12/2005 | Gerberding |
| 2005/0074479 A1 | 4/2005 | Weber et al. | | 2005/0266041 A1 | 12/2005 | Gerold et al. |
| 2005/0074545 A1 | 4/2005 | Thomas | | 2005/0267560 A1 | 12/2005 | Bates et al. |
| 2005/0075714 A1 | 4/2005 | Cheng et al. | | 2005/0267561 A1 | 12/2005 | Jones et al. |
| 2005/0077305 A1 | 4/2005 | Guevara | | 2005/0271703 A1 | 12/2005 | Anderson et al. |
| 2005/0079132 A1 | 4/2005 | Wang et al. | | 2005/0271706 A1 | 12/2005 | Anderson et al. |
| 2005/0079199 A1 | 4/2005 | Heruth et al. | | 2005/0276837 A1 | 12/2005 | Anderson et al. |
| 2005/0079356 A1 | 4/2005 | Rathenow et al. | | 2005/0278016 A1 | 12/2005 | Welsh et al. |
| 2005/0092615 A1 | 5/2005 | Birdsall et al. | | 2005/0278021 A1 | 12/2005 | Bates et al. |
| 2005/0096731 A1 | 5/2005 | Looi et al. | | 2005/0281863 A1 | 12/2005 | Anderson et al. |
| 2005/0100577 A1 | 5/2005 | Parker et al. | | 2005/0283224 A1 | 12/2005 | King |
| 2005/0100609 A1 | 5/2005 | Claude | | 2005/0283229 A1* | 12/2005 | Dugan et al. ................. 623/1.38 |
| 2005/0102025 A1 | 5/2005 | Laroche et al. | | 2005/0287188 A1 | 12/2005 | Anderson et al. |
| 2005/0106212 A1 | 5/2005 | Gertner et al. | | 2006/0002979 A1 | 1/2006 | Ashammakhi et al. |
| 2005/0107869 A1 | 5/2005 | Sirhan et al. | | 2006/0009839 A1 | 1/2006 | Tan |
| 2005/0107870 A1 | 5/2005 | Wang et al. | | 2006/0013850 A1 | 1/2006 | Domb |
| 2005/0113936 A1 | 5/2005 | Brustad et al. | | 2006/0014039 A1 | 1/2006 | Zhang et al. |
| 2005/0119723 A1 | 6/2005 | Peacock | | 2006/0015175 A1 | 1/2006 | Palmaz et al. |
| 2005/0129727 A1 | 6/2005 | Weber et al. | | 2006/0015361 A1 | 1/2006 | Sattler et al. |
| 2005/0129731 A1 | 6/2005 | Horres et al. | | 2006/0020742 A1 | 1/2006 | Au et al. |
| 2005/0131509 A1 | 6/2005 | Atanassoska et al. | | 2006/0025848 A1 | 2/2006 | Weber et al. |
| 2005/0131521 A1 | 6/2005 | Marton | | 2006/0035026 A1 | 2/2006 | Atanassoska et al. |
| 2005/0131522 A1 | 6/2005 | Stinson et al. | | 2006/0036281 A1 | 2/2006 | Patterson et al. |
| 2005/0131527 A1 | 6/2005 | Pathak | | 2006/0036311 A1 | 2/2006 | Nakayama et al. |
| 2005/0131528 A1 | 6/2005 | Buscemi et al. | | 2006/0038027 A1 | 2/2006 | O'Connor et al. |
| 2005/0136090 A1 | 6/2005 | Falotico et al. | | 2006/0040388 A1 | 2/2006 | Bromberg et al. |
| 2005/0137677 A1 | 6/2005 | Rush | | 2006/0041182 A1 | 2/2006 | Forbes et al. |
| 2005/0137679 A1 | 6/2005 | Changelian et al. | | 2006/0051397 A1 | 3/2006 | Maier et al. |
| 2005/0137684 A1 | 6/2005 | Changelian et al. | | 2006/0052744 A1 | 3/2006 | Weber |
| 2005/0149169 A1 | 7/2005 | Wang et al. | | 2006/0052863 A1 | 3/2006 | Harder et al. |
| 2005/0149170 A1 | 7/2005 | Tassel et al. | | 2006/0052864 A1 | 3/2006 | Harder et al. |
| 2005/0149175 A1 | 7/2005 | Hunter et al. | | 2006/0058868 A1 | 3/2006 | Gale et al. |
| 2005/0149177 A1 | 7/2005 | Weber et al. | | 2006/0062820 A1 | 3/2006 | Gertner et al. |
| 2005/0159804 A1 | 7/2005 | Lad et al. | | 2006/0064160 A1 | 3/2006 | Gerold et al. |
| 2005/0159805 A1 | 7/2005 | Weber et al. | | 2006/0067908 A1 | 3/2006 | Ding |
| 2005/0159809 A1 | 7/2005 | Hezi-Yamit et al. | | 2006/0069427 A1 | 3/2006 | Savage et al. |
| 2005/0160600 A1 | 7/2005 | Bien et al. | | 2006/0075044 A1 | 4/2006 | Fox et al. |
| 2005/0163821 A1 | 7/2005 | Sung et al. | | 2006/0075092 A1 | 4/2006 | Kidokoro |
| 2005/0163954 A1 | 7/2005 | Shaw | | 2006/0079958 A1 | 4/2006 | Stratford et al. |
| 2005/0165301 A1 | 7/2005 | Smith et al. | | 2006/0085062 A1 | 4/2006 | Lee et al. |
| 2005/0165468 A1 | 7/2005 | Marton | | 2006/0085065 A1 | 4/2006 | Krause et al. |
| 2005/0165470 A1 | 7/2005 | Weber | | 2006/0088566 A1 | 4/2006 | Parsonage et al. |
| 2005/0169969 A1 | 8/2005 | Li et al. | | 2006/0088567 A1 | 4/2006 | Warner et al. |
| 2005/0171595 A1 | 8/2005 | Feldman et al. | | 2006/0088653 A1 | 4/2006 | Chappa et al. |
| 2005/0177226 A1 | 8/2005 | Banik et al. | | 2006/0088666 A1 | 4/2006 | Kobrin et al. |
| 2005/0180919 A1 | 8/2005 | Tedeschi | | 2006/0100696 A1 | 5/2006 | Atanasoska et al. |
| 2005/0182361 A1 | 8/2005 | Lennox | | 2006/0115512 A1 | 6/2006 | Peacock et al. |
| 2005/0182478 A1 | 8/2005 | Holman et al. | | 2006/0118236 A1 | 6/2006 | House et al. |
| 2005/0186250 A1 | 8/2005 | Gertner et al. | | 2006/0121080 A1 | 6/2006 | Lye et al. |
| 2005/0187605 A1 | 8/2005 | Greenhalgh et al. | | 2006/0122694 A1 | 6/2006 | Stinson et al. |
| 2005/0187611 A1 | 8/2005 | Ding et al. | | 2006/0122697 A1 | 6/2006 | Shanley et al. |
| 2005/0192657 A1 | 9/2005 | Colen et al. | | 2006/0124472 A1 | 6/2006 | Rokicki |
| 2005/0192662 A1 | 9/2005 | Ward | | 2006/0127266 A1 | 6/2006 | Miura et al. |
| 2005/0192664 A1 | 9/2005 | Eisert | | 2006/0129215 A1 | 6/2006 | Helmus et al. |
| 2005/0196424 A1 | 9/2005 | Chappa | | 2006/0129222 A1 | 6/2006 | Stinson |
| 2005/0208098 A1 | 9/2005 | Castro et al. | | 2006/0129225 A1 | 6/2006 | Kopia et al. |
| 2005/0208100 A1 | 9/2005 | Weber et al. | | 2006/0136048 A1 | 6/2006 | Pacetti et al. |
| 2005/0209680 A1* | 9/2005 | Gale et al. .................... 623/1.15 | | 2006/0136051 A1 | 6/2006 | Furst et al. |
| 2005/0209681 A1 | 9/2005 | Curcio et al. | | 2006/0141156 A1 | 6/2006 | Viel et al. |
| 2005/0211680 A1 | 9/2005 | Li et al. | | 2006/0149352 A1 | 7/2006 | Schlum |
| 2005/0214951 A1 | 9/2005 | Nahm et al. | | 2006/0153729 A1 | 7/2006 | Stinson et al. |
| 2005/0216074 A1 | 9/2005 | Sahatjian | | 2006/0155361 A1 | 7/2006 | Schomig et al. |
| 2005/0216075 A1 | 9/2005 | Wang et al. | | 2006/0167543 A1 | 7/2006 | Bailey et al. |

| | | | | | | |
|---|---|---|---|---|---|---|
| 2006/0177480 A1 | 8/2006 | Sung et al. | | 2007/0141106 A1 | 6/2007 | Bonutti et al. |
| 2006/0178727 A1 | 8/2006 | Richter | | 2007/0142897 A1 | 6/2007 | Consigny et al. |
| 2006/0184235 A1 | 8/2006 | Rivron et al. | | 2007/0142899 A1 | 6/2007 | Lootz et al. |
| 2006/0193886 A1 | 8/2006 | Owens et al. | | 2007/0148251 A1 | 6/2007 | Hossainy et al. |
| 2006/0193887 A1 | 8/2006 | Owens et al. | | 2007/0151093 A1 | 7/2007 | Curcio et al. |
| 2006/0193888 A1 | 8/2006 | Lye et al. | | 2007/0156231 A1 | 7/2007 | Weber |
| 2006/0193889 A1 | 8/2006 | Spradlin et al. | | 2007/0156248 A1 | 7/2007 | Marco et al. |
| 2006/0193890 A1 | 8/2006 | Owens et al. | | 2007/0160641 A1 | 7/2007 | Jang |
| 2006/0193892 A1 | 8/2006 | Furst et al. | | 2007/0168016 A1 | 7/2007 | Gronemeyer et al. |
| 2006/0195142 A1 | 8/2006 | Shalaby | | 2007/0173923 A1 | 7/2007 | Savage et al. |
| 2006/0198869 A1 | 9/2006 | Furst et al. | | 2007/0178129 A1 | 8/2007 | Flanagan |
| 2006/0199876 A1 | 9/2006 | Troczynski et al. | | 2007/0181433 A1 | 8/2007 | Birdsall et al. |
| 2006/0200229 A1 | 9/2006 | Burgermeister et al. | | 2007/0184083 A1 | 8/2007 | Coughlin |
| 2006/0200231 A1 | 9/2006 | O'Brien et al. | | 2007/0190104 A1 | 8/2007 | Kamath et al. |
| 2006/0200232 A1 | 9/2006 | Phaneuf et al. | | 2007/0191923 A1 | 8/2007 | Weber |
| 2006/0200233 A1 | 9/2006 | Kujawski | | 2007/0191928 A1 | 8/2007 | Rolando et al. |
| 2006/0204441 A1 | 9/2006 | Atala et al. | | 2007/0191931 A1 | 8/2007 | Weber et al. |
| 2006/0204445 A1 | 9/2006 | Atala et al. | | 2007/0191943 A1 | 8/2007 | Shrivastava et al. |
| 2006/0210595 A1 | 9/2006 | Singhvi et al. | | 2007/0197980 A1 | 8/2007 | Barry et al. |
| 2006/0212108 A1 | 9/2006 | Tittelbach | | 2007/0202466 A1 | 8/2007 | Schwarz et al. |
| 2006/0222679 A1 | 10/2006 | Shanley et al. | | 2007/0207186 A1 | 9/2007 | Scanlon et al. |
| 2006/0222844 A1 | 10/2006 | Stinson | | 2007/0208412 A1 | 9/2007 | Elmaleh |
| 2006/0224237 A1 | 10/2006 | Furst et al. | | 2007/0219626 A1 | 9/2007 | Rolando et al. |
| 2006/0229711 A1 | 10/2006 | Yan et al. | | 2007/0224116 A1 | 9/2007 | Chandrasekaran et al. |
| 2006/0229713 A1 | 10/2006 | Shanley et al. | | 2007/0224244 A1 | 9/2007 | Weber et al. |
| 2006/0230476 A1 | 10/2006 | Atanasoska et al. | | 2007/0225799 A1 | 9/2007 | Doty |
| 2006/0233941 A1 | 10/2006 | Olson | | 2007/0244541 A1 | 10/2007 | Schulman |
| 2006/0241739 A1 | 10/2006 | Besselink et al. | | 2007/0244569 A1 | 10/2007 | Weber et al. |
| 2006/0251701 A1 | 11/2006 | Lynn et al. | | 2007/0250155 A1 | 10/2007 | Simpson |
| 2006/0259133 A1 | 11/2006 | Sowinski et al. | | 2007/0250156 A1 | 10/2007 | Palmaz |
| 2006/0264138 A1 | 11/2006 | Sowinski et al. | | 2007/0250158 A1 | 10/2007 | Krivoruchko et al. |
| 2006/0271156 A1 | 11/2006 | Ledergerber | | 2007/0255388 A1 | 11/2007 | Rudakov et al. |
| 2006/0271168 A1 * | 11/2006 | Kleine et al. ............... 623/1.38 | | 2007/0255392 A1 | 11/2007 | Johnson |
| 2006/0271169 A1 | 11/2006 | Lye et al. | | 2007/0264199 A1 | 11/2007 | Labhasetwar et al. |
| 2006/0271192 A1 | 11/2006 | Olsen et al. | | 2007/0264303 A1 | 11/2007 | Atanasoska et al. |
| 2006/0275554 A1 | 12/2006 | Zhao et al. | | 2007/0270940 A1 | 11/2007 | Doty |
| 2006/0276877 A1 | 12/2006 | Owens et al. | | 2007/0270942 A1 | 11/2007 | Thomas |
| 2006/0276878 A1 | 12/2006 | Owens et al. | | 2007/0281073 A1 | 12/2007 | Gale et al. |
| 2006/0276879 A1 | 12/2006 | Lye et al. | | 2007/0281117 A1 | 12/2007 | Kaplan et al. |
| 2006/0276884 A1 | 12/2006 | Lye et al. | | 2007/0282432 A1 * | 12/2007 | Stinson et al. ............... 623/1.38 |
| 2006/0276885 A1 | 12/2006 | Lye et al. | | 2007/0299509 A1 | 12/2007 | Ding |
| 2006/0280770 A1 | 12/2006 | Hossainy et al. | | 2007/0299512 A1 | 12/2007 | Korzuschnik et al. |
| 2006/0287709 A1 | 12/2006 | Rao | | 2008/0003251 A1 | 1/2008 | Zhou |
| 2006/0292388 A1 | 12/2006 | Palumbo et al. | | 2008/0003256 A1 | 1/2008 | Martens et al. |
| 2007/0003589 A1 | 1/2007 | Astafieva et al. | | 2008/0003431 A1 | 1/2008 | Fellinger et al. |
| 2007/0003596 A1 | 1/2007 | Tittelbach et al. | | 2008/0004691 A1 | 1/2008 | Weber et al. |
| 2007/0020306 A1 | 1/2007 | Schultheiss | | 2008/0031765 A1 | 2/2008 | Gerold et al. |
| 2007/0027532 A1 | 2/2007 | Wang et al. | | 2008/0033522 A1 | 2/2008 | Grewe et al. |
| 2007/0032858 A1 | 2/2007 | Santos et al. | | 2008/0033530 A1 | 2/2008 | Zberg et al. |
| 2007/0032862 A1 | 2/2007 | Weber et al. | | 2008/0033531 A1 | 2/2008 | Barthel et al. |
| 2007/0032864 A1 | 2/2007 | Furst et al. | | 2008/0033533 A1 | 2/2008 | Borck |
| 2007/0034615 A1 | 2/2007 | Kleine | | 2008/0033536 A1 * | 2/2008 | Wittchow ............... 623/1.38 |
| 2007/0036905 A1 | 2/2007 | Kramer | | 2008/0033537 A1 | 2/2008 | Tittelbach |
| 2007/0038176 A1 | 2/2007 | Weber et al. | | 2008/0033538 A1 | 2/2008 | Borck et al. |
| 2007/0038289 A1 | 2/2007 | Nishide et al. | | 2008/0033539 A1 | 2/2008 | Sternberg et al. |
| 2007/0038290 A1 | 2/2007 | Huang et al. | | 2008/0033576 A1 | 2/2008 | Gerold et al. |
| 2007/0045252 A1 | 3/2007 | Kleine et al. | | 2008/0038146 A1 | 2/2008 | Wachter et al. |
| 2007/0048350 A1 * | 3/2007 | Falotico et al. ............... 424/423 | | 2008/0050413 A1 | 2/2008 | Horvers et al. |
| 2007/0050007 A1 | 3/2007 | Kondyurin et al. | | 2008/0051335 A1 | 2/2008 | Kleiner et al. |
| 2007/0050009 A1 | 3/2007 | Flanagan | | 2008/0051866 A1 | 2/2008 | Chen et al. |
| 2007/0052497 A1 | 3/2007 | Tada | | 2008/0051872 A1 | 2/2008 | Borck |
| 2007/0055349 A1 | 3/2007 | Santos et al. | | 2008/0051881 A1 | 2/2008 | Feng et al. |
| 2007/0055354 A1 | 3/2007 | Santos et al. | | 2008/0057105 A1 | 3/2008 | Atanasoska et al. |
| 2007/0055364 A1 | 3/2007 | Hossainy et al. | | 2008/0058919 A1 | 3/2008 | Kramer-Brown et al. |
| 2007/0059435 A1 | 3/2007 | Santos et al. | | 2008/0058921 A1 | 3/2008 | Lindquist |
| 2007/0065418 A1 | 3/2007 | Vallana et al. | | 2008/0058923 A1 | 3/2008 | Bertsch et al. |
| 2007/0073385 A1 | 3/2007 | Schaeffer et al. | | 2008/0069854 A1 | 3/2008 | Xiao et al. |
| 2007/0073390 A1 | 3/2007 | Lee | | 2008/0069858 A1 | 3/2008 | Weber |
| 2007/0077163 A1 | 4/2007 | Furst et al. | | 2008/0071348 A1 | 3/2008 | Boismier et al. |
| 2007/0100385 A1 | 5/2007 | Rawat et al. | | 2008/0071349 A1 | 3/2008 | Atanasoska et al. |
| 2007/0104753 A1 | 5/2007 | Flanagan | | 2008/0071350 A1 | 3/2008 | Stinson |
| 2007/0106347 A1 | 5/2007 | Lin | | 2008/0071351 A1 | 3/2008 | Flanagan et al. |
| 2007/0106363 A1 | 5/2007 | Weber | | 2008/0071352 A1 | 3/2008 | Weber et al. |
| 2007/0123131 A1 | 5/2007 | Nguyen et al. | | 2008/0071353 A1 | 3/2008 | Weber et al. |
| 2007/0123973 A1 | 5/2007 | Roth et al. | | 2008/0071355 A1 * | 3/2008 | Weber et al. ............... 623/1.16 |
| 2007/0129789 A1 | 6/2007 | Cottone, Jr. et al. | | 2008/0071357 A1 | 3/2008 | Girton et al. |
| 2007/0129792 A1 | 6/2007 | Picart et al. | | 2008/0071358 A1 | 3/2008 | Weber et al. |
| 2007/0134288 A1 | 6/2007 | Parsonage et al. | | 2008/0082162 A1 | 4/2008 | Boismier et al. |
| 2007/0135908 A1 | 6/2007 | Zhao | | 2008/0086199 A1 | 4/2008 | Dave et al. |

| | | | | | |
|---|---|---|---|---|---|
| 2008/0086201 A1 | 4/2008 | Weber et al. | 2009/0076588 A1 | 3/2009 | Weber |
| 2008/0090097 A1 | 4/2008 | Shaw et al. | 2009/0076596 A1 | 3/2009 | Adden et al. |
| 2008/0097577 A1 | 4/2008 | Atanasoska et al. | 2009/0081293 A1 | 3/2009 | Murase et al. |
| 2008/0103589 A1 | 5/2008 | Cheng et al. | 2009/0081450 A1 | 3/2009 | Ascher et al. |
| 2008/0103594 A1 | 5/2008 | Loffler et al. | 2009/0088831 A1 | 4/2009 | Goto |
| 2008/0107890 A1 | 5/2008 | Bureau et al. | 2009/0088834 A1 | 4/2009 | Wang |
| 2008/0109072 A1 | 5/2008 | Girton | 2009/0093871 A1 | 4/2009 | Rea et al. |
| 2008/0113083 A1 | 5/2008 | Sutermeister et al. | 2009/0095715 A1 | 4/2009 | Sabaria |
| 2008/0124373 A1 | 5/2008 | Xiao et al. | 2009/0118809 A1 | 5/2009 | Scheuermann et al. |
| 2008/0131479 A1 | 6/2008 | Weber et al. | 2009/0118812 A1 | 5/2009 | Kokate et al. |
| 2008/0140172 A1 | 6/2008 | Carpenter et al. | 2009/0118813 A1 | 5/2009 | Scheuermann et al. |
| 2008/0140186 A1 | 6/2008 | Grignani et al. | 2009/0118814 A1 | 5/2009 | Schoenle et al. |
| 2008/0145400 A1 | 6/2008 | Weber et al. | 2009/0118815 A1 | 5/2009 | Arcand et al. |
| 2008/0147175 A1 | 6/2008 | Krivoruchko et al. | 2009/0118818 A1 | 5/2009 | Foss et al. |
| 2008/0147177 A1 | 6/2008 | Scheuermann et al. | 2009/0118819 A1 | 5/2009 | Merz et al. |
| 2008/0148002 A1 | 6/2008 | Fleming | 2009/0118820 A1 | 5/2009 | Gregorich et al. |
| 2008/0152929 A1 | 6/2008 | Zhao | 2009/0118821 A1 | 5/2009 | Scheuermann et al. |
| 2008/0160166 A1 | 7/2008 | Rypacek et al. | 2009/0118822 A1 | 5/2009 | Holman et al. |
| 2008/0160259 A1 | 7/2008 | Nielson et al. | 2009/0118823 A1 | 5/2009 | Atanasoska et al. |
| 2008/0161906 A1 | 7/2008 | Atanasoska et al. | 2009/0123517 A1 | 5/2009 | Flanagan et al. |
| 2008/0171929 A1 | 7/2008 | Katims | 2009/0123521 A1 | 5/2009 | Weber et al. |
| 2008/0175885 A1 | 7/2008 | Asgari | 2009/0124956 A1 | 5/2009 | Swetlin et al. |
| 2008/0177378 A1 | 7/2008 | Asgari | 2009/0131540 A1 | 5/2009 | Hiromoto et al. |
| 2008/0183269 A2 | 7/2008 | Kaplan et al. | 2009/0143855 A1 | 6/2009 | Weber et al. |
| 2008/0183277 A1 | 7/2008 | Atanasoska et al. | 2009/0149942 A1 | 6/2009 | Edelman et al. |
| 2008/0183278 A1 | 7/2008 | Atanasoska et al. | 2009/0157165 A1 | 6/2009 | Miller et al. |
| 2008/0188927 A1 | 8/2008 | Rohde et al. | 2009/0157172 A1 | 6/2009 | Kokate et al. |
| 2008/0195170 A1 | 8/2008 | Asgari | 2009/0164002 A1 | 6/2009 | Becher et al. |
| 2008/0195189 A1 | 8/2008 | Asgari | 2009/0171452 A1 | 7/2009 | Yamamoto et al. |
| 2008/0195198 A1 | 8/2008 | Asgari | 2009/0177273 A1 | 7/2009 | Piveteau et al. |
| 2008/0208308 A1 | 8/2008 | Allen et al. | 2009/0182290 A1 | 7/2009 | Harder et al. |
| 2008/0208313 A1 | 8/2008 | Yu et al. | 2009/0182337 A1 | 7/2009 | Stopek et al. |
| 2008/0208352 A1 | 8/2008 | Krivoruchko et al. | 2009/0182425 A1 | 7/2009 | Duda et al. |
| 2008/0213377 A1 | 9/2008 | Bhatia et al. | 2009/0192571 A1 | 7/2009 | Stett et al. |
| 2008/0215129 A1 | 9/2008 | Venturelli et al. | 2009/0192594 A1 | 7/2009 | Borck |
| 2008/0215139 A1* | 9/2008 | McMorrow et al. ......... 623/1.43 | 2009/0192595 A1 | 7/2009 | Nagura et al. |
| 2008/0215140 A1 | 9/2008 | Borck et al. | 2009/0192596 A1 | 7/2009 | Adden |
| 2008/0241218 A1 | 10/2008 | McMorrow et al. | 2009/0196899 A1 | 8/2009 | Birdsall et al. |
| 2008/0243113 A1 | 10/2008 | Shastri et al. | 2009/0198320 A1 | 8/2009 | Mueller et al. |
| 2008/0243230 A1 | 10/2008 | Lootz et al. | 2009/0202610 A1 | 8/2009 | Wilson |
| 2008/0243231 A1 | 10/2008 | Flanagan et al. | 2009/0204203 A1 | 8/2009 | Allen et al. |
| 2008/0243234 A1 | 10/2008 | Wilcox | 2009/0208428 A1 | 8/2009 | Hill et al. |
| 2008/0243240 A1 | 10/2008 | Doty et al. | 2009/0208555 A1 | 8/2009 | Kuttler et al. |
| 2008/0243242 A1 | 10/2008 | Kappelt et al. | 2009/0214373 A1 | 8/2009 | Stinson et al. |
| 2008/0249600 A1 | 10/2008 | Atanasoska et al. | 2009/0220612 A1 | 9/2009 | Perera |
| 2008/0249615 A1 | 10/2008 | Weber | 2009/0228037 A1 | 9/2009 | Rego |
| 2008/0255508 A1 | 10/2008 | Wang | 2009/0240323 A1 | 9/2009 | Wilcox |
| 2008/0255509 A1 | 10/2008 | Wang | 2009/0254171 A1 | 10/2009 | Heikkila |
| 2008/0262589 A1 | 10/2008 | Nagura | 2009/0259300 A1 | 10/2009 | Dorogy, Jr. et al. |
| 2008/0268308 A1 | 10/2008 | Schilling et al. | 2009/0270979 A1 | 10/2009 | Adden |
| 2008/0269872 A1 | 10/2008 | Lootz et al. | 2009/0274737 A1 | 11/2009 | Borck |
| 2008/0288048 A1 | 11/2008 | Rolando et al. | 2009/0281613 A1 | 11/2009 | Atanasoska et al. |
| 2008/0290467 A1 | 11/2008 | Shue | 2009/0287301 A1 | 11/2009 | Weber |
| 2008/0294236 A1 | 11/2008 | Anand et al. | 2009/0287302 A1 | 11/2009 | Thomas et al. |
| 2008/0294246 A1 | 11/2008 | Scheuermann | 2009/0306584 A1 | 12/2009 | Schmidtlein et al. |
| 2008/0306584 A1* | 12/2008 | Kramer-Brown ............ 623/1.39 | 2009/0306756 A1 | 12/2009 | Cho et al. |
| 2009/0005862 A1 | 1/2009 | Nakatani et al. | 2009/0306765 A1 | 12/2009 | Weber |
| 2009/0012599 A1 | 1/2009 | Broome et al. | 2009/0306766 A1 | 12/2009 | McDermott et al. |
| 2009/0018639 A1 | 1/2009 | Kuehling | 2009/0311300 A1 | 12/2009 | Wittchow |
| 2009/0018647 A1 | 1/2009 | Benco et al. | 2009/0312807 A1 | 12/2009 | Boudreault et al. |
| 2009/0018648 A1 | 1/2009 | Wittchow | 2009/0319035 A1 | 12/2009 | Terry |
| 2009/0022771 A1 | 1/2009 | Lynn et al. | 2009/0324684 A1 | 12/2009 | Atanasoska et al. |
| 2009/0024199 A1 | 1/2009 | Birdsall et al. | 2009/0326638 A1 | 12/2009 | Atanasoska et al. |
| 2009/0024209 A1 | 1/2009 | Ozdil et al. | 2010/0008970 A1 | 1/2010 | O'Brien et al. |
| 2009/0024210 A1 | 1/2009 | Klocke et al. | 2010/0010621 A1 | 1/2010 | Klocke |
| 2009/0024211 A1 | 1/2009 | Wittchow | 2010/0010640 A1 | 1/2010 | Gerold et al. |
| 2009/0028785 A1 | 1/2009 | Clarke | 2010/0015206 A1 | 1/2010 | Flanagan et al. |
| 2009/0030494 A1 | 1/2009 | Stefanadis et al. | 2010/0016940 A1 | 1/2010 | Shokoohi et al. |
| 2009/0030500 A1 | 1/2009 | Weber et al. | 2010/0021523 A1 | 1/2010 | Scheuermann et al. |
| 2009/0030504 A1 | 1/2009 | Weber et al. | 2010/0023112 A1 | 1/2010 | Borck et al. |
| 2009/0030506 A1 | 1/2009 | Klocke et al. | 2010/0023116 A1 | 1/2010 | Borck et al. |
| 2009/0030507 A1 | 1/2009 | Klocke et al. | 2010/0028436 A1 | 2/2010 | Ohrlander et al. |
| 2009/0035351 A1 | 2/2009 | Berglund et al. | 2010/0030326 A1 | 2/2010 | Radhakrishnan et al. |
| 2009/0043330 A1 | 2/2009 | To | 2010/0034899 A1 | 2/2010 | Harder et al. |
| 2009/0043374 A1 | 2/2009 | Nakano | 2010/0042205 A1 | 2/2010 | Atanasoska et al. |
| 2009/0043380 A1 | 2/2009 | Blaha et al. | 2010/0042206 A1 | 2/2010 | Yadav et al. |
| 2009/0048660 A1 | 2/2009 | Adden | 2010/0047312 A1 | 2/2010 | Wittchow |
| 2009/0062905 A1 | 3/2009 | Moore, Jr. et al. | 2010/0047324 A1 | 2/2010 | Fritz et al. |
| 2009/0069884 A1 | 3/2009 | Mueller | 2010/0049146 A1 | 2/2010 | Nielsen et al. |

| | | |
|---|---|---|
| 2010/0049296 A1 | 2/2010 | Sarasam et al. |
| 2010/0049299 A1 | 2/2010 | Popowski et al. |
| 2010/0049300 A1 | 2/2010 | Harder |
| 2010/0055151 A1 | 3/2010 | Flanagan |
| 2010/0057188 A1 | 3/2010 | Weber |
| 2010/0057197 A1 | 3/2010 | Weber et al. |
| 2010/0070024 A1 | 3/2010 | Venturelli et al. |
| 2010/0075162 A1 | 3/2010 | Yang et al. |
| 2010/0076544 A1 | 3/2010 | Hoffmann et al. |
| 2010/0076556 A1 | 3/2010 | Tomantschger et al. |
| 2010/0081735 A1 | 4/2010 | Mao et al. |
| 2010/0082092 A1 | 4/2010 | Gerold |
| 2010/0087910 A1 | 4/2010 | Weber |
| 2010/0087911 A1 | 4/2010 | Mueller |
| 2010/0087914 A1 | 4/2010 | Bayer et al. |
| 2010/0087915 A1 | 4/2010 | Bayer et al. |
| 2010/0087916 A1 | 4/2010 | Bayer et al. |
| 2010/0092535 A1 | 4/2010 | Cook et al. |
| 2010/0106243 A1 | 4/2010 | Wittchow |
| 2010/0119576 A1 | 5/2010 | Harder et al. |
| 2010/0119581 A1 | 5/2010 | Gratz et al. |
| 2010/0121432 A1 | 5/2010 | Klocke et al. |
| 2010/0125325 A1 | 5/2010 | Allen et al. |
| 2010/0125328 A1 | 5/2010 | Flanagan |
| 2010/0131050 A1 | 5/2010 | Zhao |
| 2010/0131052 A1 | 5/2010 | Kappelt et al. |
| 2010/0161031 A1 | 6/2010 | Papirov et al. |
| 2010/0217370 A1 | 8/2010 | Scheuermann et al. |

FOREIGN PATENT DOCUMENTS

| | | |
|---|---|---|
| AU | 2003 203 722 | 11/2003 |
| CA | 2 235 031 | 10/1998 |
| CA | 2 346 857 | 5/2000 |
| CA | 2 371 800 | 8/2000 |
| DE | 198 11 033 | 8/1999 |
| DE | 198 56 983 | 12/1999 |
| DE | 103 57 281 | 7/2005 |
| DE | 103 61 941 | 7/2005 |
| DE | 10 2006 038236 | 2/2008 |
| EP | 0 006 544 | 6/1979 |
| EP | 0 337 035 | 11/1993 |
| EP | 0 923 389 | 7/1998 |
| EP | 0 966 979 | 12/1999 |
| EP | 0 972 563 | 1/2000 |
| EP | 1 054 644 | 11/2000 |
| EP | 1 071 490 | 1/2001 |
| EP | 1 222 901 | 7/2002 |
| EP | 1 270 023 | 1/2003 |
| EP | 1 273 314 | 1/2003 |
| EP | 1 370 306 | 12/2003 |
| EP | 0 923 912 | 2/2004 |
| EP | 1 389 471 | 2/2004 |
| EP | 1 393 766 | 3/2004 |
| EP | 1 419 793 | 5/2004 |
| EP | 0 951 877 | 6/2004 |
| EP | 1 260 214 | 6/2004 |
| EP | 0 875 218 | 2/2005 |
| EP | 1 733 746 | 12/2006 |
| EP | 1 752 167 | 2/2007 |
| EP | 1 465 552 | 5/2007 |
| EP | 1 835 042 | 9/2007 |
| EP | 1 750 780 | 10/2007 |
| EP | 1 562 565 | 3/2008 |
| EP | 1 642 551 | 12/2008 |
| EP | 1 653 885 | 4/2009 |
| EP | 1 632 256 | 9/2009 |
| EP | 1 703 858 | 10/2009 |
| EP | 2 139 535 | 1/2010 |
| EP | 1 883 380 | 3/2010 |
| EP | 2 189 169 | 5/2010 |
| RU | 2 218 242 | 12/2003 |
| WO | 93/04118 | 3/1993 |
| WO | 97/11724 | 4/1997 |
| WO | 98/29025 | 7/1998 |
| WO | 98/48851 | 11/1998 |
| WO | 99/33410 | 7/1999 |
| WO | 99/47077 | 9/1999 |
| WO | 99/64580 | 12/1999 |
| WO | 00/25841 | 5/2000 |
| WO | 00/48660 | 8/2000 |
| WO | 00/51136 | 8/2000 |
| WO | 00/54704 | 9/2000 |
| WO | 00/66190 | 11/2000 |
| WO | 01/49338 | 7/2001 |
| WO | 01/78906 | 10/2001 |
| WO | 01/80920 | 11/2001 |
| WO | 01/87371 | 11/2001 |
| WO | 02/45764 | 6/2002 |
| WO | 02/47739 | 6/2002 |
| WO | 02/053202 | 7/2002 |
| WO | 03/002243 | 1/2003 |
| WO | 03/013396 | 2/2003 |
| WO | 03/035131 | 5/2003 |
| WO | 03/035134 | 5/2003 |
| WO | 03/035278 | 5/2003 |
| WO | 03/063733 | 8/2003 |
| WO | 03/094990 | 11/2003 |
| WO | 2004/029313 | 4/2004 |
| WO | 2004/043292 | 5/2004 |
| WO | 2004/093643 | 11/2004 |
| WO | 2005/025449 | 3/2005 |
| WO | 2005/065576 | 7/2005 |
| WO | 2005/079335 | 9/2005 |
| WO | 2005/110395 | 11/2005 |
| WO | 2005/118019 | 12/2005 |
| WO | 2006/008739 | 1/2006 |
| WO | 2006/060033 | 6/2006 |
| WO | 2006/060534 | 6/2006 |
| WO | 2006/065356 | 6/2006 |
| WO | 2006/077154 | 7/2006 |
| WO | 2006/080381 | 8/2006 |
| WO | 2006/097503 | 9/2006 |
| WO | 2006/104644 | 10/2006 |
| WO | WO 2006/108065 | 10/2006 |
| WO | 2007/005806 | 1/2007 |
| WO | 2007/013102 | 2/2007 |
| WO | 2007/018931 | 2/2007 |
| WO | 2007/024552 | 3/2007 |
| WO | 2007/035791 | 3/2007 |
| WO | 2007/079363 | 7/2007 |
| WO | 2007/079636 | 7/2007 |
| WO | 2007/082147 | 9/2007 |
| WO | 2007/139668 | 12/2007 |
| WO | 2008/003450 | 3/2008 |
| WO | 2008/036457 | 3/2008 |
| WO | 2008/036548 | 3/2008 |
| WO | 2008/036554 | 3/2008 |
| WO | 2008/62414 | 5/2008 |
| WO | 2008/092436 | 8/2008 |
| WO | 2008/106271 | 9/2008 |
| WO | 2008/117315 | 10/2008 |
| WO | 2008/118606 | 10/2008 |
| WO | 2009/045773 | 4/2009 |

OTHER PUBLICATIONS

Office Action, U.S. Appl. No. 11/856,960 mailed Jun. 9, 2009, 13 pages.
U.S. Appl. No. 10/849,742, filed May 20, 2004, Chen et al.
U.S. Appl. No. 60/826,002, filed Sep. 18, 2006, Girton et al.
U.S. Appl. No. 60/845,136, filed Sep. 15, 2006, Weber and Atanasoska.
U.S. Appl. No. 60/862,318, filed Oct. 20, 2006, Atanasoska et al.
"Best of the ACC Scientific Session 2002," *Rev. Cardiovasc. Med.*, 2002, 3(2):85-104.
"Chapter 2: Corrosion Theory and Corrosion Protection," *EM 1110-2-3400*, 1995, 8 pages.
"Galvanic cell" printout from wikipedia, 5 pages, printed on Aug. 16, 2010.
"*Galvanic corrosion*," http://www.corrosion-doctors.org/aircraft/galvdefi.htm, 3 pgs., printed Oct. 28, 2005.
"Galvanic series" printout from Wikipedia, p. 1 of 2, printed Oct. 28, 2005.
Aaltonen, "Atomic Layer Deposition of Noble Metal Thin Films," *University of Helsinki*, Apr. 8, 2005, pp. 1-71.
Aghion et al., "Newly Developed Magnesium Alloys for Powertrain Applications," *JOM*, 2003, p. 30.

Albion Research Notes, Newsletter, Oct. 1994, 3(4): 1-4.
Anand et al., "Ion-exchange resins: carrying drug delivery forward," *DDT*, 2001, 6: 905-914.
Anderson et al., "A new conductive polymer as a replacement for chrome conversion coatings," *2003 Aerospace Coatings Removel and Coatings Conference*,May 20-22, 2003, Colorado Springs, CO, 7 pages.
Andión et al., "Corrosion behaviour at the interface of steel bars embedded in cement slurries Effect of phenol polymer coatings," *Corrosion Science*, 2002, 44:2805-2816.
Antipov et al., "Polyelectrolyte Multilayer Capsule Permeability Control," *Colloids and Surfaces A: Physiochem. Eng. Aspects*, 2002, 198-200, 535-541.
Antipov et al., "Polyelectrolyte Multilayer Capsules as Vehicles with Tunable Permeability", *Advances in Colloid and Interface Science*, 2004, 111: 49-61.
Arts et al., "Polyphenols and disease risk in epidemiologic studies," *Am. J. Clin. Nutr.*, 2005, 81:317S-325S.
Artyukhin et al., "Layer-by-Layer Electrostatic Self-Assembly of Polyelectrolyte Nanoshells on Individual Carbon Nanotube Templates," *Langmuir*, 2004, 20:1442-1448.
Ashtari et al. "An efficient method for recovery of target ssDNA based on amino-modified silica-coated magnetic nanoparticles" *Talanta 67*. (2005). 548-554.
Atta, "Electrochemical synthesis, characterization and some properties of a polymer derived from thioflavin S.," *European Polymer Journal*, 2005, 41: 3018-3025.
Australian Government, Department of Health and Aging, "Horizon Scanning Technology Prioritising Summary-Biodegradable stents for coronary artery disease," *Australia and New Zealand Horizon Scanning Network (ANZHSN)*, Aug. 2007, pp. 1-13.
Authorized Officer Athina Nickitas-Etienne, International Preliminary Report on Patentability in PCT/US07/78449 mailed Mar. 26, 2009, 9 pages.
Authorized Officer Athina Nickitas-Etienne, International Preliminary Report on Patentability in PCT/US07/79841 mailed Apr. 30, 2009, 7 pages.
Authorized officer Athina Nickitas-Etienne, International Preliminary Report on Patentability in PCT/US08/86639 mailed Jun. 24, 2010, 2 pages.
Authorized Officer Cecilia Giel-Barragán Ramos, International Search Report/Written in PCT/US07/79841 mailed Feb. 4, 2009, 11 pages.
Authorized Officer Elisabeth Reinecke, International Search Report/Written Opinion in PCT/US07/60137 mailed Jul. 27, 2007, 20 pages. (656W01).
Authorized Officer Joëlle Gerber, International Search Report/Written Opinion in PCT/US07/78450 mailed Nov. 19, 2008, 17 pages.
Authorized Officer Joëlle Gerber, International Search Report/Written Opinion in PCT/US07/88888 mailed Jul. 13, 2009, 24 pages.
Authorized Officer Nora Lindner, International Preliminary Report on Patentability in PCT/US07/88888 mailed Jul. 30, 2009, 11 pages.
International Search Report/Written Opinion in PCT/US2008/86639 mailed Feb. 23, 2010, 8 pages.
Authorized Officer Simin Baharlou, International Preliminary Report on Patentability in PCT/US07/66568 mailed Oct. 23, 2008, 10 pages.
Authorized Officer Simin Baharlou, International Preliminary Report on Patentability in PCT/US07/75072 mailed Feb. 12, 2009, 9 pages.
Authorized Officer Trudy Hinterwimmer, International Search Report/Written Opinion in PCT/US07/78412 mailed Mar. 3, 2008, 10 pages.
Authorized Officer Trudy Hinterwimmer, International Search Report/Written Opinion in PCT/US09/49422 mailed Aug. 24, 2009, 10 pages.
Authorized Officer Véronique van Loon-Mégard, International Search Report/Written Opinion in PCT/US08/75976 mailed Nov. 25, 2008, 20 pages.
International Search Report/Written Opinion in PCT/US2009/43326 mailed Aug. 6, 2009, 9 pages.
Babapulle and Eisenberg, "Coatred stents for their prevention of restenosis: Part II," *Circulation*, 2021, 106: 2849-2866.

Bach et al., "Corrosion, Protection and Repassivation After the Deformation of Magnesium Alloys Coated With a Protective Magnesium Fluoride Layer," *JOM*, 2004, p. 343.
Bakkar et al., "Improving corrosion resistance of magnesium-based alloys by surface modification with hydrogen by electrochemical ion reduction (EIR) and by plasma immersion ion implantation (PIII)," *Corrosion Science*, 2005, 47:1211-1225.
Balasubramanian et al. "Dispersion and Stability Studies of Resorcinarene-Encapsulated Gold Nanoparticles." *Langmuir*, 2002, 1676-3681.
Bao, Y. et al. "Preparation of functionalized and gold-coated cobalt nanocrystals for biomedical applications." *Journal of Magnetism and Magnetic Materials*, 2005, 293:15-19.
Baurschmidt et al., "The Electrochemical Aspects of the Thrombogenicity of a Material," *J. Bioengineering*, 1977, 1:261-278.
Bekesi et al., "Efficient Submircon Processing of Metals with Femto," *Appl. Phys. A.*, Oct. 25, 2002, pp. 355-357.
Ben-Hamu et al., "Influence of Si, Ca and Ag addition on corrosion behaviour of new wrought Mg-Zn alloys," *Materials Science and Technology*, 2006, vol. 22, No. 10, pp. 1213-1218.
Bereket et al., "Electrochemical synthesis and anti-corrosive properties of polyaniline, poly(2-anisidine), and poly(aniline-co-2-anisidine) films on stainless steel," *Progress in Organic Coatings*, 2005, 54: 63-72.
Berkland et al., "Controlling Surface Nano-structure Using Flow-Limited Field-Injection Electrostatic Spraying (FFESS) of poly(D,L-lactide-*co*-glycolide)," *Biomaterials*, 2004, 25:5649-5658.
Bernkop-Schnurch, "Chitosan and its derivatives: potential excipients for peroral peptide delivery systems," *International J. of Pharmaceutics*, 2000, 194: 1-13.
Berry et al., "Functionalisation of magnetic nanoparticles for applications in biomedicine," *J. Phys. D: Appl. Phys.*, 2003, 36:R198-R206.
Biercuk et al., "Low-temperature atomic-layer-deposition lift-off method for microelectronic and nanoelectronic applications," *Applied Physics Letters*, vol. 83, No. 12, Sep. 22, 2003, pp. 2405-2407.
Blanusa et al., "Chelators as Antidotes of Metal Toxicity Therapeutic and Experimental Aspects," *Current Medicinal Chemistry*, 2005, vol. 12, pp. 2771-2794.
Bolz et al., "Effect of smooth, porous and fractal surface structure on the properties of an interface," *J. Materials Science: Materials in Medicine*, 1995, 844-848.
Bosiers et al., "Absorbable Metal stent for CLI in Infrapopliteal lesions: 1 year results," *CX 2005 Global Endovascular Forum*, Apr. 2005, pp. 1-23.
Brandau et al., "Nanoporous Ceramic Coatings for Synthesis of Radioactive Implants," *Journal of Nuclear Medicine Abstract Book*, Jun. 7, 2000, p. 244P, Abstract No. 1076.
Brückner et al., "Metal plasma immersion ion implantation and deposition (MPIIID): chromium on magnesium," *Surface and Coatings Technology*, 1998, 103-104, pp. 227-230.
Brunatto and Muzart, "Influence of the gas mixture flow on the processing parameters of hollow cathode discharge ion sintering," *J. Phys. D.: Appl. Phys.*, 2007, 40: 3937-3944.
Brunner et al., "Porosity Tailored Growth of Black Anodic Layers on Magnesium in an Organic Electrolyte," *Journal of the Electrochemical Society*, vol. 156 (2), Dec. 12, 2008, pp. C62-C66.
Buescher et al., "Characterization of Wet-Chemically Nanostructured Stainless Steel Surfaces," *Mat. Res. Soc. Symp. Proc*, 2001, 676:1-6.
Caruso et al., "Ultrathin Molybdenum Polyoxometalate-Polyelectrolyte Multilayer Films," *Langmuir*, 1998, 14:3462-3465.
Casan-Pastor et al., "Polyoxometalates: From Inorganic Chemistry to Materials Science," *Frontiers in Bioscience*, 2004, 9:1759-1770.
Chaieb et al , "Inhibition of the corrosion of steel in 1 M HC1 by eugenol derivatives," *Applied Surface Science*, 2005, 246:199-206.
Chang et al., "Effect of Heat Treatment on Corrosion and Electrochemical behavior of Mg-3Nd-0.2Zn-0.4Zr (wt. %) alloy," *Science Direct, Electrochimica Acta 52*, 2007, 3160-3167.
Chang et al., "Templated sythesis of Gold-iron Alloy nanoparticles using pulsed laser deposition," *Nanotechnology*, vol. 17, 2006, pp. 5131-5135.

Changwen et al., "Polyoxometalate-based organic-inorganic hybrid materials," 2004, *Sol-Gel*, p. 1.

Chen et al., "Laser Cladding of Mg20Al8o Powder on ZM5 Magnesium Alloy," *Corrosion Engineering, Science and Technology*, 2007, vol. 42, No. 2, pp. 130-136.

Cheng et al., "Electrogeneration and electrochemical properties of hybrid materials: polypyrrole doped with polyoxometalates $PW_{12-x}Mo_xO_{40}^{3-}$ (x=0,3,6,12)," *Synthetic Metals*, 2002, 129: 53-59.

Cho et al., "Gold-coated iron nanoparticles: a novel magnetic resonance agent for $T_1$ and $T_2$ weighted imaging," *Nanotechnology*, vol. 17, 2006, pp. 640-644.

Chou et al., "Electrochemical treatment of mouse and rat fibrosarcomas with direct current," *Bioelectromagnetics*, 1997, 18:14-24.

Clemente-Leon et al., "Hybrid Langmuir-Blodgett Films Formed by Alternating Layers of Magnetic Polyoxometalate Clusters and Organic Donor Molecules—Towards the Preparation of Multifunctional Molecular Materials," *Adv. Mater.*, 2001, 13:574-577.

Cogger et al. "An Introduction to Electrochemical Impedance Measurement," *Solartron Analytical*, 1999, 2-14.

Conolly et al., "X-Ray microtomography studies of localized corrosion and transitions to stress corrosion cracking," *Materials Science and Technology*, 2006, vol. 22, No. 9, pp. 1076-1085.

Costa et al., "The effect of the magnetic field on the corrosion behavior of Nd-Fe-B permanent magnets." *Journal of Magnetism and Magnetic Materials*, 278, 2004, pp. 348-358.

Damen et al., "Paclitaxel esters of malic acid as prodrugs with improved water solubility," *Bioorganic & Medicinal Chemistry*, 2000, 8: 427-432.

Damiani et al., "Vasorelaxant effects on eugenol on rat thoracic aorta," *Vascular Pharmacol.*, 2003, 40:59-66.

Davies, "Changing the salt, changing the drug," *The Pharmaceutical Journal*, 2001, 266: 322-323.

De Geest et al., "Self-rupturing Microcapsules," *Adv. Mater.*, 2005, vol. 17, pp. 2357-2361.

de Witte, "Analysis of the principal component of external casing corrosion in deep wells," *J. Appl. Electrochem.*, 1985, 15: 325-334.

Dexter, "Galvanic Corrosion," MAS Note, University of Delaware Sea Grant Marine Advisory Service, 2003.

Di Mario et al., "Drug-eluting bioabsorbable magnesium stent," *J. Interventional Cardiol.*, 2004, 17(6): 391-395.

Di Mario et al., "MOONLIGHT: a controlled registry of an iridium oxide-coated stent with angiographic follow-up," *Int. J. Cardiol.*, 2004, 95:329-331.

Dowling et al., "Anti-bacterial silver coatings exhibiting enhanced activity through the addition of Platinum," *Surf. & Coatings Tech.*, 2003, 163-164:637-640.

Duncan et al., "Polymer-drug conjugates, PDEPY and PELT: basic principles for design and transfer from the laboratory to clinic," *Journal of Controlled Release*, 2001, 74: 135-146.

Duncan, "The dawning era of polymer 360 therapeutics," *Nature Reviews/Drug Discovery*, 2003, 2: 347-360.

Duygu, "*Controlled Release Systems*," http://www.biomed.metu.edu.tr/courses/term_papers/contr-rel-sys_duygu.htm (Dec. 30, 2005).

Eggebrecht et al., "Novel Magnetic Resonance-Compatible Coronary Stent: The Absorbable Magnesium-Alloy Stent," *Circulation*, 2005, 112: 303-304.

Eniola et al., "Characterization of Biodegradable Drug Delivery Vehicles with the Adhesive Properties of Leukocytes II: Effect of Degradation on Targeting Activity," *Biomaterials*, 26:661-670.

Erbel et al., "Absorbierbare Stents-Eine Vielversprechende Neuerung?" *Urban & Vogel*, No. 4, 2007, pp. 308-319.

Erbel et al., "Temporary scaffolding of coronary arteries with bioabsorbable magnesium stents: a prospective, non-randomised multicentre trial," *Lancet*, 2007, vol. 369, pp. 1869-1875.

Erne et al., "The Road to Bioabsorbable Stents: Reaching Clinical Reality?" *Cardio Vascular and Interventional Radiology*, Sep. 26, 2005, pp. 11-16.

International Preliminary report on Patentability received in PCT/US2007/078417, mailed Mar. 26, 2009, 8 pages.

International Preliminary Report on Patentability, received in PCT/US2007/078407, mailed Mar. 26, 2009, 6 pages.

European Search Report from EP 10159664.1, mailed Jun. 4, 2010, 3 pages.

International Preliminary Report on Patentability in PCT/US05/16600 mailed Nov. 30, 2006, 7 pages.

International Search Report/Written Opinion in PCT/US05/16600 mailed May 4, 2006, 15 pages.

International Preliminary Report on Patentability in PCT/US07/78476 mailed Mar. 26, 2009, 7 pages.

International Preliminary Report on Patentability in PCT/US07/78411 mailed Feb. 4, 2009, 8 pages.

International Preliminary Report on Patentability in PCT/US07/78412 mailed Apr. 2, 2009, 7 pages.

International Preliminary Report on Patentability in PCT/US07/78450 mailed Mar. 26, 2009, 7 pages.

Falotico, "Cordis Fully Bioabsorbable Stent Program," *Euro PCR09*, May 22, 2009, pp. 1-21.

Fan et al., "Influence of Lanthanum on the microstructure, mechanical property and corrosion resistance of magnesium alloy," *J. Mater Sci*, 2006, vol. 41, pp. 5409-5416.

Fan et al., "Metallic Stents Coated with Bioabsorable Polymers," *Cardiac Interventions Today*, Jun./Jul. 2009, pp. 42-49.

Farhat et al., "Corrosion Control Using Polyelectrolyte Multilayers," *Electrochemical and Solid State Letters*, 2002, 5(4):B13-B15.

Feng et al., "Sonochemical preparation photochromic nanocomposite thin film based on polyoxometalates well dispersed in polyacrylamide," *Journal of Solid State Chemistry*, 2002, 169: 1-5.

Feng et al., "Superplasticity and texture of SiC whiskers in a magnesium-based composite," *Scripta Materialia*, 2005, 53: 361-365.

Ferguson et al., "Corrosion—Fatigue Performance of Magnesium Alloys," *International Journal of Modern Physics B*, vol. 17, Nos. 8 & 9, 2003, pp. 1601-1607.

Ferrando, "Review of Corrosion and Corrosion Control of Magnesium Alloys and Composites," *J. Mater. Eng.*, 1989, 11:299-313.

Fischer et al., "Determination of in-vivo corrosion rates of degradable implants by SR-microtomography," date unknown, pp. 1-2.

Fischer et al., "Hydrogen in magnesium alloys and magnesium interfaces: preparation, electronic properties and interdiffusion," *J. Less-Common Metals*, 1991, 172:808-815.

Fontenier et al., "Study of a 'Platinum-Magnesium' Cell to Supply Current to a Pacemaker," *Bioelectrochemistry and Bioenergetics*, 1975, 2(2):106-123.

Franhofer Institut Fertigungstechnik Material forschung, Evaluation of metal injection moulding (MIM) and extrusion as processing technology for biodegradable stents (A 208143), 8 pages.

Franhofer Institut Fertigungstechnik Material forschung, "Phase 2: Evaluation of mictoextrusion," 4 pages.

Fraunhofer Ezrt, "Quantitative material analysis by dual energy computed tomography for industrial NDT applications," 2009, 1 pg.

Fraunhofer IIS—Poster (German), "Prinzip der hochauflösenden Comptuertomographie," 2009, 1 page.

Frei, "On the Role of Vitamin C and Other Antioxidants in Atherogenesis and Vascular Dysfunction," *Proceedings—Society for Experimental Biology and Medicine*, 1999, 222:196-204.

Gabrielli, Claude. "Use and Applications of Electrochemical Impedance Techniques," *Solartron Analytical*, 1997, 1-102.

Garner et al., "Polypyrrole-heparin composites as stimulus-responsive substrates for endothelial cell growth," *J. Biomed. Mater. Res.*, 1999, 44: 121-129.

Gettleman et al., "Measurement of in vivo corrosion rates in baboons, and correlation with in vitro tests," Journal of Dental Research, 1980, 59: 689-707.

Gettleman et al., "Materials Science: Measurement of in vivo Corrosion Rates in Baboons, and Correlation with in vitro Tests," *Journal of Dental Research*, 1980, vol. 59, pp. 689-707.

Gomes et al., "Alternative tissue engineering scaffolds based on starch: processing methodologies, morphology, degradation and mechanical properties," *Materials Science and Engineering C*, 2002, 20:19-26.

Grassi et al., "Short-term administration of dark chocolate by a significant increase in insulin sensitivity and a decrease in blood pressure in healthy persons," *Am. J. Clin. Nutr.*, 2005, 81(3):611-614.

Gray and Luan, "Protective coatings on magnesium and its alloys—a critical review," *J. Alloys Compounds*, 2002, 336:88-113.
Griffiths et al., "Future devices: bioabsorbable stents," *Br. J. Cardiol. (Acute & Interventional Cardiology)*, 2004, 11: AIC80-AIC84.
Grube, "Bioabsorbable Stents-The Boston Scientific & REVA Technology," *EuroPCR 2009*, 2009, pp. 1-27.
Gu et al., "In vitro Corrosion and biocompatibility of binary magnesium alloys," *Biomaterials*, vol. 30, 2009, pp. 484-498.
Guo et al., "Manipulation of single-wall carbon nanotubes into aligned molecular layers," *Chem. Phys. Lett.*, 2002, 362:314-318.
Guo et al., "Multi-layer LB films of single-wall carbon nanotubes," *Physica B*, 2002, 323:235-236.
Gupta et al., "Nanometer spaced electrodes using selective area atomic layer deposition," *Applied Physics Letters*, vol. 90, 2007, pp. 1-4.
Gurib-Fakim, "Medicinal plants: Traditions of yesterday and drugs of tomorrow," *Molecular Aspects of Medicine*, 2006, 27:1-93.
Haenzi et al., "Design strategy for microalloyed ultra-ductile Mg alloys," 2009, *Phil. Mag. Letters*, 89(6): 377-390.
Haenzi et al., "Design strategy for new biodegradable Mg-Y-Zn alloys for medical applications," *Int. J. Mat. Res.*, 2009, 100: 1127-1136.
Haenzi et al., "On the biodegradation performance of an Mg-Y-RE alloy with various surface conditions in simulated body fluid," *Acta Biomat.*, 2009, 5: 162-171.
Haferkamp et al., "Magnesium-Base-Alloys as Implant-Material Steps to the Production of Thin Components," *Magnesium*, 2000, 159-164.
Hamu et al., "Influence of Si, Ca and Ag addition on corrosion behavior of new wrought Mg-Zn alloys," 2006, 22(10): 1213-1218.
Hänzi et al., "Design strategy for microalloyed ultra-ductile magnesium alloys," *Philosophical Magazine letters*, vol. 89, No. 6, Jun. 2009, pp. 377-390.
Hänzi et al., "Design strategy for new biodegradable Mg-Y-Zn alloys for medical applications," *Int. J. Mat. Res.*, vol. 100, 2009, pp. 1127-1136.
Hänzi et al., "On the biodegradation performance of an Mg-Y-Re alloy with various surface conditions in simulated body fluid," *Acta Biomaterialia*, vol. 5, 2009, pp. 162-171.
Haque et al. "Bioabsorption Qualities of Chitosan-absorbable Vascular Templates," *Current Surgery*, 2001, 58(1): 77-80.
Hau et al., "Surface-Chemistry Technology for Microfluidics," *J. Micromech. Microeng.*, 2003.13:272-278.
Heismann et al., "Density and atomic number measurements with spectral x-ray attenuation method," *Journal of Applied Physics*, vol. 94, No. 3, Aug. 1, 2003, pp. 2073-2079.
Hermawan et al., "Developments in metallic biodegradable stents," *Acta Biomaterialia*, 2010, 6:1693-1697.
Hermawan et al., "Degradable metallic biomaterials: Design and development of Fe-Mn alloys for stents," *Wiley InterScience: Article*, Apr. 19, 2008, pp. 1-12.
Hermawan et al., "Degradation Behaviour of Metallic Biomaterials for Degradable Stents," *Advanced Materials Research*, 2007, 15-17:113-118.
Hermawan et al., "Development of Degradable Fe-35Mn Alloy for Biomedical Application," *Advanced Material Research*, 2007, 15-17:107-112.
Hermawan et al., "Fe-Mn Alloys for Metallic Biodegradable Stents: Degradation and Cell Viability Studies," *Acta Biomaterialia*, Manuscript, Mar. 27, 2009, pp. 1-30.
Hermawan, et al., "Iron-Manganese: new class of metallic degradable biomaterials prepared by powder metallurgy," *Powder Metallurgy*, 2008, 51(1):38-45.
Heublein et al., "Biocorrosion of magnesium alloys: a new principle in cardiovascular implant technology?" *Heart*, 2003, 89:651-656.
Heublein et al., "Degradation of Metallic Alloys—A New Principle in Stent Technology?" *The American Journal of Cardiology, Eleventh Annual Symposium Transcatheter Cardiovascular Therapeutics Abstracts*, Sep. 22, 1999.
Heublein et al., "Bio-corrosion—a new principle for temporary cardiovascular implants?" *European Heart Journal, Journal of the European Society of Cardiology*, 2000, vol. 21, p. 286, Abstract No. P1605.
Heublein et al., "Local Tissue Engineering by Biocorrosion Vision or Reality?" *The American Journal of Cardiology, TCT Abstracts/Poster*, Oct. 16, 2000.
Hildebrandt et al., "Prevention of surface encrustation of urological implants by coating with inhibitors," *Biomaterials*, 2001, 22:503-507.
Holclajtner-Antunovic et al., "Study of some polyoxometallates of Keggin's type as potention antitumour agents," *Jugoslov Med. Biohem.*, 2004, 23: 25-30.
Hourng et al., Influence of multisteps thermal control in metal powder injection moulding process, *Powder Metallurgy*, 2008, 51: 84-89.
Huang et al., "A Review on Polymer Nanofibers by Electro-spinning and their Applications in Nanocomposites," 2003, 63:2223-2253.
Hutten, A. et al. "Ferromagnetic FeCo nanoparticles for biotechnology". (2005) *Journal of Magnetism and Magnetic Materials* 293:93-101).
Iakovou et al., "Incidence, Predictors, and Outcome of Thrombosis Successful Implantation of Drug-Eluting Stents," *JAMA*, 2005, 293(17): 2126-2130.
Ignat et al., "Magnesium alloys (WE43 and ZE41) characterization for laser applications," *Applied Surface Science*, 2004, 233:382-391.
Iida et al. "Surface modification of of$\lambda$Fe2O3 nanoparticles with aminopropylsilyl groups and interparticle linkage with with a,w-Dicarboxylic Acids". *Electrochimica Acta*. 2005. 855-859.
Imgrund, "Evaluation of metal injection moulding (MIM) and extrusions as processing technology for biodegradable stents. A 208143: Final report for phase I MIM of Fe and Fe-Si powders and sample characterisation," Aug. 15, 2008, *Fraunhofer Institut Fertigungstechnik Material forschung*, 18 pages.
Integran, "Biodegradable Nanometallic Intracoronary Stents," May 12, 2009, 1 page.
Integran, "Biodegradable Nanometallic Intracoronary Stents," Proposal, May 12, 2009, 1 page.
International Preliminary Report on Patentability in PCT/US07/60137 mailed Jul. 17, 2008, 7 pages.
International Preliminary Report on Patentability in PCT/US07/73839 mailed Apr. 2, 2009.
International Preliminary Report on Patentability in PCT/US07/78429 mailed Apr. 2, 2009.
International Preliminary Report on Patentability in PCT/US07/78475 mailed Mar. 26, 2009, 8 pages.
International Preliminary Report on Patentability received in PCT/US2007/078479, mailed Mar. 26, 2009, 8 pages.
International Search Report / Written Opinion in PCT/US09/046750 mailed Jul. 20, 2010, 14 pages.
International Search Report and Written Opinion in PCT/US07/78449, mailed Jan. 13, 2009, 15 pages.
International Search Report and Written Opinion in PCT/US07/78475, mailed Feb. 4, 2009, 14 pages.
International Search Report and Written Opinion in PCT/US07/78476, mailed Jan. 28, 2009, 29 pages.
International Search Report and Written Opinion mailed Jan. 25, 2008 in PCT/US07/75072, 14 pages.
International Search Report and Written Opinion received in PCT/US2007/078417, mailed Jan. 22, 2009, 18 pages.
International Search Report and Written Opinion received in PCT/US2007/078479, mailed Dec. 30, 2008, 12 pages.
International Search Report for PCT/US05/16600 mailed May 4, 2006, 4 pages.
International Search Report for PCT/US07/66568 dated Oct. 8, 2007, 15 pages.
International Search Report from PCT/US 03/20215, mailed Nov. 11, 2003, 4 pages.
International Search Report/Written Opinion in PCT/US07/73839 mailed Apr. 16, 2008, 16 pages.
International Search Report/Written Opinion in PCT/US07/78411 mailed Mar. 6, 2008, 12 pages.
International Search Report/Written Opinion in PCT/US07/78429 mailed Mar. 28, 2008, 14 pages.
International Search Report/Written Opinion in PCT/US2007/078407, mailed Mar. 26, 2008, 10 pages.

Ito et al., "Antioxidant action of eugenol compounds; role of metal ion in the inhibition of lipid peroxidation," *Food Chem. Toxicol.*, 2005, 43:461-466.

Ivanova and Ivanov, "Mechanisms of the extracellular antioxidant defend," *Experimental Pathology and Parasitology*, 2000, 4:49-59.

Jabara et al., "Bioabsorbable Stents: The Future is Near," *Cardiac Interventions Today*, Jun./Jul. 2009, pp. 50-53.

Jabara, "Poly-anhydride based on salicylic acid and adipic acid anhydride," Glimpse into the future: bioabsorbable stents-aimint to restore vascular integrity, *Euro PCR09*, 2009, pp. 1-34.

James A. Plambeck, "Electrolytic Processes of Nonmetals," *Chemical Sciences*, 1995, 2 pages.

Jiang et al., "Corrosion protection of polypyrrole electrodeposited on AZ91 magnesium alloys in alkaline solutions," *Synthetic Materials*, 2003, 139: 335-339.

Jiang et al., "Effect of $TiB_2$ particulate on partial remelting behavior of Mg-11A1-0.5Zn matrix composite," *Materials Science and Engineering A*, 2004, 381: 223-229.

Jiang, "A review of wet impregnation—An alternative method for the fabrication of high performance and nano-structured electrodes of solid oxide fuel cells," *Materials Science and Engineering A*, 2006, 418:199-210.

Kaesel et al., "Approach to Control the Corrosion of Magnesium by Alloying," *Magnesium Proceedings of the 6th International Conference Magnesium Alloys and Their applications*, 2004, pp. 534-539.

Kainer, "Magnesium alloys and technology," Wiley VCH, 2003, 119 pages.

Kaya et al., "Microstructure and Corrosion Resistance of Alloys of the Mg-Zn-Ag System," *Metal Science and Heat Treatment*, 2006, 48(11-12): 524-530.

Kean and Davies, "Cathodic Protection," 7 pages, 1981; http://www.npl.co.uk/upload/pdf/cathodic_protection.

Kececioglu, "Zur Biokompatibilitat eines neu entwickelten Stentmaterials aus korrodierbarem Reineisen," Jan. 25, 2007, pp. 1-131, *Ruhr-Universitat-Bochum*.

Kidambi et al., "Selective depositions on polyelectrolyte multilayers: self-assembled monolayers of m-dPEG acid as molecular template," *J. Am. Chem. Soc.*, 2004, 126: 4697-4703.

Kim et al., "Comprehensive study on vitamin C equivalent antioxidant capacity (VCEAC) of various polyphenols in scavenging a free radical and its structural relationship," *Crit. Rev. Food Sci. Nutr.*, 2004, 44(4):253-273.

Kim et al., "Effect of Anti-Oxidant (Carvedilol and Probucol) Loaded Stents in a Porcine Coronary Restenosis Model," *Circ. J.*, 2005, 69:101-106.

Kokubo et al., "How useful is SBF in predicting in vivo bone bioactivity?" *Biomaterials*, 2006, 27:2907-2915.

Kong et al., "Polyelectrolyte-functionalized multiwalled carbon nanotubes: preparation, characterization and layer-by-layer self assembly," *Polymer*, 2005, 46:2472-2485.

Kumar et al., "Polyanhydrides: an overview," *Advanced Drug Delivery Reviews*, 2002, 54:889-910.

Kurth et al., "Multilayer on Solid Planar Substrates: From Structure to Function", *Multi-layer Thin Films Sequential Assembly of Nanocomposite Materials*, 2003, Chapter 14, pp. 393-426.

Kurth et al., "Ultrathin Composite Films Incorporating the Nanoporous Isopolyoxomolybdate 'Keplerate' $(NH_4)_42[Mo_{132}O_{372}(CH_3COO)_{30}(H_2O)_{72}]$," *Chem. Mater.*, 2000, 12:2829-2831.

Kutsenko et al., "Structural Changes in Mg Alloy induced by plasma immersion ion implantation of Ag," *Acta Materialia*, 2004, 52:4329-4335.

LaFont, "Arterial Remodeling Technologies: Bioresorbable Stents," *Euro PCR09*, 2009, pp. 1-28.

Lambert et al., "Inhibition of carcinogenesis by polyphenols: evidence from laboratory investigations," *Am. J. Clin. Nutr.*, 2005, 81(suppl):284s-291S.

Lee et al., "Retentive and compressive strengths of modified zinc oxide-eugenol cements," *J. Dentistry*, 2000, 28:69-75.

Lee, J. et al. "Simple synthesis of mesoporous carbon with magnetic nano particles embedded in carbon rods". (2005) Carbon 43:2536-2543.

Lee, Sang-Yup et al. "Surface modification of magnetic nanoparticles capped by oleic acids: Characterization and colloidal stability in polar solvents" *Journal of Colloid and Interface Science* 293 (2006) 401-408.

Levesque et al., "Design of pseudo-physiological test bench specific to the development of biodegradable metallic biomaterials," *Acta Biomaterialia*, 2008, 4:284-295.

Li et al., "Effects of Direct Current on Dog Liver: Possible Mechanisms for Tumor Electrochemical Treatment," *Bioelectromagnetics*, 1997, 18:2-7.

Li et al., "Photoacoustic Tomography 97 and Sensing in Biomedicine," *Phys. Med. Biol.*, 2009, 54:59-97.

Li, "Poly(L-glutamic acid)-anticancer drug conjugates," *Advanced Drug Delivery Reviews*, 2002, 54:695-713.

Liao et al., "Fabrication of porous biodegradable polymer scaffolds using a solvent merging/particulate leaching method," *J. Biomed. Mater. Res.*, 2002, 59:676-681.

Lin et al., "Micropatterning proteins and cells on polylactic acid and poly(lactide-*co*-glycolide)," *Biomaterials*, 2005, 26:3655-3662.

Liu et al., "Characterizations of polypyrrole (PPy) nano-tubules made by templated ac electropolymerization," *European Polymer Journal*, 2005, 41: 2117-2121.

Liu et al., "Layer-By-Layer Ionic Self-Assembly of Au Colloids Into Multilayer Thin-Films with Bulk Metal Conductivity," *Chemical Physics Letters*, 1998, 298:315-319.

Liu et al., "Functional Polyoxometalate Thin Films via Electrostatic Layer-by-Layer Self-Assembly," *Journal of Cluster Science*, 2003, 14:405-419.

Liu et al., "Sol-gel deposited TiO2 film on NiTi surgical alloy for biocompatibility improvement," *Thin Solid Films*, 2003, 429:225-230.

Liu, *Introduction to Corrosion and Protection*, Corrosion and Protection Centre, School of Materials, The University of Manchester, 2006, 36 pages.

Lu et al. "Magnetic Switch of Permeability for Polyelectrolyte Microcapsules Embedded with Co@Au Nanoparticles". *American Chemical Society*. 2004.

Lu et al., "Theoretical analysis of calcium phosphate precipitation in simulated body fluid," *Biomaterials*, 2005, 26:1097-1108.

Maeng et al., "Negative Vascular Remodelling after Implantation of Bioabsorbable Magnesium Alloy Stents in Porcine Coronary Arteries: A randomized Comparison with Bare-Metal and Sirolimus-Eluting Stents," *Heart*, 2009, 95:241-246.

Maier et al., "High concentrations of magnesium modulate vascular endothelial cell behaviour in vitro," *Biochim Biophys. Acta*, 2004, 1689:6-12.

Mamedov et al., "Molecular Design of Strong Single-Wall Carbon Nanotube/Polyelectrolyte Multilayer Composites," *Nature Materials*, 2002, 1:190-194.

Maendl, "Zerstaubungsabscheidung von Mg-Legierungen," *Leibniz-Institut fur Oberflachenmodifizierung*, 2001, pp. 1-17.

Mani et al., "Coronary Stents: A materials perspective," *Biomaterials*, 2007, 28:1689-1710.

Mansfeld, Florian. "Analysis and Interpretation of EIS Data for Metals ans Alloys," *Solartron Analytical*, 1999, 1-77.

Marijan et al. "Surface Modification of Stainless Steel-304 Electrode. 2. An Experimental Comparative Study of Electrochemically, Hydrothermally and Chemically Modified Oxide Films." *CCACAA*, 1999, 72(4) 751-761.

Markman, "Absorbable Coronary stents," *The Lancet*, Jun. 2, 2007, 369:1839-1840.

Massaro et al., "Comparative Investigation of the surface properties of commercial titanium dental implants. Part 1: chemical composition," *Journal of Materials Science: Materials in Medicine*, vol. 13, 2002, pp. 535-548.

Matsuoka et al., "Hyperthermia Using Magnetite Cationic Liposomes for Hamster Osteosarcoma," *Biomagnetic Research and Technology*, Mar. 25, 2004, pp. 1-6.

Medical Device Daily, "Conor Cites Positive 12-month Results for Its CoStar Stent", May 2005 (1 page).

Meng Han, "Laser nitriding of metals: Influences of the ambient pressure and the pulse duration," 2001, Dissertation, Georg-August-Universität Göttingen, 134 pages.

*Methods in Cell Biology (Cell Death)*, vol. 46, p. 163.

Miao et al., "Porous Calcium Phosphate Ceramics prepared by coating polyurethane foams with Calcium phosphate cements," *Materials Letters*, vol. 58, 2004, pp. 397-402.

Middleton and Tipton, "Synthetic Biodegradable Polymers as Medical Devices." http://www.devicelink.com/mpb/archive/98/03/002.html, Mar. 1998, 9 pages.

Mihailovic et al., "Unusual Magnetic State in Lithium-Doped $MoS_2$ Nanotubes," *Phys Rev. Lett.*, 2003, 90 146401-1-4.

Mikos and Temenoff, "Formation of highly porous biodegradable scaffolds for tissue engineering," *Electronic Journal of Biotechnology*, 2000, 3(2):114-119.

Mohanty et al. "Evaluation of soft tissue response to a poly[urethane urea]," *Biomaterials*, 1992, 13(10):651-656.

Mohanty et al., "Effect of *Curcuma longa* and *Ocimum sanctum* on myocardial apoptosis in experimentally induced myocardial ischemic-reperfusion injury," *BMC Complementary and Alternative Medicine*, 2006, 6:3-14.

Molnar and Garai, "Plant-derived anti-inflammatory compounds affect MIF tautomerase activity," *International Immunopharmacology*, 2005, 5:849-856.

Moskaug et al., "Polyphenols and glutathione synthesis regualtion," *Am. J. Clin. Nutr.*, 2005, 81 (suppl):277S-283S.

Mueller et al., "Control of smooth muscle cell proliferation by ferrous iron," *Biomaterials*, vol. 27, 2006, pp. 2193-2200.

Mueller et al., "Magnesium and its Alloys as Degradable Biomaterials, Corrosion Studies Using Potentiodynamic and EIS Electrochemical Tenchiques," *Materials Research*, 2007, 10(1): 5-10.

Mueller et al., "Preparation of SBF with different $HCO_3$ content and its influence on the composition of biomimetic apatites," *Acta Biomaterialia*, 2006, 2:181-189.

Munoz et al., "Interactive Effects of Albumin and Phosphate Ions on the Corrosion of CoCrMo Implant Alloy," *Journal of the Electrochemical Society*, 2007, 154(10):562-570.

Nachtrab et al., "Quantitative Material Analysis by Dual-Energy Computed Tomography for Industrial NDT Applications," *Fraunhofer EZRT*, date unknown, 1 page.

Naderi et al., "Effect of some volatile oils on the affinity of intact and oxidized low-density lipoproteins for adrenal cell surface receptors," *Mol. Cell. Biochem.*, 2004, 267:59-66.

Nair and Laurencin, "Biodegradable polymers as biomaterials," *Prog. Polym. Sci.*, 2007, 32: 762-798.

Nguyen et al., "Mechanism for protection of iron corrosion by an intrinsically electronic conducting polymer," *Journal of Electroanalytical Chemistry*, 2004, 572: 225-234.

Ni et al., "Cellular localization of antiviral polyoxometalates in J774 macrophages," *Antiviral Research*, 1995, 32: 141-148.

Niemeyer et al., "Magnesium alloys as biodegradable metallic implant materials for cardiovascularic and orthopaedic surgery," *Euromat 2001, 7th European Conference on Advanced Materials and Processes*, Jun. 10-14, 2001 (Abstract).

Niinisto, "Atomic Layer deposition: A key technology for the controlled growth of oxide thin films for advanced applications," *Proc. Estonian Acad. Sci. Phys. Math.*, 2003, 52(3):266-276.

Nilsson et al., "Development of a dosage method for electrochemical treatment of tumours: a simplified mathematical model," *Bioelectrochemistry and Bioenergetics*, 1998, 47:11-18.

Ogata et al., "A novel anti-tumor agent, polyoxomolybdate induces apoptotic cell death in AsPC-1 human pancreatic cancer cells," *Biomedicine & Pharmacotherapy*, 2005, 59: 240-244.

Onuma et al., "Everolimus-eluting bioabsorbable stent," *Euro PCR09*, May 22, 2009, pp. 1-28.

Ormiston et al., "Bioabsorbable Coronary Stents," *Circulation Cardiovasc Intervent*, vol. 2, 2009, pp. 255-260.

Ou et al., "Protective effects of eugenol against oxidized LDL-induced cytotoxicity and adhesion molecule expression in endothelial cells," *Food Chem. Toxicol.*, 2006, 44:1485-1495.

Ouerd et al., "Reactivity of Titanium in Physiolgoical Medium—I. Electrochemical Characterization of the Metal/Protein Interface," *Journal of the Electrochemical Society*, vol. 154, No. 10, 2007, pp. 593-601.

Oyane et al., "Preparation and assessment of revised simulated body fluids," *Wiley Peridocals, Inc.*, 2003, pp. 188-195.

Paliwoda-Porebska et al., "On the development of polypyrrole coatings with self-healing properties for iron corrosion protection," *Corrosion Science*, 2005, 47: 3216-3233.

Peeters et al., "Preliminary Results after Application of Absorbable Metal Stents in Patients with Critical Limb Ischemia," *J. Endovasc Ther*, 2005, 12:1-5.

Peeters, et al., "Preliminary Data on Absorbable Metal Stents," *Meet 2006*, Jun. 2006, pp. 1-30.

Peuster et al. "Long-term biocompatibility of a corrodible peripheral iron stent in the porcine of descending aorta," *Biomaterials*, 2006, 4955-4962.

Peuster et al., "A novel approach to temporary stenting: degradable cardiovascular stents produced from corrodible metal-results 6-18 months after implantation into New Zealand white rabbits," *Heart*, 2001, 86(5):563-569.

Peuster et al., "Are resorbable implants about to become a reality," *Cardiol Young*, 2006, 16:107-116.

Pinto Slattow et al., "Optical coherence tomography and intravascular ultrasound imaging of bioabsorbable magnesium stent degradation in porcine coronary arteries," *Cardiovascular Revascularization Medicine 9*, (2008) pp. 248-254.

Prasse et al., "Electric Anisotropy of Carbon Nanofibre/Epoxy Resin Composites Due to Electric Field Induced Alignment," *Composites Science and Technology*, 2003, 63:1835-1841.

Purushothaman et al. "Reducing Mass-Transport Limitations by Application of Special Pulsed Current Modes". *Journal of the Electrochemical Society*. 152 (4), 2005, J33-J39.

Qasem et al., "Kinetics of paclitaxel 2'-N-methylpyridinium mesylate decomposition," *AAPS PharmSciTech*, 2003, 4(2), Article 21, 8 pages.

Quinard et al., "Development of metal/polymer mixtures for micro powder injection moulding," *10th ESAFORM Conference on Material Forming*, 2007, pp. 933-939.

Qureshi et al., "The emerging role of iron, zinc, copper, magnesium and selenium and oxidative stress in health and diseases," *Biogenic Amines*, vol. 19, No. 2, 2005, pp. 147-169.

Raman et al., "Laser assisted modification of surface microstructure for localised corrosion resistance of magnesium alloys," *Surface Engineering*, 2007, 23(2): 107-111.

Ratnam et al., "Role of antioxidants in prophylaxis and therapy: A pharmaceutical perspective," *J. Controlled Release*, 2006, 113:189-207.

Reece et al., "Metal transport studies on inherently conducting polymer membranes containing cyclodextrin dopants," *Journal of Membrane Science*, 2005, 249: 9-20.

Remskar et al., "Self-Assembly of Subnanometer-Diameter Single-Wall $MoS_2$ Nanotubes," *Science*, 2001, 292:479-481.

Ren et al., "Variations of dose and electrode spacing for rat breast cancer electrochemical treatment," *Bioelectromagnetics*, 2001, 22(3):205-211.

Rettig et al., "Composition of corrosion layers on a magnesium rare-earth alloy in simulated body fluids," *Journal of Biomedical Materials Research Part A*, Oct. 18, 2006, pp. 359-369.

Rettig et al., "Corrosion resistance studies on grain-boundary etched drug-eluting stents," *J. Mater Sci: Mater Med.*, 2007, vol. 18, pp. 1377-1387.

Rettig et al., "Time-dependent electrochemical characterization of the corrosion of a magnesium rare-earth alloy in simulated body fluids," *Journal of Biomedical Materials Research Part A*, 2007, 167-175.

Rezwan et al., "Biodegradable and bio active porous polymer/inorganic composite scaffolds for bone tissue engineering," *Biomaterials*, 2006, 27:3413-3431.

Rhule et al., "Polyoxometalates in Medicine," *Chem. Rev.*, 1998, 98:327-357.

Rinkevich et al., "Regeneration of Amputated Avian Bone by a Coral Skeletal Implant," *Biol Bull.*, vol. 197, Aug. 1999, pp. 11-13.

Rivers et al., "Synthesis of a novel, biodegradable electrically conducting polymer for biomedical applications," *Advanced Functional Materials*, 2002, 12: 33-37.

Russell-Stevens et al., "The effect of thermal cycling on the properties of a carbon fibre reinforced magnesium composite," *Materials Science and Engineering A*, 2005, 397: 249-256.

Rutledge et al., "Electrostatic Spinning and Properties of Ultrafine Fibers," *National Textile Center Annual Report*, Nov. 2001, M01-D22, pp. 1-10.

Ryan et al., "Fabrication methods of porous metals for use in orthopaedic applications," *Biomaterials*, 2006, 27:2651-2670.

Sastry et al., "DNA-Mediated Electrostatic Assembly of Gold Nanoparticles into Linear Arrays by a Simple Drop-Coating Procedure," *Appl. Phys. Left.*, 2001, 78:2943-2945.

Satoh et al., "Effect of Antioxidants on Radical Intensity and Cytotoxic Activity of Eugenol," *Anticancer Res.*, 1998, 18:1549-1552.

Sawitowski et al., "Nanoporous Alumina Coatings for Medical Implants and Stents—Radiotherapy, Drug Delivery, Biological Compatibility," *Materials Research Society Symposium Proceedings*, 1999, 581:523-528.

Sawitowski, "New Drug Delivery Systems—Examples of Applied Nanotechnology," *VDM World Microtechnologies Congress*, Sep. 25-27, 2000, Expo 2000, Hannover, Germany, Proveeds vol. 1, p. 343-346.

Sawyer et al., "Electrochemical Criteria in the Choice of Materials used in Vascular Prostheses," *Biophysical Mechanisms in Vascular Homeostasis and Intravascular Thrombosis*, 1965, pp. 337-348.

Schauer et al., "Protection of iron against corrosion with polyaniline primers," *Progress in Organic Coatings*, 1998, 33: 20-27.

Schetky, "Shape Memory Alloys," *Encyclopedia of Chemical Technology* (3rd ed.), 1982, John Wiley & Sons, 20:726.

Schinhammer et al., "Design strategy for biodegradable Fe-based alloys for medical applications," *Acta Biomaterialia*, 2009, pp. 1-9.

Schmidt et al., "Physiochemical changes in London clay adjacent to cast iron pipes," *IAEG 2006, The Geological Society of London*, Paper 313, 12 pages.

Schneider et al., "From functional core/shell nanoparticles prepared via layer-by-layer deposition to empty nanospheres," *Nano Letters*, 2004, 4: 1833-1839.

Schranz et al., "Bioabsorbable Metal Stents for Percutaneous Treatment of Critical Recoarctation of the Aorta in a Newborn," *Catheterization and Cardiovascular Interventions*, vol. 67, 2006, pp. 671-673.

Secheresse et al., "$(Mo_2O_2X_2)^{2+}$ (X=O,S), a magic building block for the design of wheel shaped metalates," *C.R. Chimie*, 2005, 8: 1927-1938.

Serruys et al., "A bioabsorbable everolimus-eluting coronary stent system (ABSORB): 2-year outcomes and results from multiple imaging methods," *The Lancet*, 2009, 373: 897-910.

Serruys, "Fourth Annual American College of Cardiology International Lecture," *Journal of the American College of Cardiology*, 2006, vol. 47, No. 9, pp. 1754-1768.

Serruys, "Glimpse into the future: bioabsorbable stents-aiming to restore vascular integrity—Introduction & Objectives," *Euro PCR09*, May 18, 2009, pp. 1-4.

Shaw, "Corrosion Resistance of Magnesium Alloys," *ASM Handbook* vol. 13A: *Corrosion: Fundamentals, Testing, and Protection*. 2003, 5 pages.

Shenoy et al., "Role of Chain Entanglements on Fiber Formation During Electrospinnig of Polymer Solutions: Good Solvent, Non-Specific Polymer-polymer Interaction Limit," *Polymer*, 2005, 46:3372-3384.

Shevchenk et al., "Porous Surface of NiTi Alloy Produced by Plasma Ion Implantation," *Institute of Ion Beam Physics and Materials Research*, 2005, Strasbourg, 1 page.

Shevchenko, "Structure, composition and mechanical properties of porous layers produced by argon PIII," *Forschungszentrum Dresden*, Oct. 2007, 8 pages.

Shi et al., "A novel electrically conductive and biodegradable composite made of polypyrrole nanoparticles and polylactide," *Biomaterials*, 2004, 25:2477-2488.

Shieh et al. "Aqueous dispersions of magnetite nanoparticles with NH3 surfaces for magnetic manipulations of biomolecules and MRI contrast agents" *Biomaterials*, 2005 26: 7183-7191.

Shin, "Experimental Characterization of Electrospinning: the Electrically Forced Jet and Instabilities," Polymer, 2001, 42:9955-9967.

Sieber, et al., "Investigations on the passivity of iron in borate and phosphate buffers, pH 8.4," *Corrosion Science*, vol. 48, 2006, pp. 3472-3488.

Singh et al., "Electrocatalytic Activity of Eletrodepositied Composite Films of Polypyrrole and $CoFe_2O_4$ Nanoparticles Towards Oxygen Reduction Reaction," *Electrochimica Acta*, 2004, 49:4605-4612.

Singh Raman et al., "Laser assisted modification of surface microstructure for localised corrosion resistance of magnesium alloys," *Surface Engineering*, 2007, 23(2):107-111.

Smith et al. "Patterning self-assembled monolayers" *Progress in Surface Science*. 2004. 75:1-68.

Song et al., "Galvanic corrosion of magnesium alloy AZ91D in contact with an aluminium alloy, steel and zinc," *Corrosion Science*, 2004, 46:955-977.

Soto et al., "Amporphous magnesium nitride films produced by reactive pulsed lasar deposition," Journal of Non-Crystalline Solids, 2004, 342: 65-69.

Stoclet et al., "Vascular protection by dietary polyphenols," *Eur. J. Pharmacol.*, 2004, 500:299-313.

Stoner et al., "The mechanism of low frequency a.c. Electrochemical Disinfection," *Bioelectrochemistry and Bioenergetics*, 1982, 9:229-243.

Straumal et al., "Vacuum arc deposition of protective layers on glass and polymer," *Thin Solid Films*, 2001, 383:224-226.

Su et al., "Photoacoustic imaging of coronary artery stents," *Optics Express*, vol. 17, No. 22, Oct. 26, 2009, pp. 1-8.

Suhaj, "Spice antioxidants isolation and their antiradical activity: a review," *J. Food Composition and Analysis*, 2006, 19:531-537.

Sukhorukov et al., "Comparative Analysis of Hollow and Filled Polyelectrolyte Microcapsules Templated on Melamine Formaldehyde and Carbonate Cores," *Macromol. Chem. Phys.*, 2004, 205:530-535.

Sun et al., "Fabrication of a multilayer film electrode containing porphyrin and its application as a potentiometric sensor of iodide ion," *Talanta*, 1998, 46: 15-21.

Suslick et al., "The photochemistry of chromium, manganese, and iron porphytin complexes," J. Chem., 1992, 16:633-642.

Tada et al., "Distribution of pH during galvanic corrosion of a Zn/steel couple," *Electrochimica Acta*, 2004, 49:1019-1026.

Tan et al., "Systematic Parameter Study for Ultra-Fine Fiber Fabrication Via Electrospinning Process," *Polymer*, 2005, 46:6128-6134.

Tian et al., "Corrosion resistance improvement of magnesium alloy using nitrogen plasma ion implantation," *Surface & Coatings Technology*, 2005, 198:454-458.

Truong et al., "Corrosion protection of magnesium by electroactive polypyrrole/paint coatings," *Synthetic Metals*, 2000, 110: 7-15.

Turler et al., "Experimental low-level direct current therapy in liver metastases: influence of polarity and current dose," *Bioelectromagnetics*, 2000, 21(5):395-401.

Uhlmann et al., "Schnelle 3D-Analyse von Gefugemerkmalen" *Druckguss*, Apr. 2009, pp. 1-5.

Van Alst, "Potential conflicts of interest," *Euro PCR09*, 2009, pp. 1-22.

Vermette et al., "Immobilized Liposome Layers for Drug Delivery Applications," *J. Controlled Release*, 2002, 80:179-195.

Virtanen et al., "Electrochemical Behavior of Fe in Phosphate Solutions Studied by In Situ X-Ray Absorption Near Edge Structure," *Journal of the Electrochemical Society*, vol. 146, No. 11, 1999, pp. 4087-4094.

Virtanen et al., "Special modes of corrosion under physiological and simulated physiological conditions," *Acta Biomaterialia*, vol. 4, 2008, pp. 468-476.

Virtanen, "Corrosion of Biomedical Implant Materials," *Corrosion of Biomedical Implant Materials*, vol. 26, Nos. 2-3, 2008, pp. 147-171.

Volkova, "Effect of Deformation and Heat Treatment on the Structure and Properties of Magnesium Alloys of the Mg-Zn-Zr System," *Metal Science and Heat Treatment*, vol. 48, Nos. 11-12, 2006, pp. 508-512.

Volynova et al., "Mechanical Properties and the Fine Structure of Powdered Iron-Manganese Alloys," *Plenum Publishing Corp.*, 1987, pp. 999-1006.

von Euler et al., "Cell proliferation and apoptosis in rat mammary cancer after electrochemical treatment (EChT)," *Bioelectrochemistry*, 2004, 62:57-65.

Vrbanic et al., "Air-Stable Monodispersed $Mo_6S_3I_6$ Nanowires," *Nanotechnology*, 2004, 15:635-638.

Waksman et al., "Early-and Long-Term Intravascular Ultrasound and Angiographic Findings After Bioabsorbable Magnesium Stent Implantation in Human Coronary Arteries," *JACC: Cardiovascular Interventions*, vol. 2, No. 4, 2009, p. 1-9.

Waksman et al., "Safety and Efficacy of Bioabsorbable Magnesium Alloy Stents in Procine Coronary Arteries," *Catherterization and Cardiovascular Intervnetions*, 2006, vol. 68, pp. 607-617.

Waksman et al., "Short-term Effects of Biocorrodible Iron Stents in Porcine Coronary Arteries," *Journal of Interventional Cardiology*, vol. 21, No. 1, 2008, pp. 15-20.

Waksman, "Update on Bioabsorbable Stents: From Bench to Clinical," *Journal of Interventional Cardiology*, vol. 19, No. 5, 2006, pp. 414-421.

Waksman, Ron, "Current state of the metallic bioabsorbable stent," Glimpse to the Future, *Euro PCR09*, 2009, pp. 1-24.

Waksman, Ron, "Why Bioabsorbale Stent Technology," Glimpse to the Future, *Euro PCR09*, 2009 pp. 1-16. Future, Euro PCR09, 2009.

Wallerath et al., "A blend of polyphenolic compounds explains the stimulatory effect of red wine on human endothelial NO synthase," *Nitric Oxide*, 2005, 12:97-104.

Wan et al., "Preparation and characterization of porous conducting poly(DL-lactide) composite membrances," *Journal of Membrane Science*, 2005, 246: 193-201.

Wan et al., "Influence of Plasma Immersion Ion Implantation on Corrosion Properties of Magnesium," *Southwest Jiaotong University*, 2005, Chengu, 11 pages.

Wang et al., "Nonlinear optical properties of thin iron films grown on MgO (100) by uplsed laser deposition," *Thin Solid Films*, 2005, 471:86-90.

Wang et al., "Polyaniline microrods synthesized by a polyoxometalates/poly(vinyl alcohol) microfibers template," *Materials Letters*, 2005, 59: 3982-3985.

Weiss et al., "Pyrrole derivatives for electrochemical coating of metallic medical devices," J. Polymer Science, Part A: Polymer Chemistry, 2004, 42: 1658-1667.

Wang et al., "Characterisation of Severely Deformed Austenitic Stainless Steel Wire," *Materials Science and Technology*, 21(11):1323-1328.

Wang, "Recent development of non-platinum catalysts for oxygen reduction reaction," *J. Power Sources*, 2005, 152:1-15.

Weber et al., "Hardness and corrosion resistance of single-phase nitride and carbide on ion," *Materials Science and Engineering*, 1995, 99:205-210.

Weh et al., "Evolution of afractal-like surface structures in layers of polyacrylonitrile solutions by interfacial dynamic processes," *J. Colloid and Interface Science*, 2004, 271: 407-415.

Weiss et al., "Pyrrole derivatives for electrochemical coating of metallic medical devices," *J. Polymer Science*, Part A: Polymer Chemistry, 2004, 42: 1658-1667.

White and Slade, "Polymer electrodes doped with heteropolymetallates and their use within solid-state supercapacitors," *Synthetic Metals*, 2003, 139: 123-131.

Widmer et al., "Manufacture of porous biodegradable polymer conduits by an extrusion process for guided tissue regeneration," *Biomaterials*, 1998, 19:1945-1955.

Wieneke et al., "Stent Coating: A New Approach in Interventional Cardiology," *Herz*, 2002, 27(6):518-526.

Wilcox, "Biodegradable Technology: Medtronic Biodegradable Stent Program," *Euro PCR09*, 2009 pp. 1-25.

Williamson and Manach, "Bioavailability and bioefficacy of polyphenols in humans. II. Review of 93 intervention studies,"*Am. J. Clin. Nutr.*, 2005, 81(suppl):243s-255S.

Windecker et al., "Biolimus-eluting stent with biodegradable polymer versus sirolimus-eluting stent with durable polymer for coronary revascularisations (LEADRERS): a randomized non-inferiority trial," *The Lancet*, Sep. 1, 2008, pp. 1-11.

Witte et al., "Biodegradable magnesium-hydroxyapatite metal matrix composites," *Biomaterials*, vol. 28, 2007, pp. 2163-2174.

Witte et al., "In vitro and in vivo corrosion measurements of magnesium alloys," *Biomaterials*, 2006, 27:1013-1018.

Witte et al., "In Vivo Corrosion of Four Magnesium Alloys and the Associated Bone Response," *Biomaterials*, vol. 26, 2005, pp. 3557-3563.

Witte, "The history of biodegradable magnesium implants: A review," *Acta Biomaterialia*, 2010, 6: 1680-1692.

Witte, "Magnesium Corrosion: a New Challaenge for temporary Biomaterials," *Laboratory for Biomechanic and Biomaterials*, 2009, pp. 1-20.

Wuisman and Smit, "Bioresorbable polymers: heading for a new generation of spinal cages," *Eur. Spine J.*, 2006, 15: 133-148.

Xin et al., "Electrochemical Treatment of Lung Cancer," *Bioelectromagnetics*, 1997, 18:8-13.

Xu et al., "In Vivo corrosion behaviouc of Mg-MnZn alloy for bone implant application," *Journal of Biomedical Materials Research Part A*, Jun. 4, 2007, pp. 703-711.

Yamaguchi et al., "Mg2Si Coating Technology on Magnesium Alloys to Improve Corrosion and Wear Resistance", *JOM*, 2004, p. 343.

Ye et al., "In situ synthesis of AlN particles in Mg-Al alloy by $Mg_3$-$N_2$ addition," *Materials Letters*, 2004, 58: 2361-2361.

Yen et al., "Electrochemical treatment of human KB cells in vitro," *Bioelectromagnetics*, 1999, 20:34-41.

Yfantis et al., "Novel corrosion-resistant films for Mg alloys," *Surface and Coatings Technology*, 2002, 151-152: 400-404.

Yi et al., "Characterization of a bioactive nanotextured surface created by controlled chemical oxidation of titanium," *Surface Science*, 2006, 600:4613-4621.

You et al., "The Effect of Calcium Additions on the Oxidation Behavior in Magnesium Alloys," *Scripta mater.*, 2000, 42:1089-1094.

Yu and Uan, "Sacrificial Mg film anode for cathodic protection of die cast Mg-9-wt.%-1 wt.%Zn alloy in NaCl aqueous solution," *Scripta Mat.*, 2006, 54:1253-1257.

Yue et al., "Improvement in the Corrosion Resistance of Magnesium ZK60/SiC Composite by Excimer Laser Surface Treatment," *Scripta Materialia*, 1998, 38(2):191-198.

Yuen et al., "Findings from an Accelerated in Vivo Corrosion Model of Magnesium," *Department Orthopaedics and Traumatology*, date unknown, pp. 1-2.

Yun et al., "Revolutionizing Biodegradable Materials," *Materials Today*, Oct. 2009, vol. 12, No. 10, pp. 1-11.

Zarras et al., "Progress in using conductive polymers as corrosion-inhibiting coatings," *Radiation Physics and Chemistry*, 2003, 68: 387-394.

Zberg et al., "MgZnCa glasses without clinically observable hydrogen evolution for biodegradable implants," *Nature materials*, Sep. 27, 2009, vol. 8, pp. 887-891.

Zeta Potential—An Introduction in 30 minutes, Technical Note; http://www.nbte.cornell.edu/facilities/downloads/Zeta%potential%20-%20An%20introduction%20in%2030%20minutes.pdf, Retrieved from the Internet on May 9, 2005 (6 pages).

Zhang et al., "Improving multilayer films endurance by photoinduced interaction between Dawson-type polyoxometalate and diazo resin," *Materials Chemistry and Physics*, 2005, 90:47-52.

Zhang et al., "Natural Polyelectrolyte Films Based on Layer-by-Layer Deposition of Collagen and Hyaluronic Acid," *Biomaterials*, 2005, 26:3353-3361.

Zhang et al., "Ways for fabricating stable layer-by layer self-assemblies: combined ionic self-assembly and post chemical reaction," *Colloids and Surfaces A: physiochemical and Engineering Aspects*, 2002, pp. 198-200, 439-442.

Zheng, "Symposium on Biodegradable/Biocorroded metallic materials," Nov. 24, 2009, pp. 1-74.

Zhou et al., "Drug-loaded, Magnetic, hollow silica nanocomposites for nanomedicine," *Nanomedicine: Nanotechnology, Biology and Medicine*, 2005, 1:233-237.

Zhu et al., "Biocompatibility of Fe-O films synthesized by plasma immersion ion implantation and deposition," *Surface and Coatings Technology*, vol. 203, 2009, pp. 1523-1529.

Zhu et al., "Biocompatibility of pure iron: In Vitro assessment of degradation kinetics and cytotoxicity on endothelial cells," *Materials Science and Engineering*, vol. 29, 2009, pp. 1589-1582.

Zou et al., "Preparation of a phosophopolyoxomolybdate $P_2Mo_{18}O^{6-}_{62}$ doped polypyrrole modified electrode and its catalytic properties," *Journal of Electroanalytical Chemistry*, 2004, 566: 63-71.

Zucchi et al., "Electrochemical behaviour of a magnesium alloy containing rare earth elements," *Journal of Applied Electrochemistry*, 2006, vol. 36, pp. 195-204.

Zucchi et al., "Influence of a silane treatment on the corrosion resistance of a WE43 magnesium alloy," *Surface Coatings Technol.*, 2006, 200:4136-4143.

International Search Report and Written Opinion from PCT/US09/043591, mailed Jun. 30, 2010, 10 pages.

International Search Report from PCT/US07/005671, mailed Jun. 2, 2008, 10 pages.

Ma et al., "Inhibition effect of self-assembled films formed by gold nonoparticles on iron surface," *Applied Surface Science*, 2006, 252: 4327-4334.

Li et al., "The corrosion inhibition of the self assembled Au, and Ag nonoparticles films on the surface of copper," Colloids and Surfaces A: Physiochem. Eng. Aspects, 2006, 273: 16-23.

International Preliminary Report on Patentability from PCT/US08/75976 dated Mar. 25, 2010, mailed Nov. 25, 2008, 8 pages.

Li et al., "The corrosion inhibition of the self assembled Au, and Ag nonoparticles films on the surface of copper," Colloids and Surfaces A: Physiochem. Eng. Aspects, 2006, 273: 16-23.

International Preliminary Report on Patentability from PCT/US08/75976 dated Mar. 25, 2010, mailed Nov. 25, 2008, 8 pages.

Viswanathamurthi et al., "Preparation and morphology of niobuim oxide fibres by electrospinning," *Chemical Physics Letters*, 2003, 374: 79-84.

Authorized Officer Henrique Amaro, International Preliminary Report on Patentability from PCT/US09/043326 mailed Nov. 18, 2010, 7 pages.

Authorized Officer Jasmine Messemanne, International Search Report from PCT/US09/051965 mailed Aug. 20, 2010, 13 pages.

Authorized Officer Jasmine Messemanne, International Preliminary Report on Patentability from PCT/US09/051965 mailed Feb. 10, 2011, 8 pages.

Authorized Officer Antonio Espuch, International Preliminary Report on Patentability in PCT/US09/49422 mailed Jan. 13, 2011, 7 pages.

Authorized Officer Aurore Schneider, International Preliminary Report on Patentability from PCT/US2010/042772 mailed Feb. 4, 2011, 9 pages.

Authorized Officer Henrique Amaro, International Preliminary Report on Patentability in PCT/US2009/43326 mailed Nov. 18, 2010, 7 pages.

Authorized Officer Antoine Laurent, International Preliminary Report on Patentability in PCT/US09/046750 mailed December 23, 2010, 8 pages.

Deepwater, "Galvanic Series," http://corrosion-doctors.org/definitions/galvanic-series.htm> on Mar. 11, 2011, 5 pages.

Wikipedia, the Free Encyclopedia, "Galvanic Corrosion." <http://en.wikipedia.org/wiki/Galvanic_corrosion> on Mar. 11, 2011, 7 pages.

Authorized Officer Mary Celine, International Search Report from PCT/US2010/060412 mailed Feb. 21, 2011, 10 pages.

Dumas et al., "Characterization of magnesium fluoride thin films produced by argon ion beam-assisted deposition," *Thin Sold Films*, 2001, pp. 61-68.

Authorized Officer Razik Menidjel, International Preliminary Report on Patentability from PCT/US09/059424, mailed May 5, 2011, 8 pages.

Park et al., "Microstructural change and precipitation hardening in melt-spun Mg-X-Ca alloys," *Science and Technology of Advanced Materials*, 2001, 2:73-78.

International Search Report/Written Opinion in PCT/US2007/078505 mailed Mar. 4, 2008, 10 pages.

US 6,533,715, 03/2003, Hossainy et al. (withdrawn)

\* cited by examiner

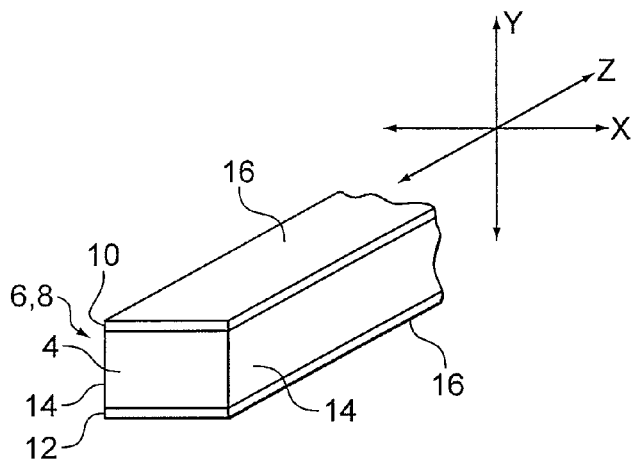
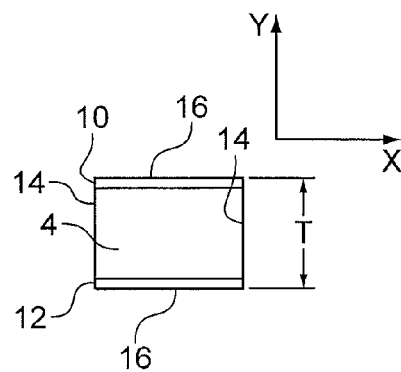
FIG. 2A  FIG. 2B
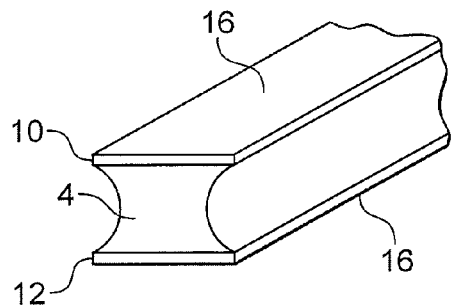
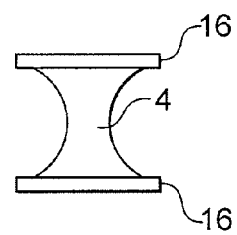
FIG. 3A  FIG. 3B
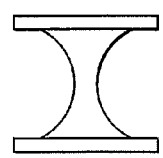
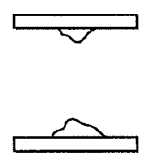
FIG. 3C  FIG. 3D

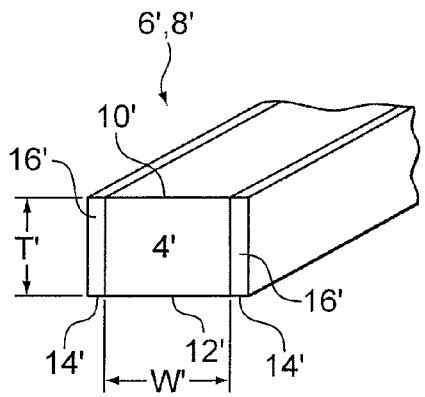
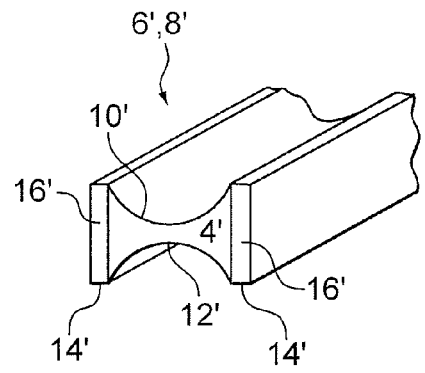
FIG. 4A     FIG. 4B
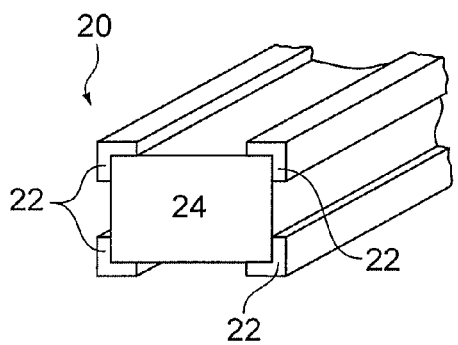
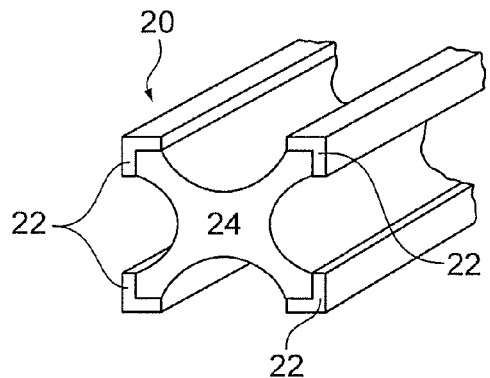
FIG. 5A     FIG. 5B
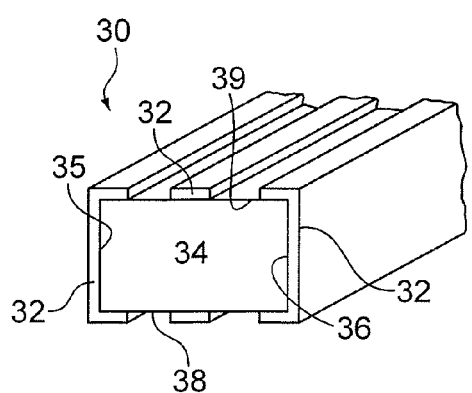
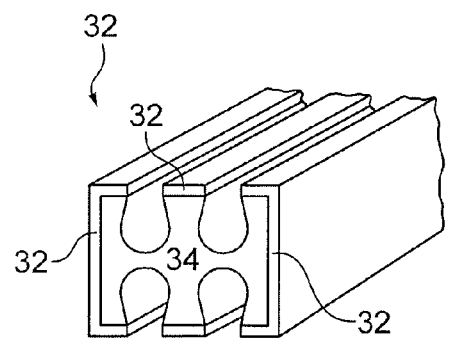
FIG. 6A     FIG. 6B

BIOERODIBLE ENDOPROSTHESES AND METHODS OF MAKING THE SAME

CROSS-REFERENCE TO RELATED APPLICATIONS

This application claims priority under 35 USC §119(e) to U.S. Provisional Patent Application Ser. No. 60/844,966, filed on Sep. 15, 2006, the entire contents of which are hereby incorporated by reference.

TECHNICAL FIELD

The invention relates to bioerodible endoprostheses, and to methods of making the same.

BACKGROUND

The body includes various passageways such as arteries, other blood vessels, and other body lumens. These passageways sometimes become occluded or weakened. For example, the passageways can be occluded by a tumor, restricted by plaque, or weakened by an aneurysm. When this occurs, the passageway can be reopened or reinforced with a medical endoprosthesis. An endoprosthesis is typically a tubular member that is placed in a lumen in the body. Examples of endoprostheses include stents, covered stents, and stent-grafts.

Endoprostheses can be delivered inside the body by a catheter that supports the endoprosthesis in a compacted or reduced-size form as the endoprosthesis is transported to a desired site. Upon reaching the site, the endoprosthesis is expanded, e.g., so that it can contact the walls of the lumen.

The expansion mechanism may include forcing the endoprosthesis to expand radially. For example, the expansion mechanism can include the catheter carrying a balloon, which carries a balloon-expandable endoprosthesis. The balloon can be inflated to deform and to fix the expanded endoprosthesis at a predetermined position in contact with the lumen wall. The balloon can then be deflated, and the catheter withdrawn from the lumen.

It is sometimes desirable for an implanted endoprosthesis to erode over time within the passageway. For example, a fully erodible endoprosthesis does not remain as a permanent object in the body, which may help the passageway recover to its natural condition. Erodible endoprostheses can be formed from, e.g., a polymeric material, such as polylactic acid, or from a metallic material, such as magnesium, iron or an alloy thereof.

SUMMARY

The invention relates to bioerodible endoprostheses and methods of making the endoprostheses. The endoprostheses can be configured to erode in a controlled and predetermined manner in the body.

In one aspect, the invention features an endoprosthesis including a body, which includes a cross section in the X-Y plane and extends along a z-axis; and an erosion modifying material provided on the surface of the body which controls erosion to form a predetermined geometry such that, after erosion of at least about 50 percent of the area of the body in the X-Y plane, at least one initial dimension of the initial geometry is maintained. The body has an initial geometry in the X-Y plane characterized by initial dimensions.

In another aspect, the invention features an endoprosthesis including a body, which includes a bioerodible metal material, has a cross-section in the X-Y plane, and extends along a z-axis; and a predetermined geometry after erosion of at least about 50 percent of the area of the body in the X-Y plane, the predetermined geometry is in the shape of an I, an X, an interdigitated structure, a radially lobed structure, or a convex structure. The body has an initial geometry in the X-Y plane characterized by initial dimensions.

In yet another aspect, the invention features an endoprosthesis including a body, which includes a bioerodible metal material, has a cross-section in the X-Y plane, and extends along a z-axis; and an erosion modifying material provided on the surface of the body which controls erosion to form a predetermined geometry, the modifying material being provided in a pattern of at least three separate regions in the X-Y plane. The body has an initial geometry in the X-Y plane characterized by initial dimensions.

Embodiments can include one or more of the following features.

The initial dimension can be maintained after erosion of at least about 55 percent (e.g., at least about 60 percent, at least about 65 percent, at least about 70 percent, at least about 75 percent, at least about 80 percent, at least about 85 percent, at least about 90 percent, at least about 95 percent) of the area of the body in the X-Y plane. The initial dimension maintained can correspond to the maximum dimension of the initial geometry. In some embodiments, the initial geometry is square or rectangular. In some embodiments, the initial geometry is circular, ovaloid, or elliptical. The ratio of the maximum initial dimensions in the X-Y plane can be between about 2:1 and about 1:2 (e.g., about 1:1).

The predetermined geometry can be an I shape. In some embodiments, the ends of the I correspond to abluminal and adluminal sides of the endoprosthesis. The predetermined geometry can be an X shape. In some embodiments, the predetermined geometry is an interdigitated geometry. In some embodiments, the predetermined geometry is a radially lobed structure. In some embodiments, the predetermined geometry is a convex structure. In some embodiments, the predetermined geometry is square or rectangular. The predetermined geometry can extend substantially the full extent of the body in the Z direction.

The bioerodible material can include a magnesium, calcium, aluminum, strontium, zirconium, zinc, manganese, iron, nickel, copper, cobalt, a rare earth element, and/or alloys thereof.

The erosion modifying material can include a polymer, a ceramic, an oxide, a metal, an alloy, and/or a composite. The erosion modifying material can be a layer. In some embodiments, the layer has varying thickness. The thickness can vary in the X and/or Y direction. The thickness can vary in the Z direction. The thickness can vary along the length of the endoprosthesis. The erosion modifying material can be provided on the entire surface of the body. The erosion modifying material can include multiple materials at select locations to control the erosion of the body.

In some embodiments, the body can be a strut. The endoprosthesis can be formed of a plurality of struts arranged in the general form of a tube. The endoprosthesis can be balloon expandable.

Embodiments may have one or more of the following advantages.

The endoprostheses may not need to be removed from a lumen after implantation. The endoprostheses can have a low thrombogenecity and high initial strength. The endoprostheses can exhibit reduced spring back (recoil) after expansion. Lumens implanted with the endoprostheses can exhibit reduced restenosis. The rate of erosion of different portions of the endoprostheses can be controlled, allowing the endoprostheses to erode in a predetermined manner and reducing, e.g., the likelihood of uncontrolled fragmentation and embolization. For example, the predetermined manner of erosion can be from an inside of the endoprosthesis to an outside of the endoprosthesis, or from a first end of the endoprosthesis to a second end of the endoprosthesis. The controlled rate of erosion and the predetermined manner of erosion can extend the time the endoprosthesis takes to erode to a particular degree of erosion, can extend the time that the endoprosthesis can maintain patency of the passageway in which the endoprosthesis is implanted, can allow better control over the size of the released particles during erosion, and/or can allow the cells of the implantation passageway to better endothelialize around the endoprosthesis.

An erodible or bioerodible endoprosthesis, e.g., a stent, refers to an endoprosthesis, or a portion thereof, that exhibits substantial mass or density reduction or chemical transformation, after it is introduced into a patient, e.g., a human patient. Mass reduction can occur by, e.g., dissolution of the material that forms the endoprosthesis and/or fragmenting of the endoprosthesis. Chemical transformation can include oxidation/reduction, hydrolysis, substitution, and/or addition reactions, or other chemical reactions of the material from which the endoprosthesis, or a portion thereof, is made. The erosion can be the result of a chemical and/or biological interaction of the endoprosthesis with the body environment, e.g., the body itself or body fluids, into which the endoprosthesis is implanted and/or erosion can be triggered by applying a triggering influence, such as a chemical reactant or energy to part or all of the endoprosthesis, e.g., to increase a reaction rate. For example, an endoprosthesis, or a portion thereof, can be formed from an active metal, e.g., Mg or Ca or an alloy thereof, and which can erode by reaction with water, producing the corresponding metal oxide and hydrogen gas (a redox reaction). For example, an endoprosthesis, or a portion thereof, can be formed from an erodible or bioerodible polymer, an alloy, and/or a blend of erodible or bioerodible polymers which can erode by hydrolysis with water. The erosion occurs to a desirable extent in a time frame that can provide a therapeutic benefit. For example, in embodiments, the endoprosthesis exhibits substantial mass reduction after a period of time when a function of the endoprosthesis, such as support of the lumen wall or drug delivery, is no longer needed or desirable. In particular embodiments, the endoprosthesis exhibits a mass reduction of about 10 percent or more, e.g. about 50 percent or more, after a period of implantation of one day or more, e.g. about 60 days or more, about 180 days or more, about 600 days or more, or 1000 days or less. In embodiments, only portions of the endoprosthesis exhibits erodibility. For example, an exterior layer or coating may be non-erodible, while an interior layer or body is erodible. In some embodiments, the endoprosthesis includes a non-erodible coating or layer of a radiopaque material, which can provide long-term identification of an endoprosthesis location.

Erosion rates can be measured with a test endoprosthesis suspended in a stream of Ringer's solution flowing at a rate of 0.2 ml/second. During testing, all surfaces of the test endoprosthesis can be exposed to the stream. For the purposes of this disclosure, Ringer's solution is a solution of recently boiled distilled water containing 8.6 gram sodium chloride, 0.3 gram potassium chloride, and 0.33 gram calcium chloride per liter of solution.

Other aspects, features and advantages will be apparent from the description of the preferred embodiments thereof and from the claims.

DESCRIPTION OF DRAWINGS

FIG. 2A is an enlarged perspective view of a portion of an endoprosthesis.

FIG. 2B is an enlarged cross-sectional view of and embodiment of the portion of the endoprosthesis of FIG. 2A.

FIG. 3A is an enlarged perspective view of a portion of an endoprosthesis.

FIG. 3B is an enlarged cross-sectional view of an embodiment of the portion of the endoprosthesis of FIG. 3A.

FIG. 3C is an enlarged cross-sectional view of an embodiment of the portion of the endoprosthesis of FIG. 3A.

FIG. 3D is an enlarged cross-sectional view of an embodiment of the portion of the endoprosthesis of FIG. 3A.

FIG. 4A is an enlarged perspective view of a portion of an endoprosthesis.

FIG. 4B is an enlarged perspective view of an embodiment of the portion of the endoprosthesis of FIG. 4A.

FIG. 5A is an enlarged perspective view of a portion of an endoprosthesis.

FIG. 5B is an enlarged perspective view of an embodiment of the portion of the endoprosthesis of FIG. 5A.

FIG. 6A is an enlarged perspective view of a portion of an endoprosthesis.

FIG. 6B is an enlarged perspective view of an embodiment of the portion of the endoprosthesis of FIG. 6A.

DETAILED DESCRIPTION

Figure 1A:
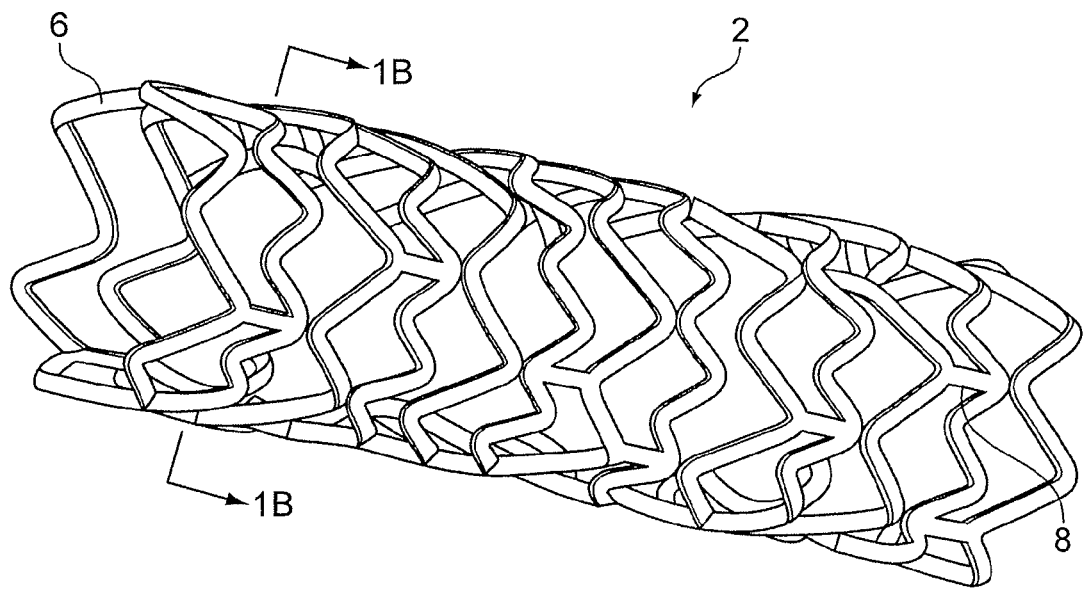
FIG. 1A is a perspective view of an embodiment of an endoprosthesis.
Figure 1B:
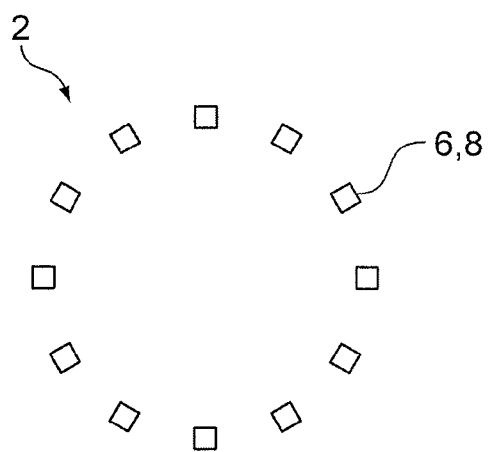
FIG. 1B is an enlarged cross-sectional view of the endoprosthesis of FIG. 1A.

Referring to FIGS. 1A and 1B, an endoprosthesis 2 includes a plurality of generally circumferential struts 6 and connecting struts 8. The circumferential struts 6 can be directly interconnected to one another and/or they can be connected by connecting struts 8. The endoprosthesis can be delivered into a body lumen, such as a vasculature, in a reduced diameter configuration and then expanded into contact with the lumen wall to, e.g., maintain patency at the site of an occlusion.

Referring as well to FIGS. 2A and 2B, a perspective cross-sectional view through a strut 6, 8, the strut is formed of a body 4 made of a bioerodible material, e.g., a metal such as magnesium. The strut also includes an erosion modifying material in layers 16 on the surface of the body 4. The erosion modifying material modifies the rate at which portions of the body 4 are eroded when the stent is placed in the lumen. In embodiments, the erosion modifying material is a non-erodible material or an erodible material that erodes at a different rate than the erodible material forming the body 4 so as to form a barrier that reduces or prevents exposure of the body 4 to physiological body fluids. For example, the erosion modifying material can be a ceramic such as an oxide of the erodible material forming the body 4 (e.g., magnesium oxide). The erosion modifying material can include a therapeutic drug.

The pattern of the erosion modifying material on the surface of the body, and the geometry and dimensions of the body are selected so that a desirable erosion geometry forms as the body erodes. In particular, the geometry of the eroding body can be selected to maintain the mechanical strength of the strut, even after substantial erosion, and to reduce premature fragmentation or fragmentation into large pieces.

Continuing to refer to FIGS. 2A and 2B, the strut 6, 8 extends in a direction along a Z-axis generally perpendicular to a plane on an X-Y axis. The cross-section or strut dimensions in the X-Y plane are generally smaller than along the Z-axis. In the illustrated embodiment, the strut has an initial rectangular geometry with an abluminal surface 10 (e.g., an exterior surface 10), an adluminal surface 12 (e.g., an interior surface 12) and two side surfaces 14. The strut has an initial thickness T between the surfaces 10 and 12 and an initial width W before the stent is implanted. The erosion modifying material is provided in corresponding coextensive layers 16 on the abluminal and adluminal surfaces of the body, which inhibit erosion from those surfaces. In some embodiments, each layer 16 can include a plurality of layers, which can include the same or different materials. Within each layer, the composition can include the same or different materials at different portions of the layer.

FIGS. 3A and 3B illustrate the strut after erosion upon implantation in a body lumen. Erosion of the body 4 occurs primarily at the side surfaces, yielding a I-beam geometry where the top and bottom of the I correspond to the abluminal and adluminal surfaces, respectively. The I-beam geometry provides mechanical strength to the strut even though a substantial amount of the body 4, e.g., 50% or more of the area in the X-Y plane has been eroded. Moreover, at least one dimension of the strut, the vertical line of the I corresponding to the strut thickness is maintained. The geometry of the I-beam can result as a function of surface diffusion and/or mass transport processes of the eroding endoprosthesis.

Referring as well to FIG. 3C, after further erosion, e.g., 75 percent or more of the strut has eroded, the I-beam geometry is still maintained. Referring as well to FIG. 3D, after 90 percent or more of the strut has eroded, the I-beam geometry is broken, and the erosion modifying layer is itself eroded. The erosion modifying layer reduces the likelihood that loose fragments of the body 4 will break off; the slow erosion of the strut also provides time for endothelialization prior to complete erosion.

Erosion to a desirable geometry can be controlled by selecting the initial dimensions and geometry of the bioerodible body, and the pattern and nature of the erosion control material. The bioerodible body preferably has a geometry such that the ratio of the characteristic dimensions in the X-Y direction is between about 2:1 to 1:2, e.g., about 1:1. For example, for a strut with a rectangular cross section, the ratio of the thickness to the width is about 2:1 to about 1:2. For a strut with a circular cross section, the ratio of its radii or diameters in the cross section is 1:1. As discussed above, the erosion modifying layer can include a biodegradable and/or non-biodegradable second material with a lower erosion rate than a first material of a bioerodible body of an endoprosthesis. Examples are ceramics, metals or polymers, which provide a barrier that reduces the exposure of the erodible body to fluids by requiring diffusion of body fluids through the erosion modifying layer or preventing exposure of the erodible body to body fluids. In some embodiments, the erosion modifying layer can include a plurality of layers, which can include the same or different materials. Within each layer, the composition can include the same or different materials at different portions of the layer. In some embodiments, the erosion rate of the erosion modifying layer is from about 10% (e.g., from about 25%, from about 50%, from about 150%, from about 200 percent, from about 400 percent, from about 600 percent, from about 8000%) less than the erosion rate of a bioerodible body to about 1000% (e.g., to about 800%, to about 600%, to about 400%, to about 200%, to about 150%) less than the erosion rate of a bioerodible body. In some embodiments, the erosion rate of erosion modifying layer can range from about 0.001% (e.g., from about 0.01%, from about 0.1%, from about 0.5%) to about 1% (e.g., to about 0.5%, to about 0.1%, to about 0.01%) of the initial mass of that portion per day. The erosion rate of a bioerodible body can range from about 0.2% (e.g., from about 0.5%, from about 1%, from about 2%) to about 5% (e.g., to about 2%, to about 1%, to about 0.5%) of the initial mass of that portion per day. In some embodiments in which the erosion modifying layer includes a non-biodegradable second material, the second material is radiopaque and can provide long term identification of the endoprosthesis location (e.g., by x-ray, MRI) within a body. In some embodiments, the erosion modifying layer includes stainless steel, which can promote endothelialization of the endoprosthesis and/or reduce thrombus risk.

The thickness of the erosion modifying material can be selected to control the rate of exposure of the erodible material to body fluid. The thickness can be uniform, variable in a gradient manner, variable in a stepwise manner, and/or variable in a random manner along a length or a width of an endoprosthesis. The thickness of the layers can range from about 1 nm (e.g., from about 5 nm, from about 25 nm, from about 100 nm, from about 500 nm, from about 800 nm, from about 1 µm, from about 2 µm, from about 3 µm, from about 4 µm, from about 5 µm, from about 6 µm, from about 7 µm, from about 8 µm, from about 9 µm) to about 10 µm (e.g., to about 9 µm, to about 8 µm, to about 7 µm, to about 6 µm, to about 5 µm, to about 4 µm, to about 3 µm, to about 2 µm, to 1 µm, to about 800 nm, to about 500 nm). The thickness of an erosion modifying layer can also be expressed as a fraction of a thickness of a bioerodible body. For example, the thickness of the erosion modifying layer can be at most about 50% (e.g., at most about 40%, at most about 30%, at most about 20%, at most about 10%, at most about 5%, at most about 2%, at most about 1%) the thickness of the bioerodible body and/or at least about 0.001%, (e.g., at least about 0.004%, at least about 0.01%, at least about 0.1%, at least about 1%, at least about 2%, at least about 5%, at least about 10%, at least about 25%) the thickness of the bioerodible body.

A strut can erode in a variety of erosion patterns and/or geometries. For example, referring to FIG. 4A, in some embodiments a strut 6', 8' has an initial rectangular geometry with an erodible body 4', an abluminal surface 10', an adluminal surface 12' and two side surfaces 14'. The strut has an initial thickness T' between the surfaces 10' and 12' and an initial width W' before the stent is implanted. Erosion modifying layers 16' are provided in corresponding coextensive layers on the side surfaces of the body, which inhibit erosion from those surfaces. FIG. 4B illustrates the strut after partial erosion, upon implantation in a body lumen. Erosion of body 4' occurs primarily at the abluminal and adluminal surfaces, resulting in a geometry as shown in FIG. 4B. Thickness T' decreases from the side surfaces toward the center of the strut. However, the width W' is maintained even though a substantial amount of the body 4', e.g., 50% or more of the area in the X-Y plane, has been eroded. The erosion geometry can provide mechanical strength to the eroded strut.

Figure 7A:
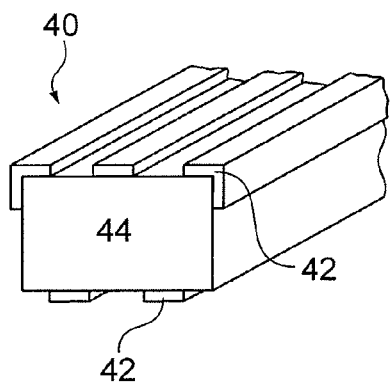
FIG. 7A is an enlarged perspective view of a portion of an endoprosthesis.
Figure 7B:
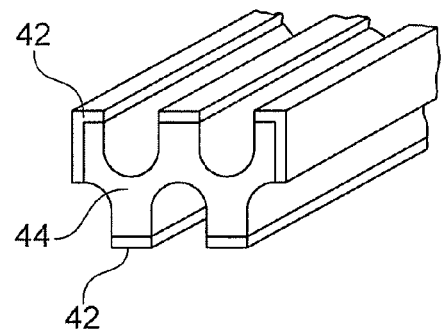
FIG. 7B is an enlarged perspective view of an embodiment of the portion of the endoprosthesis of FIG. 7A.

In some embodiments, erosion modifying layers are provided intermittently along the perimeter of a strut. As an example, as shown in FIG. 5A, layers 22 are provided at the four edges of strut 20. As shown in FIG. 5B, upon implantation, erosion of body 24 occurs starting at the uncoated side surfaces, resulting in a X-shaped geometry at the X-Y plane. As an example, as shown in FIG. 6A, erosion modifying layers 32 are provided at opposing surfaces 35, 36 including the four edges, and intermittently at the remaining surfaces 38, 39 of strut 30. Upon implantation, as shown in FIG. 6B, partial erosion of body 34 occurs at the exposed surfaces, resulting in a strut having grooves along the abluminal and adluminal surfaces. Referring to FIG. 7A, erosion modifying layers 42 are provided intermittently along the surfaces of strut 40, which result in erosion of body 44 starting at the exposed surfaces upon implantation in a body lumen. Referring to FIG. 7B, after erosion, the strut has a series of grooves forming an interdigitated pattern. The erosion geometry of struts 20, 30, 40 in FIGS. 5B, 6B, 7B can provide mechanical strength to the eroded strut.

Figure 8A:
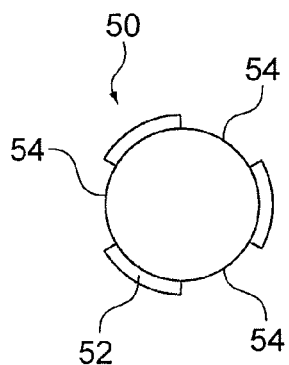
FIG. 8A is an enlarged cross-sectional view of a portion of an endoprosthesis.
Figure 8B:
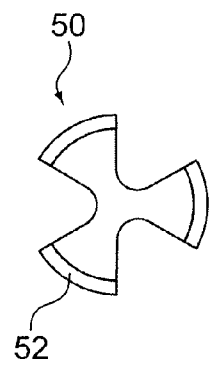
FIG. 8B is an enlarged cross-sectional view of an embodiment of the portion of the endoprosthesis of FIG. 8A.
Figure 9A:
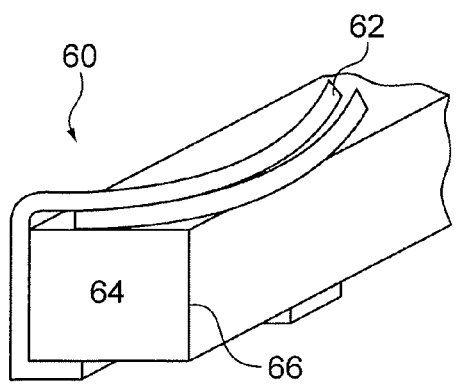
FIG. 9A is an enlarged perspective view of a portion of an endoprosthesis.
Figure 9B:
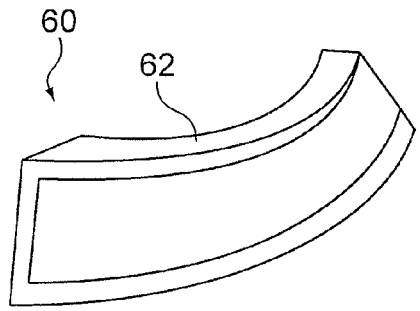
FIG. 9B is an enlarged perspective view of an embodiment of the portion of the endoprosthesis of FIG. 9A.

In some embodiments, as shown in FIG. 8A, a strut 50 has an initial circular geometry at the X-Y plane with initial radius and/or diameter. An erosion modifying layer 52 can intermittently coat the strut surface along the perimeter of the circular strut. Upon implantation, erosion starting at the uncoated surface 54 of strut 50 can result in a grooved geometry that maintains the initial radii in the lobe regions, for example, as shown in FIG. 8B. Referring to FIGS. 9A and 9B, in some embodiments, a strut 60 is coated with an erosion modifying layer 62. Erosion modifying layer 62 can curve along the Z-axis, for example, in a sinusoidal pattern. Upon implantation, erosion of an erodible body 64 starting at the uncoated surfaces 66 can result in a curved geometry along the Z axis. Further erosion can result in a I-beam geometry or grooved geometry.

Figure 10A:
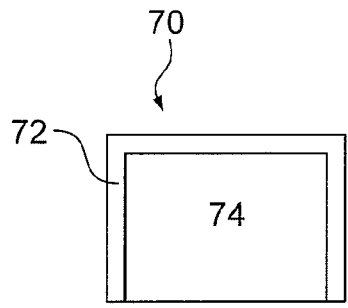
FIG. 10A is an enlarged cross-sectional view of an embodiment of a portion of an endoprosthesis.
Figure 10B:
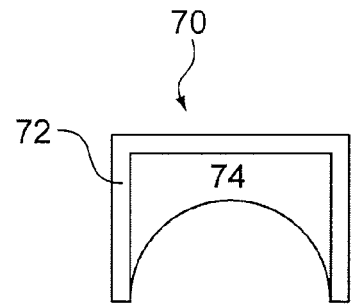
FIG. 10B is an enlarged cross-sectional view of an embodiment of the portion of the endoprosthesis of FIG. 10A.
Figure 11A:
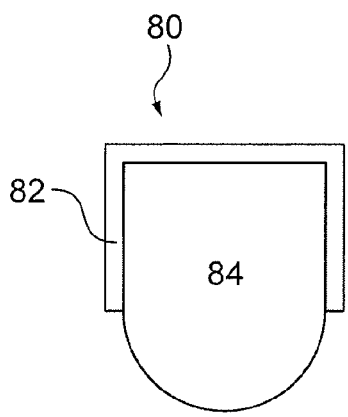
FIG. 11A is an enlarged cross-sectional view of a portion of an endoprosthesis.
Figure 11B:
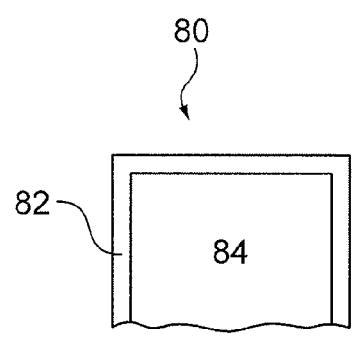
FIG. 11B is an enlarged cross-sectional view of an embodiment of a portion of the endoprosthesis of FIG. 11A.
Figure 11C:
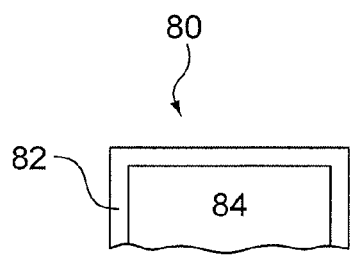
FIG. 11C is an enlarged cross-sectional view of an embodiment of a portion of an endoprosthesis of FIG. 11A.
Figure 12A:
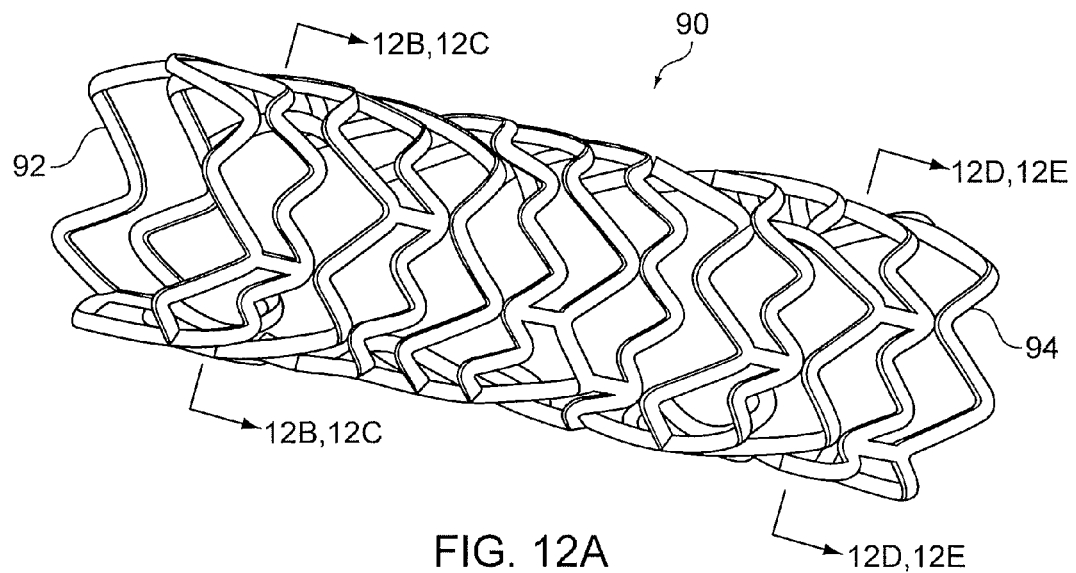
FIG. 12A is a perspective view of an embodiment of an endoprosthesis.
Figure 12B:
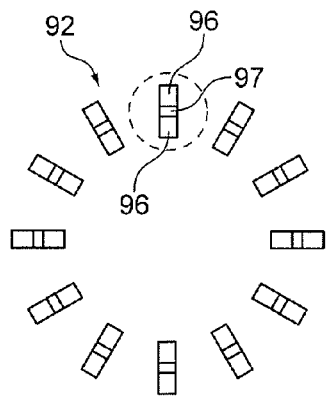
FIG. 12B is an enlarged cross-sectional view of the endoprosthesis of FIG. 12A.
Figure 12C:
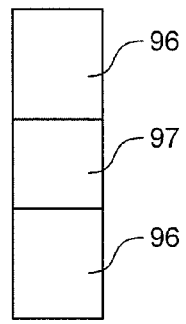
FIG. 12C is an enlarged cross-sectional view of a portion of the endoprosthesis of FIG. 12B.
Figure 12D:
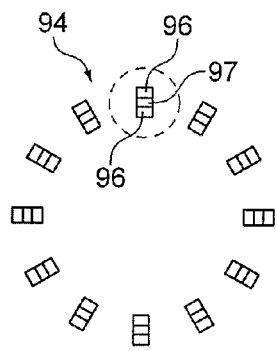
FIG. 12D is an enlarged cross-sectional view of the endoprosthesis of FIG. 12A.
Figure 12E:
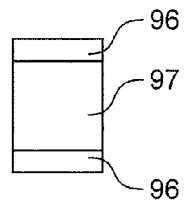
FIG. 12E is an enlarged cross-sectional view of a portion of the endoprosthesis of FIG. 12D.
Figure 13A:
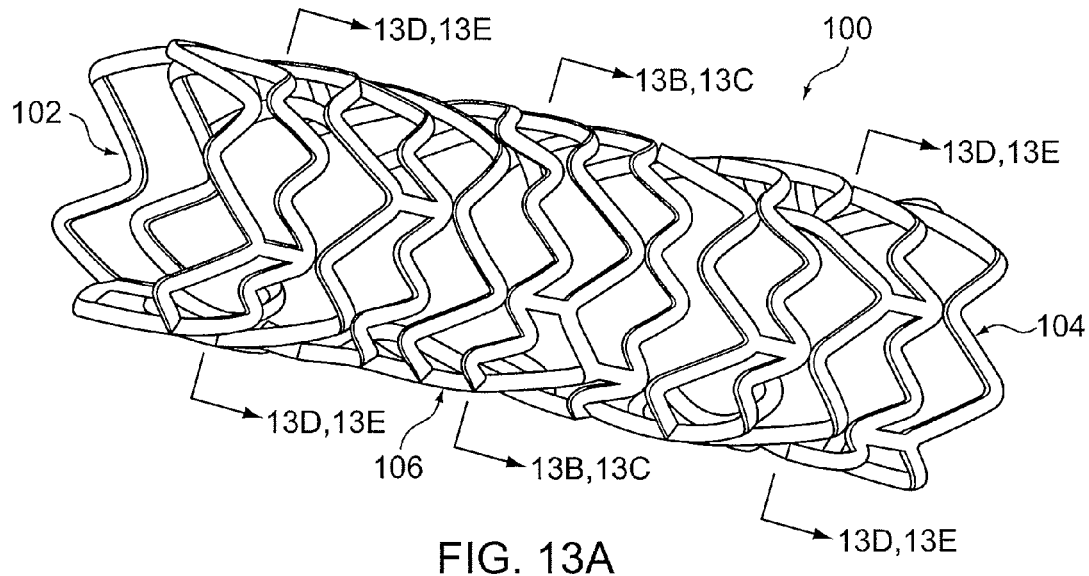
FIG. 13A is a perspective view of an embodiment of an endoprosthesis.
Figure 13B:
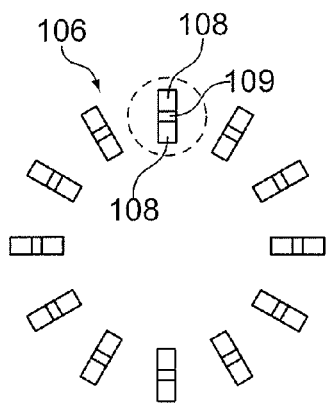
FIG. 13B is an enlarged cross-sectional view of the endoprosthesis of FIG. 13A.
Figure 13C:
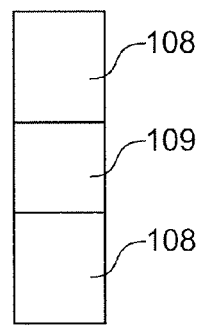
FIG. 13C is an enlarged cross-sectional view of a portion of the endoprosthesis of FIG. 13B.
Figure 13D:
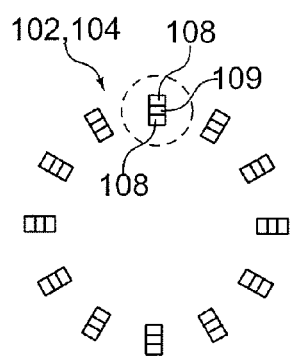
FIG. 13D is an enlarged cross-sectional view of the endoprosthesis of FIG. 13A.
Figure 13E:
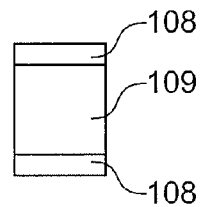
FIG. 13E is an enlarged cross-sectional view of a portion of the endoprosthesis of FIG. 13D.

In some embodiments, a strut can erode to generate a bioerodible body with, for example, an overall grooved geometry at the X-Y plane, an overall rectangular geometry at the X-Y plane, or combinations thereof. In some embodiments, an erosion modifying layer can coat two or more adjoining surfaces of a strut, or two or more non-adjoining surfaces of a strut. An endoprosthesis having a strut with one or more surfaces covered by an erosion modifying layer can, for example, have a lower erosion rate, maintain structural integrity for a longer duration, limit the degrees of freedom available for erosion, and reduce the risk associated with penetrating localized erosion and attendant fragmentation. Referring to FIGS. 10A and 11A, a strut 70, 80 coated with erosion modifying layers 72, 82 on three surfaces can erode to generate a bioerodible body 74, 84 having, for example, an overall grooved or concave geometry at the X-Y plane (e.g., FIG. 10B), or an overall rectangular cross-section (FIGS. 11B and 11C), or combinations thereof.

The erosion modifying layer can have a uniform thickness along the length of the endoprosthesis, or the erosion modifying layer can have a variable thickness distribution, which can tailor the rate and directionality of endoprosthesis erosion. In certain embodiments, an erosion modifying layer can have variable thickness throughout the length of the endoprosthesis. For example, as shown in FIGS. 12A, 12B, 12C, 12D, and 12E, an erosion modifying layer 96 can be thicker on a first end 92 of an endoprosthesis 90 and decrease gradually in thickness toward a second, opposite end 94 of endoprosthesis 90, thus allowing the second end of the endoprosthesis to erode before the first end. Layers 96 can be the same or different. As another example, as shown in FIGS. 13A, 13B, 13C, 13D, and 13E, an erosion modifying layer 108 can be thicker at a middle portion 106 of an endoprosthesis 100 than at the ends 102 and 104 of the endoprosthesis, thus allowing the ends of the endoprosthesis to erode before the middle of the endoprosthesis. Layers 108 can be the same or different. In some embodiments, the thicknesses of an erosion modifying layer at different surfaces on the strut can be the same or different. For example, to compensate for any difference in erosion rates between an interior surface and an exterior surface and to allow a cross-section of an endoprosthesis to erode relatively uniformly at the bioerodible body, an erosion modifying layer located at the interior may be thicker than a layer located at the exterior along the cross section of the endoprosthesis. In some embodiments, the thickness of an erosion modifying layer can change along a width of the strut.

Figure 14:
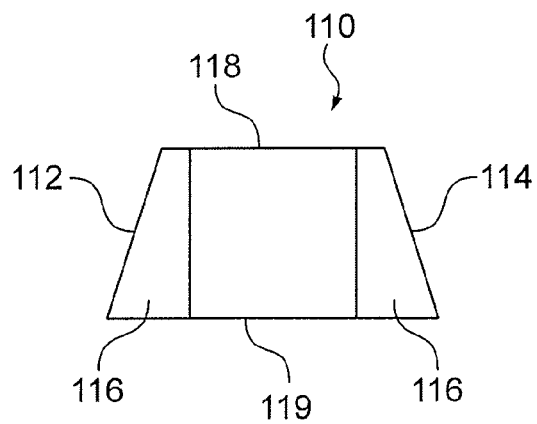
FIG. 14 is an enlarged cross-sectional view of an embodiment of a portion of an endoprosthesis.

As shown in FIG. 14, a strut 110 with two opposite side surfaces 112 and 114 coated with an erosion modifying layer 116 can have increasing thicknesses of the erosion modifying layer from an abluminal surface 118 to an interior surface 119. Layers 116 can be the same or different. In some embodiments, each of layers 96, 108, and 116 can include a plurality of layers, which can include the same or different materials. In some embodiments, within each layer, the composition can include the same or different materials at different portions of the layer.

An endoprosthesis can have struts having a rectangular cross-section, a square cross-section, a circular cross-section, an ovaloid cross-section, an elliptical cross-section, a polygonal cross-section (e.g., a hexagonal, an octagonal cross-section), or an irregularly shaped cross-section. The endoprosthesis can have an erosion modifying layer covering a portion of a total surface area of the endoprosthesis. In some embodiments, an erosion modifying layer covers at most 99 percent (e.g., at most about 90 percent, at most about 80 percent, at most about 70 percent, at most about 60 percent, at most about 50 percent, at most about 40 percent, at most about 30 percent, at most about 20 percent) and/or at least about 10 percent (e.g., at least about 20 percent, at least about 30 percent, at least about 40 percent, at least about 50 percent, at least about 60 percent, at least about 70 percent, at least about 80 percent) of a total surface area of an endoprosthesis.

In some embodiments, the erosion modifying layer can cover the entire surface of the endoprosthesis. The erosion modifying layer can include a plurality of layers, the composition of the layers can be the same or different. Within each layer, the composition can include the same or different materials at different portions of the layer. Depending on the materials in the erosion modifying layer(s), the erosion process can be tailored to follow a desired sequence. For example, one or more erosion modifying layers located at select portions of the endoprosthesis (e.g., the side surfaces of a strut) can include a more erodible material(s) that erodes prior to the remaining layers (e.g., located at the abluminal and adluminal surfaces of a strut), which can include a less erodible material(s). The erosion sequence can expose the endoprosthesis to body fluids at different locations and/or at different times during the lifetime of the endoprosthesis, which can produce a desired erosion geometry (e.g., an I-beam geometry).

In some embodiments, the erosion modifying layer and/or the bioerodible body have pores and/or patterns to adjust the erosion rate and/or erosion location of an endoprosthesis. As an example, an erosion modifying layer with open or closed pores extending throughout the layer can erode at a faster rate than a solid layer and/or allow the diffusion of body fluids through the erosion modifying layer, which can in turn allow the bioerodible body to erode at a faster rate. Pores can range in volume from about 500 nm$^3$ (e.g., from about 0.00005 µm$^3$, from about 0.0005 µm$^3$, from about 0.005 µm$^3$, from about 0.05 µm$^3$, from about 0.5 µm$^3$, from about 1 µm$^3$, from about 5 µm$^3$, from about 35 µm$^3$, or from about 50 µm$^3$) to about 550 µm$^3$ (e.g., to about 450 µm$^3$, to about 300 µm$^3$, to about 200 µm$^3$, to about 100 µm$^3$, to about 75 µm$^3$, to about 40 µm$^3$, to about 10 µm$^3$, to about 5 µm$^3$, to about 1 µm$^3$, to about 0.5 µm$^3$, to about 0.05 µm$^3$, to about 0.005 µm$^3$, or to about 0.00005 µm$^3$). As another example, a bioerodible endoprosthesis coated with a patterned erosion modifying layer can preferentially erode at certain exposed locations and can have controlled erosion geometries. A pattern includes a repeating sequence of one or more shapes or motifs, for example, grids, squares, circles, and/or lines. In some embodiments, an endoprosthesis having a patterned erosion modifying layer has enhanced endothelialization and reduced thrombus in a body lumen.

An erosion modifying layer located on the abluminal, adluminal, or the side surface of the strut can have the same chemical composition or different compositions. For example, an adluminal surface (e.g., FIG. 2, surface 12) can contact bodily fluid more than an abluminal surface (e.g., FIG. 2, surface 10), which can contact a wall of a body passageway, and as a result, the interior surface can erode more quickly than the exterior surface. To compensate for the difference in erosion and to allow a given cross-section of an endoprosthesis to erode relatively uniformly, the interior surface can have a layer having a chemical composition that erodes more slowly than the chemical composition of a layer at the exterior surface.

In some embodiments, the erosion rate of an endoprosthesis is tailored by changing the percentage of cold working of a metal or an alloy. Without being bound by theory, it is believed that cold working increases the susceptibility to erosion of a material by inducing dislocations and other defects in the structure, which tend to be anodic and corrode. For example, a bioerodible body can be cold-worked at a higher percentage than an erosion modifying layer so that the bioerodible body can erode before an erosion modifying layer.

Figure 15:
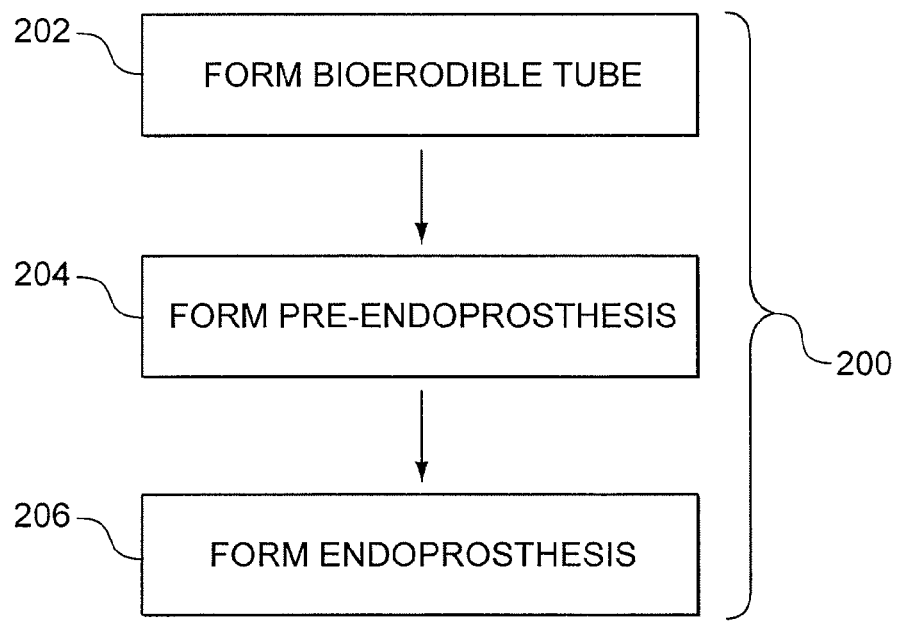
FIG. 15 is a sequence illustrating a method of making an endoprosthesis.

Referring to FIG. 15, a method 200 of making an endoprosthesis as described herein is shown. Method 200 includes forming a bioerodible tube (step 202), forming a pre-endoprosthesis from the bioerodible tube (step 204), and applying one or more erosion modifying layers to the pre-endoprosthesis (step 206) to form an endoprosthesis. In some embodiments, one or more erosion modifying layers are applied to the bioerodible tube, and the tube with the applied erosion modifying layer(s) is subsequently formed into an endoprosthesis.

The bioerodible tube can be formed (step 202) by manufacturing a tubular member including (e.g., is formed of) one or more bioerodible materials and capable of supporting a bodily lumen. For example, a mass of bioerodible material can be machined into a rod that is subsequently drilled to form the tubular member. As another example, a sheet of bioerodible material can be rolled to form a tubular member with overlapping portions, or opposing end portions of the rolled sheet can be joined (e.g., welded) together to form a tubular member. A bioerodible material can also be extruded to form a tubular member. In certain embodiments, a bioerodible tube can be made by thermal spraying, powder metallurgy, thixomolding, die casting, gravity casting, and/or forging. The bioerodible or erodible material can be a substantially pure metallic element, an alloy, or a composite. Examples of metallic elements include iron, magnesium, zinc, and alloys thereof. Examples of alloys include iron alloys having, by weight, 88-99.8% iron, 0.1-7% chromium, 0-3.5% nickel, and less than 5% of other elements (e.g., magnesium and/or zinc); or 90-96% iron, 3-6% chromium and 0-3% nickel plus 0-5% other metals. Other examples of alloys include magnesium alloys, such as, by weight, 50-98% magnesium, 0-40% lithium, 0-5% iron and less than 5% other metals or rare earths; or 79-97% magnesium, 2-5% aluminum, 0-12% lithium and 1-4% rare earths (such as cerium, lanthanum, neodymium and/or praseodymium); or 85-91% magnesium, 6-12% lithium, 2% aluminum and 1% rare earths; or 86-97% magnesium, 0-8% lithium, 2%-4% aluminum and 1-2% rare earths; or 8.5-9.5% aluminum, 0.15%-0.4% manganese, 0.45-0.9% zinc and the remainder magnesium; or 4.5-5.3% aluminum, 0.28%-0.5% manganese and the remainder magnesium; or 55-65% magnesium, 30-40% lithium and 0-5% other metals and/or rare earths. Magnesium alloys are also available under the names AZ91D, AM50A, and AE42. Other erodible materials are described in Bolz, U.S. Pat. No. 6,287,332 (e.g., zinc-titanium alloy and sodium-magnesium alloys); Heublein, U.S. Patent Application 2002000406; and Park, *Science and Technology of Advanced Materials*, 2, 73-78 (2001), all of which are hereby incorporated by reference herein in their entirety. In particular, Park describes Mg—X—Ca alloys, e.g., Mg—Al—Si—Ca, Mg—Zn—Ca alloys. Other suitable alloys include strontium. As an example, strontium can be a component in a magnesium alloy. The bioerodible tube can include more than one bioerodible material, such as different bioerodible materials physically mixed together, multiple layers of different bioerodible materials, and/or multiple sections of different bioerodible materials along a direction (e.g., length) of the tube. An example of a composite is as a mixture of a magnesium alloy in a bioerodible polymer, in which two or more distinct substances (e.g., metals, ceramics, glasses, and/or polymers) are intimately combined to form a complex material.

As shown in FIG. 15, after the bioerodible tube is formed, the tube is formed into a pre-endoprosthesis (step 204). In some embodiments, selected portions of the tube can be removed to form circular and connecting struts (e.g., 6, 8) by laser cutting, as described in U.S. Pat. No. 5,780,807, hereby incorporated by reference in its entirety. Other methods of removing portions of the tube can be used, such as mechanical machining (e.g., micro-machining, grit blasting or honing), electrical discharge machining (EDM), and photoetching (e.g., acid photoetching). The pre-endoprosthesis can be etched and/or electropolished to provide a selected finish. In certain embodiments, such as jelly-roll type endoprostheses, step 204 is omitted.

Next, the erosion modifying layer(s) is applied to the pre-endoprosthesis (step 206) to form an endoprosthesis. Prior to applying the erosion modifying layer, selected surfaces (e.g., interior surface) or portions (e.g., portion between the end portions of the endoprosthesis) of the pre-endoprosthesis can be masked so that the erosion modifying layer will not be applied to the masked surfaces or portions. In some embodiments, prior to applying the erosion modifying layer, pores can be formed on the pre-endoprosthesis (e.g., by micro-arc surface modification, sol-gel templating processes, near net shape alloy processing technology such as powder injection molding, adding foaming structures into a melt or liquid metal, melting a powder compact containing a gas evolving element or a space holder material, incorporating a removable scaffold (e.g., polyurethane) in a metal powder/slurry prior to sintering, sintering hollow spheres, sintering fibers, combustion synthesis, powder metallurgy, bonded fiber arrays, wire mesh constructions, vapor deposition, three-dimensional printing, and/or electrical discharge compaction). In some embodiments, pores can be formed by incorporating embedded microparticles and/or compounds (e.g., a salt) within the antioxidant layer (e.g., a polymerizable monomer, a polymer, a metal alloy), forming the antioxidant layer, and removing (e.g., dissolving, leaching, burning) the microparticles and/or compounds to form pores at locations where the microparticles and/or compounds were embedded. Removable (e.g., dissolvable) microparticles can be purchased, for example, from MicroParticles GmbH. In some embodiments, pores are formed by using a gas as a porogen, bonding fibers, and/or phase separation in materials such as polymers, metals, or metal alloys.

Suitable erosion modifying layer materials can include a polymer including covalently bound C, N, O, and halogen, a ceramic material, an oxide, a carbide, a halide, a metal, a metallic alloy, and/or a metal-containing polymer. For example, suitable polymers include bioerodible polymers as polylactic acid (PLA), polylactic glycolic acid (PLGA), polyanhydrides (e.g., poly(ester anhydride)s, fatty acid-based polyanhydride, amino acid-based polyanhydride), polyesters, polyester-polyanhydride blends, polycarbonate-polyanhydride blends, and/or combinations thereof. Suitable ceramic materials include, for example, iridium oxide. Suitable oxides include magnesium oxide, titanium oxide, and/or aluminum oxide. Suitable nitrides include magnesium nitride, titanium nitride, titanium oxynitride, iron nitride, and/or silicon nitride. Suitable carbides include iron carbide and silicon nitride. Suitable halides include magnesium fluoride. Suitable metals and/or a metallic alloys include stainless steel, titanium, niobium, a radiopaque metal such as gold, platinum, iridium, and alloys thereof; an alloy such as bioerodible magnesium alloys and iron alloys as previously described having adjusted compositions so that erosion occurs at a different rate than the bioerodible body. Suitable inert or dissolvable polymers including metals (e.g., Fe, Au, Pt) or metal compounds such as organometallic complexes. Depending on the erosion modifying layer material, one or more material can be dissolved in a solvent and applied to the pre-endoprosthesis, and/or two or more different materials can be blended together in the form of, for example, a composite such as a metal matrix composite (e.g., in a manner that one material is embedded or encapsulated in a remaining material) and applied to the pre-endoprosthesis. In some embodiments, for example, erosion modifying coatings are generated by physical or plasma vapor deposition, thermal metal spraying, dip coating, electrostatic spraying, conventional air atomization spraying, ion implantation (e.g., by plasma immersion ion implantation, by laser-driven ion implantation), electrochemical deposition, oxidation (e.g., anodizations), chemical grafting, interlayer transitional coatings to bond multiple layers, and/or metallurgical augmentation (e.g., peening, localized metallurgical treatments). In some embodiments, pores are generated in an erosion modifying layer, e.g., by powder injection molding sol-gel templating processes, near net shape alloy processing technology such as powder injection molding, micro-arc surface modification, sol-gel templating processes, adding foaming structures into a melt or liquid metal, melting a powder compact containing a gas evolving element or a space holder material, incorporating a removable scaffold (e.g., polyurethane) in a metal powder/slurry prior to sintering, sintering hollow spheres, sintering fibers, combustion synthesis, powder metallurgy, bonded fiber arrays, wire mesh constructions, vapor deposition, three-dimensional printing, and/or electrical discharge compaction). In some embodiments, pores can be formed by incorporating embedded microparticles and/or compounds (e.g., a salt) within the antioxidant layer (e.g., a polymerizable monomer, a polymer, a metal alloy), forming the antioxidant layer, and removing (e.g., dissolving, leaching, burning) the microparticles and/or compounds to form pores at locations where the microparticles and/or compounds were embedded. Removable (e.g., dissolvable) microparticles can be purchased, for example, from MicroParticles GmbH. In some embodiments, pores are formed by using a gas as a porogen, bonding fibers, and/or phase separation in materials such as polymers, metals, or metal alloys. In certain embodiments, patterns are generated in an erosion modifying layer, e.g., by laser ablation, lithography, ink-jet printing, and/or screen printing.

In some embodiments, a medicament is incorporated into an erosion modifying coating on an endoprosthesis. For example, a medicament can be adsorbed onto an erosion modifying coating on an endoprosthesis. A medicament can be encapsulated in a bioerodible material and embedded in an erosion modifying coating on an endoprosthesis. As another example, a medicament can be dissolved in a polymer solution and coated onto an endoprosthesis. Incorporation of a medicament is described in U.S. Ser. No. 10/958,435 filed Oct. 5, 2004, hereby incorporated by reference.

Figure 16:
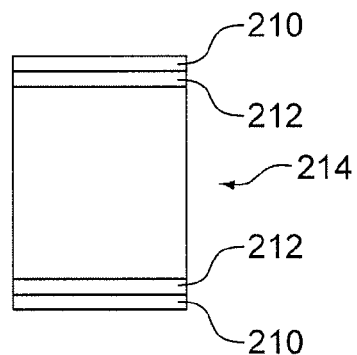
FIG. 16 is an enlarged cross-sectional view of an embodiment of a portion of an endoprosthesis.

In some embodiments, an endoprosthesis can have greater than one type of erosion modifying coating located at the same or different locations on the endoprosthesis. Referring to FIG. 16, as an example, an endoprosthesis can have a polymer coating 210 superimposed upon a stainless steel coating 212 on a strut 214. As another example, an endoprosthesis can have a ceramic coating on an exterior surface, and a polymer coating on an interior surface of a strut. In certain embodiments, an erosion modifying layer can be applied to a pre-endoprosthesis in one layer, or in multiple layers (e.g., at least two layers, at least three layers, at least four layers, at least five layers) in order, for example, to provide greater control over the thickness of an erosion modifying layer. Within an erosion modifying layer, the thickness and composition of a second material can be the same or different to provide desired erosion rates and erosion sequence. For example, the intermediate portion of an endoprosthesis can have a smaller thickness of a non-bioerodible second material than the end portions of the endoprosthesis, which can contain a greater thickness of a bioerodible second material. The erosion modifying layers can be applied the same way or in different ways. For example, a first, innermost erosion modifying layer can be plasma-deposited on the pre-endoprosthesis, and a second, outer erosion modifying layer can include a polymer that is dip-coated onto the first layer.

Figure 17:
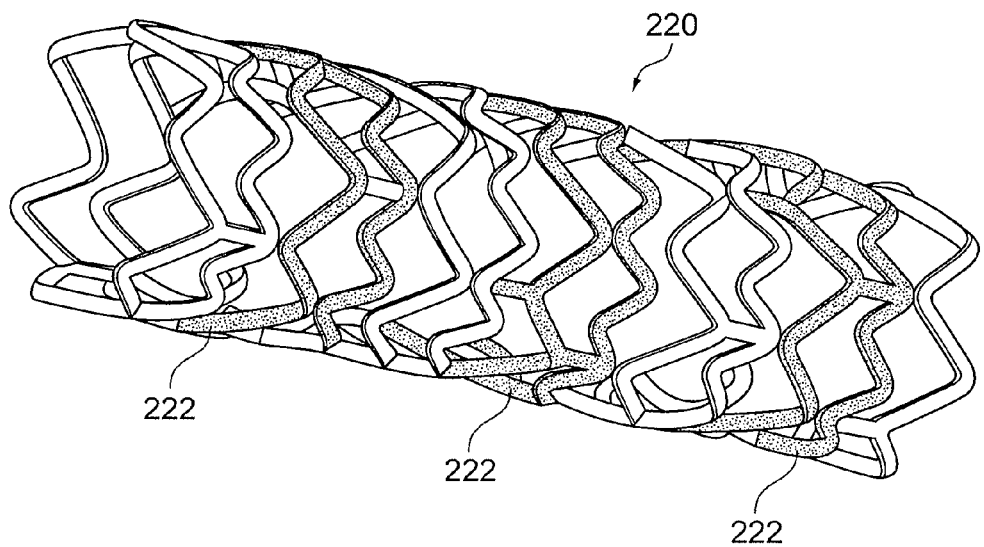
FIG. 17 is a perspective view of an embodiment of an endoprosthesis.
Figure 18:
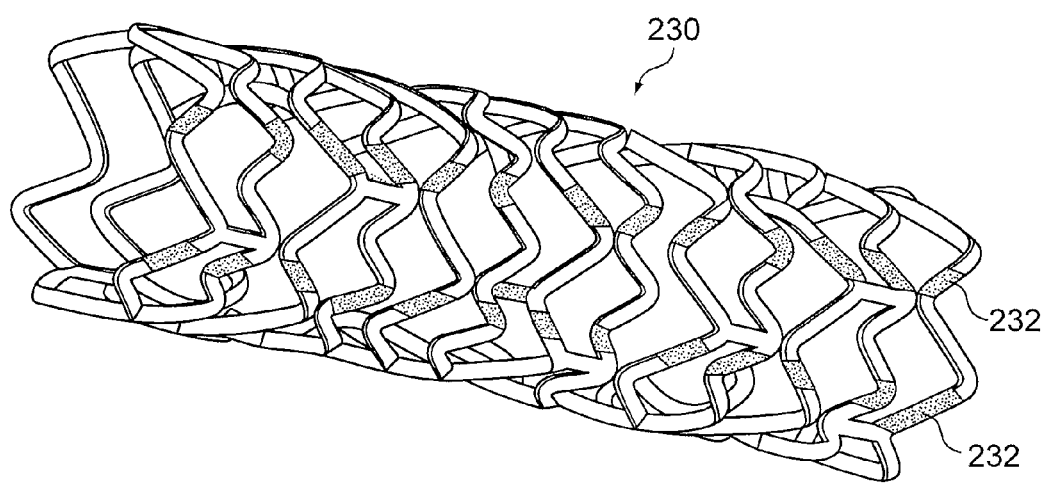
FIG. 18 is a perspective view of an embodiment of an endoprosthesis.

In some embodiments, an erosion modifying coating partially coats one or more portions of an endoprosthesis. Referring to FIG. 17, as an example, an endoprosthesis 220 can have a band(s) 222 of the same or different coatings along the length of the endoprosthesis. As shown in FIG. 18, as an example, an endoprosthesis 230 can have a strip(s) of the same or different coatings along the circumference of the endoprosthesis. Bands and strips can be coated onto the endoprosthesis by selectively masking certain areas of the endoprosthesis. Bands and strips of erosion modifying coating can have pore/patterns, and/or have different thicknesses as discussed above.

Figure 19:
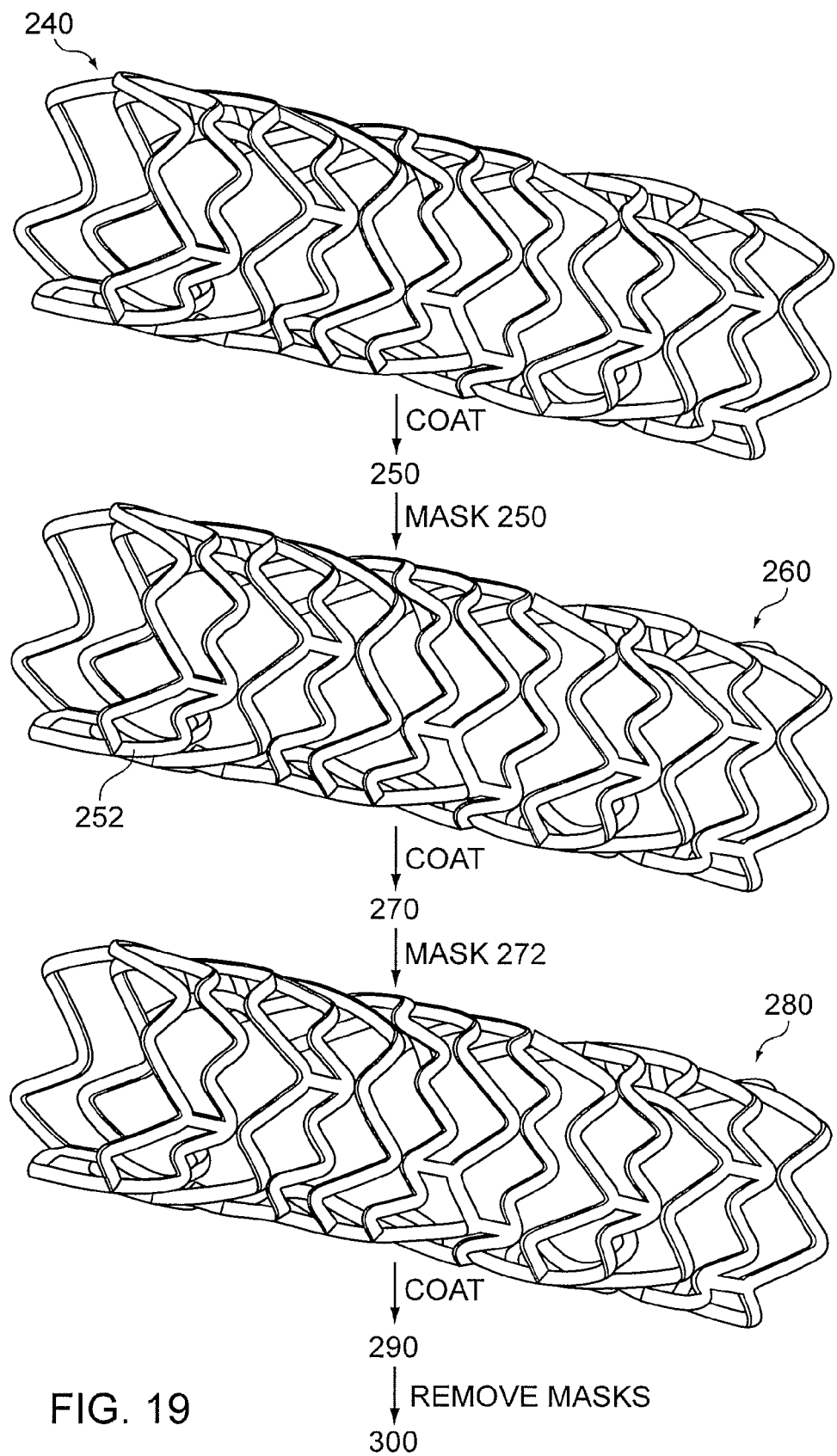
FIG. 19 is a sequence illustrating a method of making an endoprosthesis.

Referring now to FIG. 19, an endoprosthesis 300 having an increasing number of different erosion modifying layers along its length can be produced from a metallic pre-endoprosthesis 240 by masking selective portions of the endoprosthesis. For example, during production, all portions of the pre-endoprosthesis can be coated with a first erosion modifying layer to generate a pre-endoprosthesis 250. Next, a portion 252 of the pre-endoprosthesis is masked (e.g., with a protective polymeric coating such as a styrene-isoprene-butadiene-styrene (SIBS) polymer), which protects the masked portion from further erosion modifying layer coating, and the remaining section is coated with a second erosion modifying layer to make a pre-endoprosthesis 270. Finally, a second portion 272 of the pre-endoprosthesis is masked, and the remaining portion is further coated with a third erosion modifying layer to make pre-endoprosthesis 290. The protective coatings can be removed, e.g., by rinsing in a solvent such as toluene to complete the production of endoprosthesis 300. An endoprosthesis having tapered thicknesses can be produced by masking the interior and/or outer portions with a movable sleeve and longitudinally moving the sleeve and/or the endoprosthesis relative to each other during implantation.

In some embodiments, the erosion modifying layer(s) can be applied to the bioerodible tube prior to forming the bioerodible tube into an endoprosthesis (if necessary). As a result, the endoprosthesis can have its exterior and interior surfaces coated with the erosion modifying layer(s), and the side surfaces of the endoprosthesis can be free of the erosion modifying layer(s). Prior to applying the erosion modifying layer(s), the interior surface or the exterior surface of the bioerodible tube can be masked to apply the erosion modifying layer(s) to only selected portion(s) of the tube.

As another example, while the endoprosthesis can have both exterior and interior surfaces coated with a desired erosion modifying layer material, in other embodiments, one or more segments of an endoprosthesis have only the exterior surfaces or the interior surfaces coated with an erosion modifying layer having a second material. Exterior surfaces of a pre-endoprosthesis can be coated with a desired second material, e.g., by placing a mandrel, a pin or a sleeve that is sized to mate with the selected inner surface(s) of the pre-endoprosthesis so that during coating, the second material is effectively blocked from entering interior surface of the pre-endoprosthesis. Such an endoprosthesis, after implantation, may have a cross-section that has only two materials: an exterior surface that is coated with the second material, and an interior surface that has not been coated. Interior surfaces of a pre-endoprosthesis can be coated with a desired erosion modifying layer material, e.g., by placing a polymeric coating on selected outer surface(s) of the pre-endoprosthesis so that during coating the second material can coat only the interior surface(s) and is prevented from coating the exterior surfaces. Alternatively, exterior surfaces can be protected by placing the pre-endoprosthesis in a tight-fitting tube, e.g., a heat shrink tube, to cover the exterior surfaces. In some embodiments, photolithography and/or stereo-lithography can be used to mask surfaces of a pre-endoprosthesis to prevent coating of an erosion modifying layer material.

In use, the endoprostheses can be used, e.g., delivered and expanded, using a catheter delivery system, such as a balloon catheter system. Catheter systems are described in, for example, Wang U.S. Pat. No. 5,195,969, Hamlin U.S. Pat. No. 5,270,086, and Raeder-Devens, U.S. Pat. No. 6,726,712. Endoprosthesis and endoprosthesis delivery are also exemplified by the Radius® or Symbiot® systems, available from Boston Scientific Scimed, Maple Grove, Minn.

The endoprostheses described herein can be of a desired shape and size (e.g., coronary stents, aortic stents, peripheral vascular stents, gastrointestinal stents, urology stents, and neurology stents). Depending on the application, the stent can have a diameter of between, for example, 1 mm to 46 mm. In certain embodiments, a coronary stent can have an expanded diameter of from about 2 mm to about 6 mm. In some embodiments, a peripheral stent can have an expanded diameter of from about 5 mm to about 24 mm. In certain embodiments, a gastrointestinal and/or urology stent can have an expanded diameter of from about 6 mm to about 30 mm. In some embodiments, a neurology stent can have an expanded diameter of from about 1 mm to about 12 mm. An abdominal aortic aneurysm (AAA) stent and a thoracic aortic aneurysm (TAA) stent can have a diameter from about 20 mm to about 46 mm.

Figure 20A:
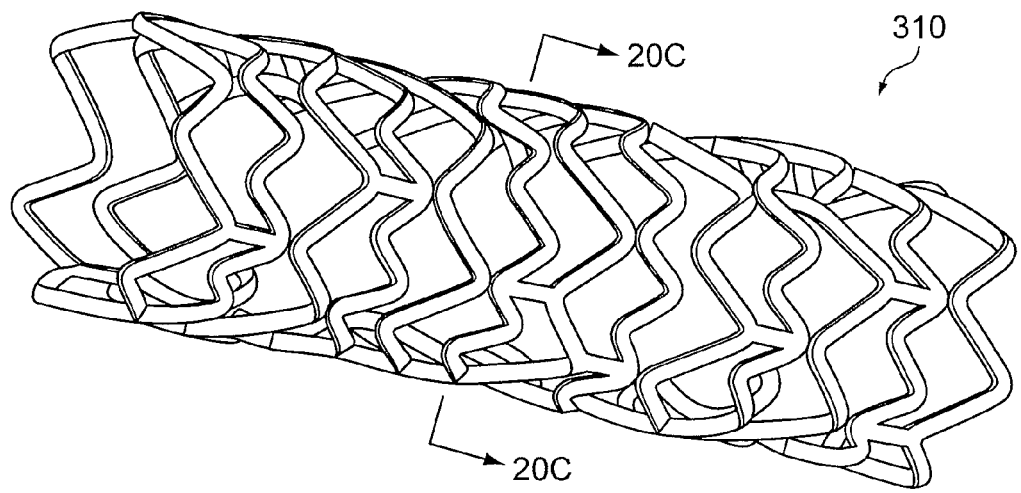
FIG. 20A is a perspective view of an embodiment of an endoprosthesis.
Figure 20B:
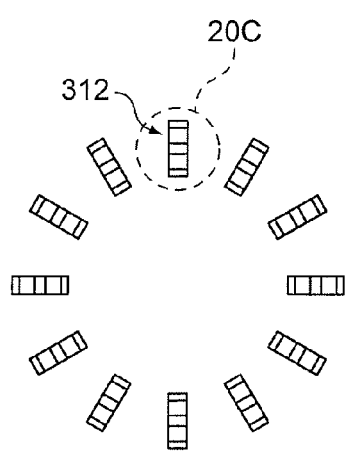
FIG. 20B is an enlarged cross-sectional view of the endoprosthesis of FIG. 20A.
Figure 20C:
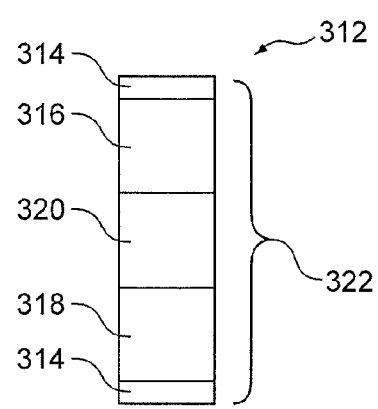
FIG. 20C is an enlarged cross-sectional view of a portion of the endoprosthesis of FIG. 20B.

While a number of embodiments have been described, the invention is not so limited. In some embodiments, the erosion rate of a bioerodible material is increased by forming, for example, a galvanic couple that is exposed to body fluids or an electrolyte solution. For example, the erosion rate of a bioerodible material (e.g., a magnesium alloy) can be increased by addition of one or more other materials such as iron, nickel, copper, and cobalt, and/or low level impurities such as gold, platinum, and iridium. Referring to FIGS. 20A, 20B, and 20C, an endoprosthesis 310 can have a strut 312, which can have a bioerodible body 322 having an inner portion 318, a center portion 320, an exterior portion 316, and two erosion modifying layers 314. Depending on the composition and thicknesses of the portions, the endoprosthesis can be configured to erode sequentially from an interior portion to an exterior portion, from an exterior surface to an interior surface, from a center portion to the exterior and interior portions, or from the exterior and interior portions to the center portion. This construction can allow the endoprosthesis to support the body vessel initially using the strength of multiple layers, and to reduce in thickness over time (e.g., after cells have endothelialized the endoprosthesis). The reduction in thickness can enhance the flexibility the endoprosthesis to better match the natural state of the body vessel. As another example, an endoprosthesis can have multiple alloy compositions along the length of a bioerodible body. For example, an alloy composition having a greater rate of erosion can be located at a first end of the bioerodible body, while an alloy composition having a smaller rate of erosion can be located at a second end of the bioerodible body, such that the first end erodes at a faster rate than the second end. The erosion directionality can allow for increased maintenance of patency for certain locations (e.g., weakened locations) in a body vessel.

The endoprostheses described herein can be a part of a stent, a covered stent or a stent-graft. For example, an endoprosthesis can include and/or be attached to a biocompatible, non-porous or semi-porous polymer matrix made of polytetrafluoroethylene (PTFE), expanded PTFE, polyethylene, urethane, or polypropylene.

The endoprostheses described herein can include non-metallic structural portions, e.g., polymeric portions. The polymeric portions can be erodible. The polymeric portions can be formed from a polymeric alloy. Polymeric stents have been described in U.S. patent application Ser. No. 10/683,314, filed Oct. 10, 2003; and U.S. patent application Ser. No. 10/958,435, filed Oct. 5, 2004, the entire contents of each is hereby incorporated by reference herein.

The endoprostheses can include a releasable therapeutic agent, drug, or a pharmaceutically active compound, such as described in U.S. Pat. No. 5,674,242, U.S. Ser. No. 09/895,415, filed Jul. 2, 2001, U.S. Ser. No. 11/111,509, filed Apr. 21, 2005, and U.S. Ser. No. 10/232,265, filed Aug. 30, 2002. The therapeutic agents, drugs, or pharmaceutically active compounds can include, for example, anti-thrombogenic agents, antioxidants, anti-inflammatory agents, anesthetic agents, anti-coagulants, and antibiotics. The therapeutic agent, drug, or a pharmaceutically active compound can be dispersed in a polymeric coating carried by the endoprosthesis. The polymeric coating can include more than a single layer. For example, the coating can include two layers, three layers or more layers, e.g., five layers. The therapeutic agent can be a genetic therapeutic agent, a non-genetic therapeutic agent, or cells. Therapeutic agents can be used singularly, or in combination. Therapeutic agents can be, for example, nonionic, or they may be anionic and/or cationic in nature. An example of a therapeutic agent is one that inhibits restenosis, such as paclitaxel. The therapeutic agent can also be used, e.g., to treat and/or inhibit pain, encrustation of the endoprosthesis or sclerosing or necrosing of a treated lumen. Any of the above coatings and/or polymeric portions can be dyed or rendered radio-opaque.

The endoprostheses described herein can be configured for non-vascular lumens. For example, it can be configured for use in the esophagus or the prostate. Other lumens include biliary lumens, hepatic lumens, pancreatic lumens, uretheral lumens and ureteral lumens.

Figure 21:
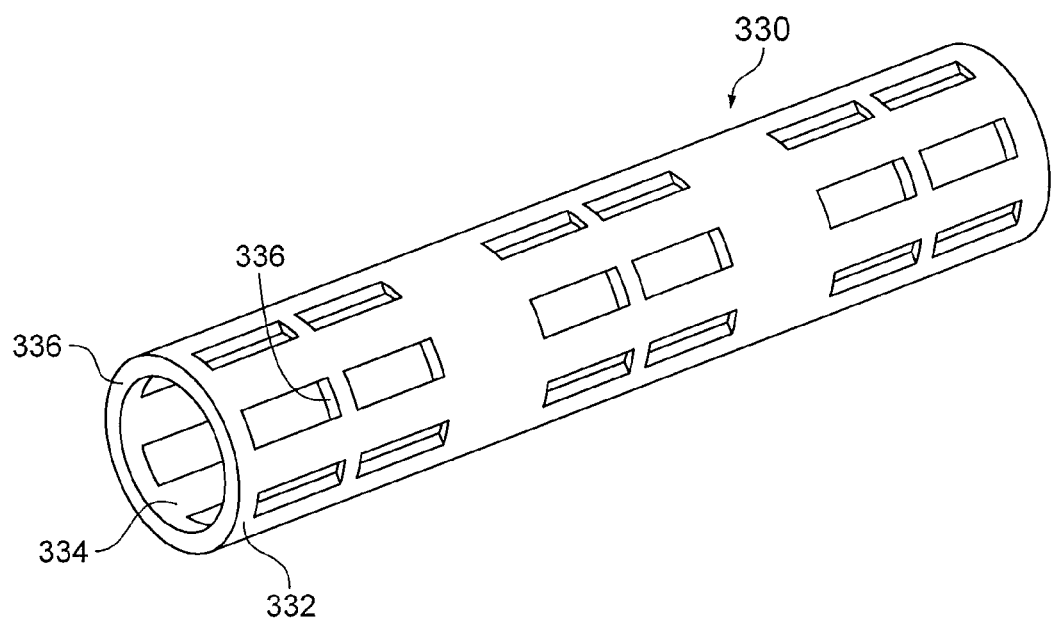
FIG. 21 is a perspective view of an embodiment of an endoprosthesis.
Figure 22:
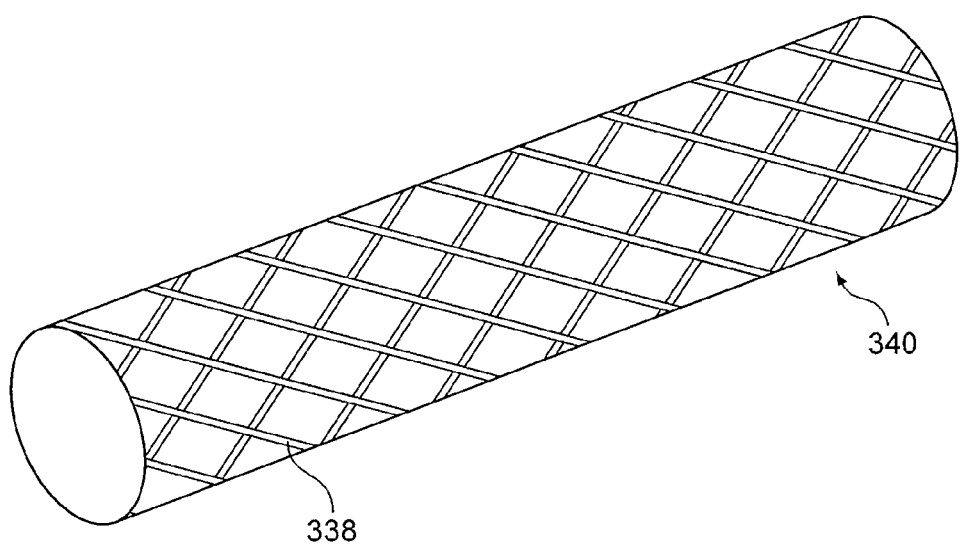
FIG. 22 is a perspective view of an embodiment of an endoprosthesis.

Other configurations of endoprosthesis are also possible. Referring to FIG. 21, an endoprosthesis 330 can have a tubular body with slots removed from the tubular body, an erosion modifying layer(s) can be coated onto an exterior surface 332, an interior surface 334, or any of the side surfaces 336 of the endoprosthesis. Referring to FIG. 22, an endoprosthesis 340 can have a braided or woven tubular body made of intertwining filaments 338. The endoprosthesis can be coated with an erosion modifying layer(s) on the exterior or the interior of the tubular body. In some embodiments, a braided endoprosthesis can include erosion modifying layer-coated and uncoated filaments.

All references, such as patent applications, publications, and patents, referred to herein are incorporated by reference in their entirety.

Other embodiments are within the claims.

What is claimed is:

1. An endoprosthesis, comprising:
a plurality of struts, the plurality of struts comprising a plurality of generally circumferential struts being interconnected to one another or connected by one or more connecting struts, wherein at least one strut of the plurality of struts comprises a bioerodible magnesium or a bioerodible magnesium alloy, the at least one strut having a longest dimension extending in a z-axis, the at least one strut having a cross-section in an X-Y plane perpendicular to the z-axis, wherein the at least one strut has an initial geometry in the X-Y plane characterized by initial dimensions, and
an erosion modifying material provided on the surface of the at least one strut which controls erosion to form a predetermined geometry such that, after erosion of at least about 50 percent of the area of the at least one strut in the X-Y plane, at least one initial dimension of the initial geometry is maintained in the X-Y plane.

2. The endoprosthesis of claim 1, wherein the initial dimension is maintained after erosion of at least about 75 percent of the area of the at least one strut in the X-Y plane.

3. The endoprosthesis of claim 1, wherein the initial dimension maintained corresponds to a maximum dimension of the initial geometry.

4. The endoprosthesis of claim 1, wherein the predetermined geometry is an X.

5. The endoprosthesis of claim 1, wherein the predetermined geometry is an interdigitated geometry.

6. The endoprosthesis of claim 1, wherein the predetermined geometry is a radially lobed structure.

7. The endoprosthesis of claim 1, wherein the predetermined geometry is a convex structure.

8. The endoprosthesis of claim 1, wherein the predetermined geometry is square or rectangular.

9. The endoprosthesis of claim 1, wherein the predetermined geometry extends substantially the full extent of the strut in the Z direction.

10. The endoprosthesis of claim 1, wherein the initial geometry is square or rectangular.

11. The endoprosthesis of claim 1, wherein the initial geometry is circular, ovaloid or elliptical.

12. The endoprosthesis of claim 1, wherein the ratio of maximum initial dimensions in the X-Y plane is between about 2:1 and about 1:2.

13. The endoprosthesis of claim 1, wherein the erosion modifying material comprises a material selected from the group consisting of a polymer, a ceramic, an oxide, a metal, an alloy, and a composite.

14. The endoprosthesis of claim 1 wherein the erosion modifying material is provided as a layer, and the layer has varying thickness.

15. The endoprosthesis of claim 14 wherein the thickness varies in the X or Y direction.

16. The endoprosthesis of claim 14 wherein the thickness varies in the Z direction.

17. The endoprosthesis of claim 14 wherein the thickness varies along the length of the endoprosthesis.

18. The endoprosthesis of claim 1 formed of a plurality of struts arranged in the general form of a tube.

19. The endoprosthesis of claim 1, wherein the endoprosthesis is balloon expandable.

20. An endoprosthesis, comprising:
a strut comprising a bioerodible magnesium or a bioerodible magnesium alloy, the strut having a longest dimension extending in a z-axis, the strut having a cross-section in an X-Y plane perpendicular to the z-axis, wherein the strut has an initial geometry in the X-Y plane characterized by initial dimensions, and
an erosion modifying material provided on the surface of the strut which controls erosion to form an I-shape in the X-Y plane after erosion of at least about 50 percent of the area of the strut in the X-Y plane.

21. The endoprosthesis of claim 20, wherein the ends of the I correspond to abluminal and adluminal sides of the endoprosthesis.

22. An endoprosthesis, comprising:
a plurality of struts, the plurality of struts comprising a plurality of generally circumferential struts being interconnected to one another or connected by one or more connecting struts, wherein at least one strut of the plurality of struts comprises a bioerodible magnesium or a bioerodible magnesium alloy, at least one strut having an initial geometry in X, Y, and Z directions, the at least one strut having a longest dimension extending in the Z direction, the X, Y, and Z directions each being perpendicular to each other; and
an erosion modifying material provided on the surface of the at least one strut which controls erosion to form a predetermined geometry such that, after erosion of at least about 50 percent of the at least one strut, at least two initial dimensions in the X, Y, and Z directions are maintained.

23. The endoprosthesis of claim 1, wherein the bioerodible magnesium or the bioerodible magnesium alloy has an erosion rate of between about 0.2% and 5% of its initial mass per day.

* * * * *

UNITED STATES PATENT AND TRADEMARK OFFICE
CERTIFICATE OF CORRECTION

| | | |
|---|---|---|
| PATENT NO. | : 8,057,534 B2 | Page 1 of 1 |
| APPLICATION NO. | : 11/855516 | |
| DATED | : November 15, 2011 | |
| INVENTOR(S) | : Dennis A. Boismier | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 444 days.

Signed and Sealed this
Twenty-second Day of May, 2012

David J. Kappos
*Director of the United States Patent and Trademark Office*